United States Patent
Du et al.

(10) Patent No.: US 12,201,725 B2
(45) Date of Patent: *Jan. 21, 2025

(54) DRY POWDER COMPOSITIONS OF TREPROSTINIL PRODRUGS AND METHODS OF USE THEREOF

(71) Applicant: Insmed Incorporated, Bridgewater, NJ (US)

(72) Inventors: Ju Du, Bridgewater, NJ (US); Adam Plaunt, Phillipsburg, NJ (US); Vladimir Malinin, Plainsboro, NJ (US)

(73) Assignee: Insmed Incorporated, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/360,514

(22) Filed: Jul. 27, 2023

(65) Prior Publication Data
US 2024/0050373 A1   Feb. 15, 2024

Related U.S. Application Data

(63) Continuation of application No. 17/893,991, filed on Aug. 23, 2022, now Pat. No. 11,759,425, which is a continuation of application No. 16/860,428, filed on Apr. 28, 2020, now Pat. No. 11,458,098.

(60) Provisional application No. 62/840,186, filed on Apr. 29, 2019.

(51) Int. Cl.
A61K 9/14   (2006.01)
A61K 31/198   (2006.01)
A61K 31/216   (2006.01)

(52) U.S. Cl.
CPC .............. *A61K 9/146* (2013.01); *A61K 9/145* (2013.01); *A61K 31/198* (2013.01); *A61K 31/216* (2013.01)

(58) Field of Classification Search
None
See application file for complete search history.

(56) References Cited

U.S. PATENT DOCUMENTS

| | | |
|---|---|---|
| 4,367,237 A | 1/1983 | Wakatsuka et al. |
| 4,668,814 A | 5/1987 | Aristoff |
| 4,837,342 A | 6/1989 | Shibasaki et al. |
| 5,153,222 A | 10/1992 | Tadepalli et al. |
| 5,190,972 A | 3/1993 | Dumble |
| 5,234,953 A | 8/1993 | Crow et al. |
| 5,662,932 A | 9/1997 | Amselem et al. |
| 6,054,486 A | 4/2000 | Crow et al. |
| 6,165,500 A | 12/2000 | Cevc |
| 6,242,482 B1 | 6/2001 | Shorr et al. |
| 6,306,435 B1 | 10/2001 | Chen et al. |
| 6,521,212 B1 | 2/2003 | Cloutier et al. |
| 6,756,033 B2 | 6/2004 | Cloutier et al. |
| 6,803,386 B2 | 10/2004 | Shorr et al. |
| 7,199,157 B2 | 4/2007 | Wade et al. |

(Continued)

FOREIGN PATENT DOCUMENTS

| | | |
|---|---|---|
| CN | 101669904 A | 3/2010 |
| CN | 105848479 A | 8/2016 |

(Continued)

OTHER PUBLICATIONS

Chapman, R. W. et al. (2020), "An overview of the biology of a long-acting inhaled treprostinil prodrug," Pulmonary Pharmacology & Therapeutics, 65:102002, 14 pages.

(Continued)

*Primary Examiner* — Danah Al-Awadi
(74) *Attorney, Agent, or Firm* — Joshua Marcus; Dong Chen

(57) ABSTRACT

The present disclosure provides a dry powder composition of treprostinil prodrugs and a method of treating pulmonary hypertension (e.g., pulmonary arterial hypertension), portopulmonary hypertension, or pulmonary fibrosis in a patient in need thereof. The dry powder composition includes (a) from about 0.1 wt % to about 3 wt % of a compound of Formula (I):

(I)

or an enantiomer, diastereomer, or a pharmaceutically acceptable salt thereof, (b) from about 0.01 wt % to about 3 wt % of DSPE-PEG2000, (c) from about 10 wt % to about 50 wt % of leucine, and the balance being (d) a sugar selected from the group consisting of trehalose and mannitol. The entirety of (a), (b), (c), and (d) is 100 wt %, and $R^1$ is tetradecyl, pentadecyl, hexadecyl, heptadecyl, or octadecyl. The method includes administering an effective amount of the dry powder composition to the lungs of the patient by inhalation via a dry powder inhaler. In certain compositions and methods provided herein, $R^1$ is hexadecyl, e.g., linear hexadecyl.

20 Claims, 33 Drawing Sheets

(56) References Cited

U.S. PATENT DOCUMENTS

| | | |
|---|---|---|
| 7,384,978 B2 | 6/2008 | Phares et al. |
| 7,417,070 B2 | 8/2008 | Phares et al. |
| 7,544,713 B2 | 6/2009 | Phares et al. |
| 7,858,650 B2 | 12/2010 | Yamamoto et al. |
| 7,879,909 B2 | 2/2011 | Wade et al. |
| 7,999,007 B2 | 8/2011 | Jeffs et al. |
| 8,242,305 B2 | 8/2012 | Batra et al. |
| 8,349,892 B2 | 1/2013 | Phares |
| 8,350,079 B2 | 1/2013 | Walsh |
| 8,461,393 B2 | 6/2013 | Sharma |
| 8,481,782 B2 | 7/2013 | Batra et al. |
| 8,609,728 B2 | 12/2013 | Rothblatt et al. |
| 8,969,409 B2 | 3/2015 | Rothblatt et al. |
| 9,102,660 B2 | 8/2015 | Batra et al. |
| 9,255,064 B2 | 2/2016 | Malinin et al. |
| 9,469,600 B2 | 10/2016 | Malinin et al. |
| 9,593,061 B2 | 3/2017 | Batra et al. |
| 9,624,156 B2 | 4/2017 | Phares et al. |
| 10,010,518 B2 | 7/2018 | Malinin et al. |
| 10,343,979 B2 | 7/2019 | Malinin et al. |
| 10,526,274 B2 | 1/2020 | Malinin et al. |
| 10,995,055 B2 | 5/2021 | Malinin et al. |
| 11,148,997 B2 | 10/2021 | Malinin et al. |
| 11,458,098 B2 | 10/2022 | Du et al. |
| 11,759,425 B2 | 9/2023 | Du et al. |
| 11,795,135 B2 | 10/2023 | Malinin et al. |
| 2003/0022242 A1 | 1/2003 | Anderson |
| 2003/0108512 A1 | 6/2003 | Shorr et al. |
| 2003/0108743 A1 | 6/2003 | Anderson |
| 2004/0156816 A1 | 8/2004 | Anderson |
| 2005/0085540 A1 | 4/2005 | Phares et al. |
| 2005/0165111 A1 | 7/2005 | Wade et al. |
| 2005/0282901 A1 | 12/2005 | Phares et al. |
| 2005/0282903 A1 | 12/2005 | Wade et al. |
| 2007/0078095 A1 | 4/2007 | Phares et al. |
| 2008/0200449 A1 | 8/2008 | Olschewski et al. |
| 2008/0202513 A1 | 8/2008 | Birchall et al. |
| 2008/0249167 A1 | 10/2008 | Phares et al. |
| 2008/0280986 A1 | 11/2008 | Wade et al. |
| 2009/0036465 A1 | 2/2009 | Roscigno et al. |
| 2009/0074828 A1 | 3/2009 | Alexis et al. |
| 2010/0076083 A1 | 3/2010 | Olschewski et al. |
| 2010/0324313 A1 | 12/2010 | Hogan et al. |
| 2012/0004307 A1 | 1/2012 | Wade et al. |
| 2012/0010159 A1 | 1/2012 | Rothblatt et al. |
| 2012/0216801 A1 | 8/2012 | Olschewski et al. |
| 2013/0053581 A1 | 2/2013 | Wei et al. |
| 2013/0184295 A1 | 7/2013 | Sprague et al. |
| 2013/0261187 A1 | 10/2013 | Phares et al. |
| 2014/0193379 A1 | 7/2014 | Jeffs et al. |
| 2014/0256730 A1 | 9/2014 | Becker et al. |
| 2014/0275262 A1 | 9/2014 | Phares et al. |
| 2014/0275616 A1 | 9/2014 | Batra et al. |
| 2014/0323567 A1 | 10/2014 | Laing |
| 2015/0005374 A1 | 1/2015 | Phares et al. |
| 2015/0148414 A1 | 5/2015 | Malinin et al. |
| 2015/0166503 A1 | 6/2015 | Becker et al. |
| 2015/0175529 A1 | 6/2015 | Malinin et al. |
| 2015/0328232 A1 | 11/2015 | Malinin et al. |
| 2016/0235742 A1 | 8/2016 | Zisman |
| 2016/0256425 A1 | 9/2016 | Malinin et al. |
| 2016/0318844 A1 | 11/2016 | Malinin et al. |
| 2017/0049739 A1 | 2/2017 | Plaunt et al. |
| 2017/0304276 A1 | 10/2017 | Armer et al. |
| 2017/0320813 A1 | 11/2017 | Malinin et al. |
| 2018/0153847 A1 | 6/2018 | Phares et al. |
| 2018/0200186 A1 | 7/2018 | Chen et al. |
| 2019/0151332 A1 | 5/2019 | Roscigno et al. |
| 2019/0248731 A1 | 8/2019 | Malinin et al. |
| 2019/0337888 A1 | 11/2019 | Malinin et al. |
| 2020/0079724 A1 | 3/2020 | Malinin et al. |
| 2020/0338005 A1 | 10/2020 | Du et al. |
| 2021/0276940 A1 | 9/2021 | Malinin et al. |
| 2022/0135513 A1 | 5/2022 | Malinin et al. |
| 2022/0409537 A1 | 12/2022 | Du et al. |
| 2023/0250051 A1 | 8/2023 | Malinin et al. |
| 2024/0109834 A1 | 4/2024 | Malinin et al. |
| 2024/0122889 A1 | 4/2024 | O'Brien et al. |
| 2024/0238309 A1 | 7/2024 | Malinin et al. |

FOREIGN PATENT DOCUMENTS

| | | |
|---|---|---|
| CN | 114652704 A | 6/2022 |
| EP | 0496548 A1 | 7/1992 |
| EP | 0989108 A2 | 3/2000 |
| EP | 1161234 B1 | 7/2003 |
| EP | 1045695 B1 | 3/2004 |
| EP | 1696932 B1 | 9/2009 |
| EP | 1744739 B1 | 3/2010 |
| EP | 1696900 B1 | 7/2010 |
| EP | 2461812 B1 | 1/2014 |
| EP | 2792353 A2 | 10/2014 |
| EP | 2200650 B1 | 1/2016 |
| JP | S61289034 A | 12/1986 |
| JP | H08507515 A | 8/1996 |
| JP | 2002521423 A | 7/2002 |
| JP | 2002539154 A | 11/2002 |
| JP | 2006528969 A | 12/2006 |
| JP | 2007501281 A | 1/2007 |
| JP | 2008507585 A | 3/2008 |
| JP | 2009519972 A | 5/2009 |
| JP | 2009537246 A | 10/2009 |
| JP | 2012516187 A | 7/2012 |
| WO | WO-9933490 A1 | 7/1999 |
| WO | WO-0006120 A1 | 2/2000 |
| WO | WO-0057701 A1 | 10/2000 |
| WO | WO-2004103348 A2 | 12/2004 |
| WO | WO-2005007081 A2 | 1/2005 |
| WO | WO-2008098196 A1 | 8/2008 |
| WO | WO-2009152160 A1 | 12/2009 |
| WO | WO-2009158010 A1 | 12/2009 |
| WO | WO-2010036798 A1 | 4/2010 |
| WO | WO-2010039531 A1 | 4/2010 |
| WO | WO-2010129757 A1 | 11/2010 |
| WO | WO-2011003058 A1 | 1/2011 |
| WO | WO-2011022707 A1 | 2/2011 |
| WO | WO-2011089215 A1 | 7/2011 |
| WO | WO-2011089216 A1 | 7/2011 |
| WO | WO-2011153363 A1 | 12/2011 |
| WO | WO-2012009816 A1 | 1/2012 |
| WO | WO-2012107364 A1 | 8/2012 |
| WO | WO-2012111627 A1 | 8/2012 |
| WO | WO-2012124688 A1 | 9/2012 |
| WO | WO-2013024047 A1 | 2/2013 |
| WO | WO-2013024048 A1 | 2/2013 |
| WO | WO-2013024049 A1 | 2/2013 |
| WO | WO-2013024051 A1 | 2/2013 |
| WO | WO-2013024052 A1 | 2/2013 |
| WO | WO-2013024053 A1 | 2/2013 |
| WO | WO-2013174848 A2 | 11/2013 |
| WO | WO-2014022373 A1 | 2/2014 |
| WO | WO-2014022376 A2 | 2/2014 |
| WO | WO-2014085813 A1 | 6/2014 |
| WO | WO-2014110094 A1 | 7/2014 |
| WO | WO-2014110491 A1 | 7/2014 |
| WO | WO-2014203278 A2 | 12/2014 |
| WO | WO-2015061720 A2 | 4/2015 |
| WO | WO-2015138423 A1 | 9/2015 |
| WO | WO-2015192030 A1 | 12/2015 |
| WO | WO-2016081658 A1 | 5/2016 |
| WO | WO-2017192993 A1 | 11/2017 |
| WO | WO-2017223400 A1 | 12/2017 |
| WO | WO-2019237028 A1 | 12/2019 |
| WO | WO-2020136276 A1 | 7/2020 |
| WO | WO-2020223237 A1 | 11/2020 |
| WO | WO-2021195328 A1 | 9/2021 |
| WO | WO-2022094100 A1 | 5/2022 |
| WO | WO 2022/187352 | 9/2022 |

OTHER PUBLICATIONS

Chapman, R. W. et al. (2020), "No evidence of desensitization to repeat dosing with treprostinil palmitil inhalation suspension (TPIS)

(56) References Cited

OTHER PUBLICATIONS for 32-consecutive days in hypoxia- challenged telemetered rats," European Respiratory Journal, 56:1486; DOI: 10.1183/13993003. congress-2020.1486, 1 page.
Chapman, R. W. et al. (2021), "Characterisation of cough evoked by inhaled treprostinil and treprostinil palmitil," ERJ Open Res., 7:00592-2020, with Online Data Supplement, 35 pages.
ClinicalTrials.gov ID NCT04791514, Insmed Incorporated, "A Study of Treprostinil Palmitil Inhalation Powder (TPIP) In Pulmonary Arterial Hypertension (PAH), " Record History, ver. 1: Mar. 8, 2021, ClinicalTrials.gov, 10 pages.
ClinicalTrials.gov ID NCT04791514, Insmed Incorporated, "A Study of Treprostinil Palmitil Inhalation Powder (TPIP) In Pulmonary Arterial Hypertension (PAH)," Record History, ver. 2: May 12, 2021, ClinicalTrials.gov, 10 pages.
ClinicalTrials.gov ID NCT04791514, Insmed Incorporated, "A Study of Treprostinil Palmitil Inhalation Powder (TPIP) In Pulmonary Arterial Hypertension (PAH)," Record History, ver. 3: Jun. 8, 2021, ClinicalTrials.gov, 11 pages.
Corboz, M. et al. (2017), "Inhalation of dry powder INS1009 (DP-INS1009) does not activate the cough reflex in guinea pigs: a comparison with nebulized treprostinil," 50:PA2377; DOI: 10.1183/1393003.congress-2017, PA2377, 1 page.
Corboz, M. et al. (2020), "Comparison of Treprostinil Palmitil Inhalation Suspension (TPIS) or Oral Sildenafil (Sild) in a Sugen/Hypoxia Rat Model of PAH," European Respiratory Journal, 56:1481; DOI: 10.1183/13993003.congress-2020.1481, 1 page.
Corboz, M. R. et al. (2021), "Beneficial Effects of Treprostinil Palmitil in a Sugen/Hypoxia Rat Model of Pulmonary Arterial Hypertension; a Comparison with Inhaled and Intravenous Treprostinil and Oral Selexipag," Am J Respir Crit Care Med., 203:A3670, 1 page.
Corboz, M. R. et al. (2021), "Pulmonary Vasodilator Activity of Inhaled Treprostinil Palmitil, Inhaled Treprostinil, Intravenous Treprostinil and Oral Selexipag in Hypoxia-Challenged Rats," Am J Respir Crit Care Med., 203:A3678, 1 page.
Corboz, M. R. et al. (2022), "Treprostinil palmitil inhibits the hemodynamic and histopathological changes in the pulmonary vasculature and heart in an animal model of pulmonary arterial hypertension," European Journal of Pharmacology, 916:174484, 12 pages.
Corboz, M. R. et al. (Oct. 2022), "Assessment of Inhaled Treprostinil Palmitil, Inhaled and Intravenous Treprostinil, and Oral Selexipag in a Sugen/Hypoxia Rat Model of Pulmonary Arterial Hypertension," J Pharmacol Exp Ther 383:103-116.
Eedara, B. B. et al. (Jun. 2016), "Phospholipid-based pyrazinamide spray-dried inhalable powders for treating tuberculosis," International Journal of Pharmaceutics, vol. 506, Issues 1-2, pp. 174-183.
Extended European Search Report for European Application No. 20798330.5, mailed Jan. 2, 2023, 7 pages.
Gauani, H. et al. (Apr. 2022), "Evaluation and Selection of the Inhaler Device for Treprostinil Palmitil Inhalation Powder," Frontiers in Drug Delivery, vol. 2, Article 864922, 13 pages.
Gauani, H. et al. (Mar. 2023), "Effect of Inhalation Profile on Delivery of Treprostinil Palmitil Inhalation Powder," Pharmaceutics, 15, 934. https://doi.org/10.3390/pharmaceutics15030934, 17 pages.
Insmed Incorporated (Feb. 2021), "Insmed Announces Topline Results from Phase 1 Study of Treprostinil Palmitil Inhalation Powder (TPIP)," 4 pages.
Insmed Incorporated (Feb. 2021), "TPIP Phase 1 Topline Results," 23 pages.
Ismat, F. A. et al. (Sep. 2022), "Safety, Tolerability, and Pharmacokinetics of Treprostinil Palmitil Inhalation Powder for Pulmonary Hypertension: A Phase 1, Randomized, Double-Blind, Single- and Multiple-Dose Study," Adv Ther., 39:5144-5157.
Leifer, F. G. et al. (2018), "Inhaled Treprostinil-Prodrug Lipid Nanoparticle Formulations Provide Long-Acting Pulmonary Vasodilation," Drug Res (Stuttg), 68(11):605-614 (Original Article), with Supplementary Information, 18 pages.

Li, Z. et al. (2017), "Pharmacokinetic (pk) Comparison Between Nebulized And Dry Powder Ins1009 In Rats," B71 Pulmonary Hypertension Life: Animal Models and Ex Vivo Studies in Pulmonary Hypertension / Thematic Poster Session / Monday, May 22/9:15 AM-4:15 PM / Area G, Hall B-C (Middle Building, Lower Level) Walter E. Washington Convention Center, Am J Respir Crit Care Med., 195:A4200, 1 page.
Malinin, V. et al. (2015), "A 14-Day Assessment Of The Tolerability And Pharmacokinetics (pk) With A Nanoparticle Formulation Of Hexadecyl-Treprostinil, A Long-Acting Pulmonary Vasodilator, In Rats," A52 Preclinical Trials in Pulmonary Hypertension Models: Novel Targets and Delivery / Thematic Poster Session / Sunday, May 17/9:30 AM-4:15 PM / Area E, Hall A-B (Upper Level) Colorado Convention Center, Am J Respir Crit Care Med., 191:A1948, 1 page.
Malinin, V. et al. (2017), "Ins1009, An Inhaled Prodrug Hexadecyl-Treprostinil, Demonstrates Local Pulmonary Vasodilation Activity In Dogs," B71 Pulmonary Hypertension Life: Animal Models and Ex Vivo Studies in Pulmonary Hypertension / Thematic Poster Session / Monday, May 22/9:15 AM-4:15 PM / Area G, Hall B-C (Middle Building, Lower Level) Walter E. Washington Convention Center, Am J Respir Crit Care Med., 195:A4213, 1 page.
Martin, A. R. et al. (2021), "Modeling regional deposition and pharmacokinetics for inhaled prodrug treprostinil palmitil," p. 12 of Abstracts from the International Society for Aerosols in Medicine, 23rd ISAM Congress, Boise, Idaho, May 22-26, 2021, Journal of Aerosol Medicine and Pulmonary Drug Delivery, vol. 34, No. 5, p. A-1-A-22.
Mehta, P. (Jan. 2018), "Imagine the Superiority of Dry Powder Inhalers from Carrier Engineering," Journal of Drug Delivery, vol. 2018, Article ID 5635010, https://doi.org/10.1155/2018/5635010, 20 pages.
Molina, C. et al. (Feb. 2019), "The crucial role of leucine concentration on spray dried mannitol-leucine as a single carrier to enhance the aerosolization performance of Albuterol sulfate," Journal of Drug Delivery Science and Technology, vol. 49, pp. 97-106.
Nguyen, T. L. et al. (2023), "Treprostinil Palmitil Hydrolysis Is Facilitated by Lung Esterases," B59 Breaking Bad: New Drugs and Formulations for Pulmonary Hypertension and RV Failure / Thematic Poster Session / Monday, May 22/09:00 AM-04:15 PM / Walter E. Washington Convention Center, Area B, Hall C (Lower Level), Am J Respir Crit Care Med., 207:A3786, 1 page.
Plaunt, A. J. et al. (2021), "Development and Characterization of Treprostinil Palmitil Inhalation Aerosol for the Investigational Treatment of Pulmonary Arterial Hypertension," Int. J. Mol. Sci., 22, 548. https://doi.org/10.3390/ijms22020548, 17 pages.
Plaunt, A. J. et al. (2022), "Strategies to Overcome Biological Barriers Associated with Pulmonary Drug Delivery," Pharmaceutics, 14, 302. https://doi.org/10.3390/pharmaceutics14020302, 22 pages.
Rattanupatam, T. et al. (Sep. 2014), "Budesonide dry powder for inhalation: effects of leucine and mannitol on the efficiency of delivery," Drug Delivery, 21(6):397-405.
Therapeutics Initiative (Oct. 1995), "Dose Titration: Minimize to Maximize," [Online], Retrieved from the Internet: https://www.ti.ubc.ca/1995/10/31/dose-titration-minimize-to-maximize/, 2 pages.
Adi, H. et al. (2010), "Co-spray-dried mannitol-ciprofloxacin dry powder inhaler formulation for cystic fibrosis and chronic obstructive pulmonary disease, " European Journal of Pharmaceutical Sciences, vol. 40, pp. 239-247.
Atkins, P. J. (Oct. 2005), "Dry Powder Inhalers: An Overview," Conference Proceedings, Respiratory Care, 50(10):1304-1312.
Bard, A. J. (Jan. 1971), "The electrochemistry of organic compounds in aprotic solvents—methods and applications," Pure and Applied Chemistry, vol. 25, Issue 2, pp. 379-393.
Channick, R. N. et al. (2012), "Inhaled treprostinil: a therapeutic review," Drug Design, Development and Therapy :6, p. 19-28.
Chapman, R. W. et al. (Apr. 2018), "Inhaled hexadecyl-treprostinil provides pulmonary vasodilator activity at significantly lower plasma concentrations than infused treprostinil," Pulmonary Pharmacology & Therapeutics, vol. 49, pp. 104-111.
Corboz, M. R. et al. (Dec. 2017), "Preclinical Pharmacology and Pharmacokinetics of Inhaled Hexadecyl-Treprostinil (C16TR), a

(56) References Cited

OTHER PUBLICATIONS

Pulmonary Vasodilator Prodrug," Journal of Pharmacology and Experimental Therapeutics, vol. 363, No. 3, pp. 348-357.
Extended European Search Report for European Application No. 13859435.3, mailed Mar. 29, 2016, 7 pages.
Extended European Search Report for European Application No. 14855785.3, mailed May 22, 2017, 9 pages.
Extended European Search Report for European Application No. 15862092.2, mailed May 25, 2018, 8 pages.
Extended European Search Report for European Application No. 20200798330, dated Jan. 2, 2023, 8 pages.
Extended European Search Report for European Application No. 20213903.6, mailed Mar. 22, 2021, 7 pages.
Extended European Search Report for European Application No. 21164646.8, mailed Jul. 21, 2021, 8 pages.
Flynn, G. L. et al. (Jun. 1972), "Correlation and prediction of mass transport across membranes. I. Influence of alkyl chain length on flux-determining properties of barrier and diffusant," Journal of Pharmaceutical Sciences, vol. 61, No. 6, pp. 838-852.
Hassan, A. et al. (1992), "Medium effect on the second-stage dissociation constant of N-(2-acetamido)imino diacetic acid (H2ADA)," Canadian Journal of Chemistry 70(6):1684-1687.
International Search Report and Written Opinion for International Application No. PCT/US2013/072647, mailed Apr. 4, 2014, 9 pages.
International Search Report and Written Opinion for International Application No. PCT/US2014/062232, mailed Apr. 23, 2015, 11 pages.
International Search Report and Written Opinion for International Application No. PCT/US2015/019661, mailed Jun. 3, 2015, 10 pages.
International Search Report and Written Opinion for International Application No. PCT/US2015/061427, mailed Feb. 2, 2016, 9 pages.
International Search Report and Written Opinion for International Application No. PCT/US2017/038932, mailed Sep. 21, 2017, 10 pages.
International Search Report and Written Opinion for International Application No. PCT/US2020/030282, mailed Aug. 4, 2020, 8 pages.
International Search Report and Written Opinion for International Application No. PCT/US2021/024077, mailed Jul. 28, 2021, 11 pages.
International Search Report and Written Opinion for International Application No. PCT/US2021/057078, mailed Feb. 3, 2022, 17 pages.
Kleemann, E. et al. (Dec. 2006), "Iloprost-containing liposomes for aerosol application in pulmonary arterial hypertension: formulation aspects and stability," Pharmaceutical Research, 24(2):277-287, Feb. 2007, Epub.
Kunishima, M. (2008), "The studies on reaction control and development of new practical reagents based on characteristics of reaction field," The Pharmaceutical Society of Japan, 128(3):425-438 (with English Abstract).
Kuo, Y-C. et al. (2011), "Physicochemical properties of nevirapine-loaded solid lipid nanoparticles and nanostructured lipid carriers," Colloids and Surfaces B: Biointerfaces 83, 299-306.
Lehofer, B., Master's Thesis, (Feb. 2013), "Investigation of liposomal formulations suitable for pulmonary application of iloprost with different nebulizer devices," Graz University of Technology, [Online], Retrieved from the Internet: URL: http://diglib.tugraz.at/download.php?id=576a742a427d7&location=browse, 117 pages.
Leifer, F. et al. (Sep. 2014), "Prolonged activity of inhaled treprostinil prodrug nanoparticles in a rat model of pulmonary arterial hypertension," Poster presented at the European Respiratory Society (ERS) International Congress, Munich, Germany. Retrieved from the Internet: URL: http://www.insmed.com/pdf/3-ProlongedInhaledTreprostinil.pdf. [Retrieved on May 4, 2017], 1 page.
Leifer, F. G. et al. (2018), "Inhaled Treprostinil-Prodrug Lipid Nanoparticle Formulations Provide Long-Acting Pulmonary Vasodilation," Drug Res (Stuttg); 68(11):605-614.
Liu, C. et al. (2017), "Scaling relations for acidity and reactivity of zeolites," J. Phys. Chem., vol. 121, pp. 23520-23530.
Mangal, S. et al. (2018), "Physico-Chemical Properties, Aerosolization and Dissolution of Co-Spray Dried Azithromycin Particles with L-Leucine for Inhalation," Pharmaceutical Research 35:28; 15 pages.
Marakatti, V. S. et al. (2015), "Metal ion-exchanged zeolites as highly active solid acid catalysts for the green synthesis of glycerol carbonate from glycerol," RSC Advances Accepted Manuscript, Issue 19, Retrieved from the Internet: https://pubs.rsc.org/en/content/articlelanding/2015/RA/C4RA16052E#!divAbstract, 34 pages.
Mayo Clinic [online], "Pulmonary Fibrosis, Symptoms and Causes," Retrieved from the Internet on Dec. 15, 2016, URL: http://www.mayoclinic.org/diseases-conditions/pulmonary-fibrosis/symptoms-causes/dxc-20211754, 5 pages.
Mclaughlin, V. V. et al. (2010), "Addition of inhaled treprostinil to oral therapy for pulmonary arterial hypertension," Journal of the American College of Cardiology, 55(18):1915-1922.
Moriarty, R. M. et al. (2004), "The intramolecular asymmetric pauson-khand cyclization as a novel and general stereoselective route to benzindene prostacyclins: synthesis of UT-15 (treprostinil)," J. Org. Chem., 69(6):1890-1902.
Mosgoeller, W. et al. (2012), "Nanoparticle-Mediated Treatment of Pulmonary Arterial Hypertension," Chapter 17 In: Methods in Enzymology, vol. 508, pp. 325-354.
Muller et al., (2000), "Solid lipid nanoparticles (SLN) for controlled drug delivery a review of the state of the art," European Journal of Pharmaceutics and Biopharmaceutics, 50 161-177.
Oberdorster, G. et al. (Jul. 2005), "Nanotoxicology: An emerging discipline evolving from studies of ultrafine particles," Environmental Health Perspectives, vol. 113, No. 7, pp. 823-839.
Poms, A. et al. (2009), "Inhaled Treprostinil for the treatment of Pulmonary Arterial Hypertension," Critical Care Nurse, 31(6):e1-e11.
Provencher, S., (2006), "Long-term treprostinil in pulmonary arterial hypertension: is the glass half full or half empty?," Eur. Respir. J., 28(6):1073-1075.
Pubchem, Compound Summary, "Treprostinil," CID 6918140, Create Date: Jul. 28, 2006, 45 pages.
PubChem Substance of Record for UNII-8GJK87S89F, PubChem CID: 91617675, published online Mar. 18, 2015, pp. 1-8.
Saleemi, S. (Jan.-Mar. 2010), "Portopulmonary hypertension," Ann. Thorac Med., 5(1):5-9.
Shetty, N. et al. (Jun. 2018), "Influence of excipients on physical and aerosolization stability of spray dried high-dose powder formulations for inhalation," Int. J. Pharm, 544(1):222-234.
Shorr, A. F. et al. (2007), "Pulmonary hypertension in patients with pulmonary fibrosis awaiting lung transplant," Eur. Respir. J., vol. 30, pp. 715-721.
Skoro-Sajer, N. et al., (2008), "Treprostinil for pulmonary hypertension," Vascular Health and Risk Management, 4(3):507-513.
Sorbera, L. A. et al., (2001), "UT-15. Treatment of pulmonary hypertension treatment of peripheral vascular disease," Drug of the Future, 26(4):364-374.
Sriwongsitanont, S. et al., (May 2004), "Effect of PEG Lipid (DSPE-PEG2000) and freeze-thawing process on the phospholipid vesicle size and lamellarity," Colloid Polymer Science, vol. 282, No. 7, pp. 753-760; published online Dec. 3, 2003.
Strickley, R. G., (Feb. 2004), "Solubilizing Excipients in Oral and Injectable Formulations," Pharmaceutical Research, vol. 21, No. 2, pp. 201-230.
Vieira, D. B. et al., (2006), "Assembly of a model hydrophobic drug into cationic bilayer fragments," Journal of Colloid and Interface Science, vol. 293, pp. 240-247.
Extended European Search Report for European Application No. 21774190.9 mailed Apr. 4, 2024, 7 pages.
TYVASO DPI (Treprostinil) Inhalation Powder, Highlights of Prescribing Information, Nov. 2023, 17 pages.
TYVASO (Treprostinil) Inhalation Solution, Highlights of Prescribing Information, May 2022, 16 pages.

(56) References Cited

OTHER PUBLICATIONS

International Search Report and Written Opinion for International Application No. PCT/US2024/020472, mailed Jun. 28, 2024, 13 pages.

LeVarge, B. (Mar. 2015), "Prostanoid therapies in the management of pulmonary arterial hypertension," Ther Clin Risk Manag., vol. 11, pp. 535-547. doi: 10.2147/TCRM.S75122. eCollection 2015.

Kumar, P. et al. (2016), "A Comprehensive Review of Treprostinil Pharmacokinetics via Four Routes of Administration," Clin Pharmacokinet., vol. 55, No. 12, pp. 1495-1505.

Inlet T=150, SD-NNP-167

Inlet T=135, SD-NNP-170

Inlet T=120, SD-NNP-171

SD-NNP-170, Inlet T=135°C, no ABC

SD-NNP-173, Inlet T=135°C, 0.5 mg/mL of ABC

SD-NNP-163, 30% leucine

SD-NNP-162, 20% leucine

SD-NNP-112

SD-NNP-111

SD-NNP-P143

T0, SD-NNP-183

T3, SD-NNP-183

DRY POWDER COMPOSITIONS OF TREPROSTINIL PRODRUGS AND METHODS OF USE THEREOF

CROSS REFERENCE TO RELATED APPLICATION

This application is a continuation of U.S. patent application Ser. No. 17/893,991, filed Aug. 23, 2022, now U.S. Pat. No. 11,759,425, which is a continuation of U.S. application Ser. No. 16/860,428, filed Apr. 28, 2020, now U.S. Pat. No. 11,458,098, which claims priority from U.S. Provisional Application Ser. No. 62/840,186, filed Apr. 29, 2019, the disclosure of each of which is incorporated by reference herein in its entirety.

BACKGROUND OF THE INVENTION

Pulmonary hypertension (PH) is characterized by an abnormally high blood pressure in the lung vasculature. It is a progressive, lethal disease that leads to heart failure and can occur in the pulmonary artery, pulmonary vein, or pulmonary capillaries. Symptomatically patients experience shortness of breath, dizziness, fainting, and other symptoms, all of which are made worse by exertion. There are multiple causes, and can be of unknown origin, idiopathic, and can lead to hypertension in other systems, for example, portopulmonary hypertension in which patients have both portal and pulmonary hypertension.

Pulmonary hypertension has been classified into five groups by the World Health Organization (WHO). Group 1 is called pulmonary arterial hypertension (PAH), and includes PAH that has no known cause (idiopathic), inherited PAH (i.e., familial PAH or FPAH), PAH that is caused by drugs or toxins, and PAH caused by conditions such as connective tissue diseases, HIV infection, liver disease, and congenital heart disease. Group 2 pulmonary hypertension is characterized as pulmonary hypertension associated with left heart disease. Group 3 pulmonary hypertension is characterized as PH associated with lung diseases, such as chronic obstructive pulmonary disease and interstitial lung diseases, as well as PH associated with sleep-related breathing disorders (e.g., sleep apnea). Group 4 PH is PH due to chronic thrombotic and/or embolic disease, e.g., PH caused by blood clots in the lungs or blood clotting disorders. Group 5 includes PH caused by other disorders or conditions, e.g., blood disorders (e.g., polycythemia vera, essential thrombocythemia), systemic disorders (e.g., sarcoidosis, vasculitis), and metabolic disorders (e.g., thyroid disease, glycogen storage disease).

Pulmonary arterial hypertension (PAH) afflicts approximately 200,000 people globally with approximately 30,000-40,000 of those patients in the United States. PAH patients experience constriction of pulmonary arteries which leads to high pulmonary arterial pressures, making it difficult for the heart to pump blood to the lungs. Patients suffer from shortness of breath and fatigue which often severely limits the ability to perform physical activity.

The New York Heart Association (NYHA) has categorized PAH patients into four functional classes to rate the severity of the disease. Class I PAH patients as categorized by the NYHA do not have a limitation of physical activity, as ordinary physical activity does not cause undue dyspnoea or fatigue, chest pain, or near syncope. Class II PAH patients as categorized by the NYHA have a slight limitation on physical activity. These patients are comfortable at rest, but ordinary physical activity causes undue dyspnoea or fatigue, chest pain or near syncope. Class III PAH patients as categorized by the NYHA have a marked limitation of physical activity. Although comfortable at rest, class III PAH patients experience undue dyspnoea or fatigue, chest pain or near syncope as a result of less than ordinary physical activity. Class IV PAH patients as categorized by the NYHA are unable to carry out any physical activity without symptoms. Class IV PAH patients might experience dyspnoea and/or fatigue at rest, and discomfort is increased by any physical activity. Signs of right heart failure are often manifested by class IV PAH patients.

Patients with PAH are treated with an endothelin receptor antagonist (ERA), phosphodiesterase type 5 (PDE-5) inhibitor, a guanylate cyclase stimulator, a prostanoid (e.g., prostacyclin), or a combination thereof. ERAs include abrisentan (Letairis®), sitaxentan, bosentan (Tracleer®), and macitentan (Opsumit®). PDE-5 inhibitors indicated for the treatment of PAH include sildenafil (Revatio®) and tadalafil (Adcirca®). Prostanoids indicated for the treatment of PAH include iloprost, epoprosentol and treprostinil (Remodulin®, Tyvaso®). The one approved guanylate cyclase stimulator is riociguat (Adempas®). Additionally, patients are often treated with combinations of the aforementioned compounds.

Portopulmonary hypertension (PPH) is defined by the coexistence of portal and pulmonary hypertension, and is a serious complication of liver disease. The diagnosis of portopulmonary hypertension is based on hemodynamic criteria: (1) portal hypertension and/or liver disease (clinical diagnosis-ascites/varices/splenomegaly), (2) mean pulmonary artery pressure >25 mmHg at rest, (3) pulmonary vascular resistance >240 dynes s/cm$^5$, (4) pulmonary artery occlusion pressure <15 mmHg or transpulmonary gradient >12 mmHg. PPH is a serious complication of liver disease, and is present in 0.25 to 4% of patients suffering from cirrhosis. Today, PPH is comorbid in 4-6% of those referred for a liver transplant.

Pulmonary fibrosis is a respiratory disease in which scars are formed in the lung tissues, leading to serious breathing problems. Scar formation, i.e., the accumulation of excess fibrous connective tissue, leads to thickening of the walls, and causes reduced oxygen supply in the blood. As a result, pulmonary fibrosis patients suffer from perpetual shortness of breath. In some patients the specific cause of the disease can be diagnosed, but in others the probable cause cannot be determined, a condition called idiopathic pulmonary fibrosis.

The present invention addresses the need for novel treatment options for pulmonary hypertension (PH) (including pulmonary arterial hypertension (PAH)), portopulmonary hypertension (PPH), and pulmonary fibrosis by providing dry powder compositions of treprostinil prodrugs useful for pulmonary administration, and methods for administering the same to patients in need of treatment.

SUMMARY OF THE INVENTION

In one aspect, the present disclosure relates to a dry powder composition. The dry powder composition includes (a) from about 0.1 wt % to about 3 wt % of a compound of Formula (I):

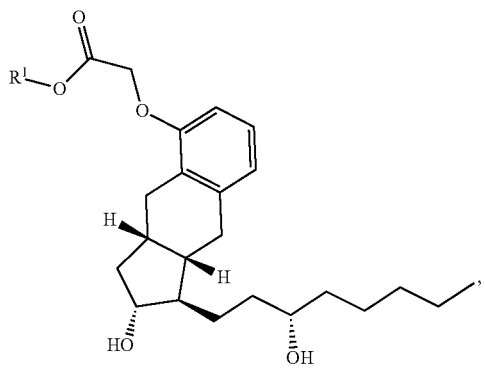

(I)

or an enantiomer, diastereomer, or a pharmaceutically acceptable salt thereof, wherein $R^1$ is tetradecyl, pentadecyl, hexadecyl, heptadecyl, or octadecyl; (b) from about 0.01 wt % to about 3 wt % of distearoylphosphatidylethanolamine-polyethylene glycol 2000 (DSPE-PEG2000), (c) from about 10 wt % to about 50 wt % of leucine, and the balance being (d) a sugar selected from the group consisting of trehalose and mannitol. The entirety of (a), (b), (c), and (d) is 100 wt %.

In one embodiment, $R^1$ is tetradecyl. In a further embodiment, $R^1$ is linear tetradecyl.

In one embodiment, $R^1$ is pentadecyl. In a further embodiment, $R^1$ is linear pentadecyl.

In one embodiment, $R^1$ is heptadecyl. In a further embodiment, $R^1$ is linear heptadecyl.

In one embodiment, $R^1$ is octadecyl. In a further embodiment, $R^1$ is linear octadecyl.

In one embodiment, $R^1$ is hexadecyl. In a further embodiment, $R^1$ is linear hexadecyl.

In one embodiment, the compound of Formula (I), or an enantiomer, diastereomer, or a pharmaceutically acceptable salt thereof, is present at from about 0.5 wt % to about 2 wt % of the total weight of the dry powder composition, and the DSPE-PEG2000 is present at from about 0.05 wt % to about 2 wt % of the total weight of the dry powder composition. In a further embodiment, $R^1$ is hexadecyl. In even a further embodiment, $R^1$ is linear hexadecyl. In a further embodiment, the DSPE-PEG2000 is present at from about 0.15 wt % to about 1.4 wt % of the total weight of the dry powder composition. In even a further embodiment, the DSPE-PEG2000 is present at from about 0.25 wt % to about 1 wt % of the total weight of the dry powder composition.

In one embodiment, the compound of Formula (I), or an enantiomer, diastereomer, or a pharmaceutically acceptable salt thereof is present at from about 1 wt % to about 2 wt % of the total weight of the dry powder composition, and the DSPE-PEG2000 is present at from about 0.1 wt % to about 2 wt % of the total weight of the dry powder composition. In a further embodiment, $R^1$ is hexadecyl. In even a further embodiment, $R^1$ is linear hexadecyl. In a further embodiment, the DSPE-PEG2000 is present at from about 0.3 wt % to about 1.4 wt % of the total weight of the dry powder composition. In even a further embodiment, the DSPE-PEG2000 is present at from about 0.5 wt % to about 1 wt % of the total weight of the dry powder composition.

In one embodiment, the compound of Formula (I), or an enantiomer, diastereomer, or a pharmaceutically acceptable salt thereof is present at from about 1.2 wt % to about 1.8 wt % of the total weight of the dry powder composition, and the DSPE-PEG2000 is present at from about 0.12 wt % to about 1.8 wt % of the total weight of the dry powder composition. In a further embodiment, $R^1$ is hexadecyl. In even a further embodiment, $R^1$ is linear hexadecyl. In a further embodiment, the DSPE-PEG2000 is present at from about 0.36 wt % to about 1.26 wt % of the total weight of the dry powder composition. In even a further embodiment, the DSPE-PEG2000 is present at from about 0.6 wt % to about 0.9 wt % of the total weight of the dry powder composition.

In one embodiment, the compound of Formula (I), or an enantiomer, diastereomer, or a pharmaceutically acceptable salt thereof is present at from about 1 wt % to about 1.5 wt % of the total weight of the dry powder composition, and the DSPE-PEG2000 is present at from about 0.1 wt % to about 1.5 wt % of the total weight of the dry powder composition. In a further embodiment, $R^1$ is hexadecyl. In even a further embodiment, $R^1$ is linear hexadecyl. In a further embodiment, the DSPE-PEG2000 is present at from about 0.3 wt % to about 1.05 wt % of the total weight of the dry powder composition. In even a further embodiment, the DSPE-PEG2000 is present at from about 0.5 wt % to about 0.75 wt % of the total weight of the dry powder composition.

In one embodiment, the compound of Formula (I), or an enantiomer, diastereomer, or a pharmaceutically acceptable salt thereof is present at from about 1.4 wt % to about 1.6 wt % of the total weight of the dry powder composition, and the DSPE-PEG2000 is present at from about 0.14 wt % to about 1.6 wt % of the total weight of the dry powder composition. In a further embodiment, $R^1$ is hexadecyl. In even a further embodiment, $R^1$ is linear hexadecyl. In a further embodiment, the DSPE-PEG2000 is present at from about 0.42 wt % to about 1.12 wt % of the total weight of the dry powder composition. In even a further embodiment, the DSPE-PEG2000 is present at from about 0.7 wt % to about 0.8 wt % of the total weight of the dry powder composition.

In one embodiment, the compound of Formula (I), or an enantiomer, diastereomer, or a pharmaceutically acceptable salt thereof is present at about 1.5 wt % of the total weight of the dry powder composition, and the DSPE-PEG2000 is present at from about 0.15 wt % to about 1.5 wt % of the total weight of the dry powder composition. In a further embodiment, $R^1$ is hexadecyl. In even a further embodiment, $R^1$ is linear hexadecyl. In a further embodiment, the DSPE-PEG2000 is present at from about 0.45 wt % to about 1.05 wt % of the total weight of the dry powder composition. In even a further embodiment, the DSPE-PEG2000 is present at about 0.75 wt % of the total weight of the dry powder composition.

In one embodiment, the compound of Formula (I), or an enantiomer, diastereomer, or a pharmaceutically acceptable salt thereof is present at from about 0.1 wt % to about 3 wt % of the total weight of the dry powder composition, and the weight ratio of the DSPE-PEG2000 to the compound of Formula (I), or an enantiomer, diastereomer, or a pharmaceutically acceptable salt thereof is in a range of from about 0.1:1 (DSPE-PEG2000: the compound of Formula (I), or an enantiomer, diastereomer, or a pharmaceutically acceptable salt thereof) to about 1:1 (DSPE-PEG2000: the compound of Formula (I), or an enantiomer, diastereomer, or a pharmaceutically acceptable salt thereof). In a further embodiment, $R^1$ is hexadecyl. In even a further embodiment, $R^1$ is linear hexadecyl. In a further embodiment, the compound of Formula (I), or an enantiomer, diastereomer, or a pharmaceutically acceptable salt thereof is present at from about 0.5 wt % to about 2 wt % of the total weight of the dry powder composition. In a further embodiment, the compound of Formula (I), or an enantiomer, diastereomer, or a pharmaceutically acceptable salt thereof is present at from about 1 wt % to about 2 wt % of the total weight of the dry powder composition. In a further embodiment, the compound of Formula (I), or an enantiomer, diastereomer, or a pharmaceutically acceptable salt thereof is present at from about 1.2 wt % to about 1.8 wt % of the total weight of the dry powder composition. In a further embodiment, the compound of Formula (I), or an enantiomer, diastereomer, or a pharmaceutically acceptable salt thereof is present at from about 1 wt % to about 1.5 wt % of the total weight of the dry powder composition. In a further embodiment, the compound of Formula (I), or an enantiomer, diastereomer, or a pharmaceutically acceptable salt thereof is present at from about 1.4 wt % to about 1.6 wt % of the total weight of the dry powder composition. In even a further embodiment, the compound of Formula (I), or an enantiomer, diastereomer, or a pharmaceutically acceptable salt thereof is present at about 1.5 wt % of the total weight of the dry powder composition. In another embodiment, the weight ratio of the DSPE-PEG2000 to the compound of Formula (I), or an enantiomer, diastereomer, or a pharmaceutically acceptable salt thereof is in a range of from about 0.3:1 (DSPE-PEG2000: the compound of Formula (I), or an enantiomer, diastereomer, or a pharmaceutically acceptable salt thereof) to about 0.7:1 (DSPE-PEG2000: the compound of Formula (I), or an enantiomer, diastereomer, or a pharmaceutically acceptable salt thereof). In a further embodiment, the weight ratio of the DSPE-PEG2000 to the compound of Formula (I), or an enantiomer, diastereomer, or a pharmaceutically acceptable salt thereof is about 0.5:1 (DSPE-PEG2000: the compound of Formula (I), or an enantiomer, diastereomer, or a pharmaceutically acceptable salt thereof).

In one embodiment of a dry powder composition provided herein, the leucine is present at from about 15 wt % to about 40 wt % of the total weight of the dry powder composition. In a further embodiment, $R^1$ is hexadecyl. In even a further embodiment, $R^1$ is linear hexadecyl. In another embodiment, the leucine is present at from about 18 wt % to about 33 wt % of the total weight of the dry powder composition. In a further embodiment, $R^1$ is hexadecyl. In even a further embodiment, $R^1$ is linear hexadecyl. In another embodiment, the leucine is present at from about 20 wt % to about 30 wt % of the total weight of the dry powder composition. In a further embodiment, $R^1$ is hexadecyl. In even a further embodiment, $R^1$ is linear hexadecyl. In another embodiment, the leucine is present at from about 25 wt % to about 30 wt % of the total weight of the dry powder composition. In a further embodiment, $R^1$ is hexadecyl. In even a further embodiment, $R^1$ is linear hexadecyl. In another embodiment, the leucine is present at from about 27 wt % to about 30 wt % of the total weight of the dry powder composition. In a further embodiment, $R^1$ is hexadecyl. In even a further embodiment, $R^1$ is linear hexadecyl. In another embodiment, the leucine is present at about 30 wt % of the total weight of the dry powder composition. In a further embodiment, $R^1$ is hexadecyl. In even a further embodiment, $R^1$ is linear hexadecyl.

In one embodiment, the sugar is mannitol. In a further embodiment, $R^1$ is hexadecyl. In a further embodiment, $R^1$ is linear hexadecyl.

In one embodiment, the dry powder composition includes (a) about 1.5 wt % of the compound of Formula (I), or an enantiomer, diastereomer, or a pharmaceutically acceptable salt thereof, (b) about 0.7 wt % of the DSPE-PEG2000, (c) about 29.3 wt % of the leucine, and the balance being (d) mannitol. In a further embodiment, $R^1$ is hexadecyl. In a further embodiment, $R^1$ is linear hexadecyl.

In one embodiment, the dry powder composition includes (a) about 1.5 wt % of the compound of Formula (I), or an enantiomer, diastereomer, or a pharmaceutically acceptable salt thereof, (b) about 0.75 wt % of the DSPE-PEG2000, (c) about 29.30 wt % of the leucine, and (d) about 68.45 wt % of the mannitol. In a further embodiment, $R^1$ is hexadecyl. In a further embodiment, $R^1$ is linear hexadecyl.

In one embodiment, the dry powder composition is in the form of an aerosol having particles with a mass median aerodynamic diameter (MMAD) of from about 1 m to about 3 m, as measured by Next Generation Impactor (NGI). In a further embodiment, the dry powder composition is in the form of an aerosol having particles with an MMAD of from about 1.3 m to about 2.0 m, as measured by NGI. In a further embodiment, $R^1$ is hexadecyl. In a further embodiment, $R^1$ is linear hexadecyl.

In one embodiment, the sugar is mannitol, and the dry powder composition is in the form of an aerosol having particles with an MMAD of from about 1 m to about 3 m, as measured by NGI. In another embodiment, the sugar is mannitol, and the dry powder composition is in the form of an aerosol having particles with an MMAD of from about 1.7 m to about 2.7 m, as measured by NGI. In a further embodiment, $R^1$ is hexadecyl. In a further embodiment, $R^1$ is linear hexadecyl.

In one embodiment, the dry powder composition is in the form of an aerosol having particles with a fine particle fraction (FPF) of from about 30% to about 60%, as measured by NGI. In a further embodiment, $R^1$ is hexadecyl. In a further embodiment, $R^1$ is linear hexadecyl.

In another aspect, the present disclosure relates to a method for treating pulmonary hypertension in a patient in need thereof. The method includes administering an effective amount of the dry powder composition disclosed herein to the lungs of the patient by inhalation via a dry powder inhaler.

The pulmonary hypertension, in one embodiment, is pulmonary arterial hypertension (PAH). The PAH, in one embodiment, is class I PAH, as characterized by the New York Heart Association (NYHA). In another embodiment, the PAH is class II PAH, as characterized by NYHA. In another embodiment, the PAH is class III PAH, as characterized by NYHA. In another embodiment, the PAH is class IV PAH, as characterized by NYHA.

In one embodiment, the pulmonary hypertension is group 1 pulmonary hypertension, as characterized by the World Health Organization (WHO).

In another embodiment, the pulmonary hypertension is group 2 pulmonary hypertension, as characterized by the WHO.

In another embodiment, the pulmonary hypertension is group 3 pulmonary hypertension, as characterized by the WHO.

In another embodiment, the pulmonary hypertension is group 4 pulmonary hypertension, as characterized by the WHO.

In another embodiment, the pulmonary hypertension is group 5 pulmonary hypertension, as characterized by the WHO.

In still another aspect, the present disclosure relates to a method for treating portopulmonary hypertension or pulmonary fibrosis in a patient in need thereof. The method includes administering an effective amount of the dry powder composition disclosed herein to the lungs of the patient by inhalation via a dry powder inhaler.

In one embodiment of the treatment methods described herein, the administering is conducted in a once-a-day, twice-a-day, or three-times-a-day dosing.

In another embodiment of the treatment methods described herein, the administering includes aerosolizing the dry powder composition and administering an aerosolized dry powder composition to the lungs of the patient via inhalation. In one embodiment, the aerosolized dry powder composition includes particles with an MMAD of from about 1 µm to about 3 µm, as measured by NGI. In another embodiment, the aerosolized dry powder composition includes particles with an FPF of from about 30% to about 60%, as measured by NGI.

In still another aspect, the present disclosure relates to a system for treating pulmonary hypertension, portopulmonary hypertension, or pulmonary fibrosis. The system includes one of the dry powder compositions disclosed herein and a dry powder inhaler (DPI).

The DPI, in one embodiment, is either a single dose or a multidose inhaler.

In another embodiment, the DPI is pre-metered or device-metered.

DETAILED DESCRIPTION OF THE INVENTION

Figure 1:
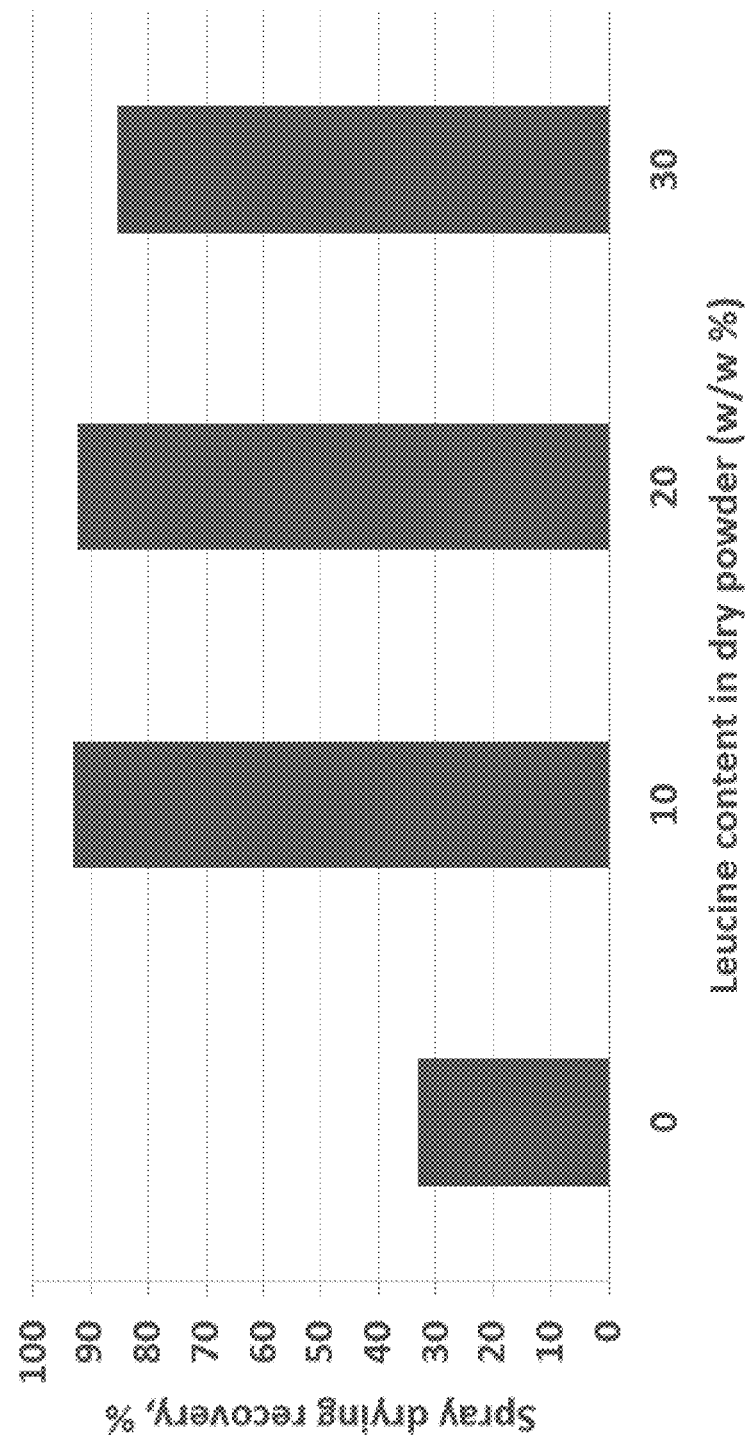
FIG. 1 is a graph showing the effect of leucine content on spray drying recovery of mannitol-based C16TR (treprostinil palmitil) dry powders.

Throughout the present disclosure, the term "about" may be used in conjunction with numerical values and/or ranges. The term "about" is understood to mean those values near to a recited value. For example, "about 40 [units]" may mean within +25% of 40 (e.g., from 30 to 50), within ±20%, ±15%±, 10%, ±9%, ±8%, ±7%, ±6%, ±5%, ±4%, ±3%, ±2%, ±1%, less than ±1%, or any other value or range of values therein or there below.

The term "pharmaceutically acceptable salt" refers to salts prepared from pharmaceutically acceptable non-toxic bases or acids including inorganic or organic bases and inorganic or organic acids. The nature of the salt is not critical, provided that it is pharmaceutically acceptable. Suitable pharmaceutically acceptable acid addition salts may be prepared from an inorganic acid or from an organic acid. Exemplary pharmaceutical salts are disclosed in Stahl, P. H., Wermuth, C. G., Eds. *Handbook of Pharmaceutical Salts: Properties, Selection and Use*; Verlag Helvetica Chimica Acta/Wiley-VCH: Zurich, 2002, the contents of which are hereby incorporated by reference in their entirety. Specific non-limiting examples of inorganic acids are hydrochloric, hydrobromic, hydroiodic, nitric, carbonic, sulfuric and phosphoric acid. Appropriate organic acids include, without limitation, aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric or galacturonic acid. Suitable pharmaceutically acceptable salts of free acid-containing compounds disclosed herein include, without limitation, metallic salts and organic salts. Exemplary metallic salts include, but are not limited to, appropriate alkali metal (group Ia) salts, alkaline earth metal (group IIa) salts, and other physiological acceptable metals. Such salts can be made from aluminum, calcium, lithium, magnesium, potassium, sodium and zinc.

Exemplary organic salts can be made from primary amines, secondary amines, tertiary amines and quaternary ammonium salts, for example, tromethamine, diethylamine, tetra-N-methylammonium, N,N'-dibenzylethylenediamine, chloroprocaine, choline, diethanolamine, ethylenediamine, meglumine (N-methylglucamine) and procaine.

Throughout the present specification, numerical ranges are provided for certain quantities. It is to be understood that these ranges comprise all subranges therein. Thus, the range "50-80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "treating" in one embodiment, includes: (1) preventing or delaying the appearance of clinical symptoms of the state, disorder or condition developing in the subject that may be afflicted with or predisposed to the state, disorder or condition but does not yet experience or display clinical or subclinical symptoms of the state, disorder or condition; (2) inhibiting the state, disorder or condition (e.g., arresting, reducing or delaying the development of the disease, or a relapse thereof in case of maintenance treatment, of at least one clinical or subclinical symptom thereof); and/or (3) relieving the condition (e.g., causing regression of the state, disorder or condition or at least one of its clinical or subclinical symptoms). In one embodiment, "treating" refers to inhibiting the state, disorder or condition (e.g., arresting, reducing or delaying the development of the disease, or a relapse thereof in case of maintenance treatment, of at least one clinical or subclinical symptom thereof). In another embodiment, "treating" refers to relieving the condition (for example, by causing regression of the state, disorder or condition or at least one of its clinical or subclinical symptoms). The benefit to a subject to be treated is either statistically significant as compared to the state or condition of the same subject before the treatment, or as compared to the state or condition of an untreated control subject, or the benefit is at least perceptible to the subject or to the physician.

"Effective amount" means an amount of a dry powder composition of the present disclosure that is sufficient to result in the desired therapeutic response.

In one aspect of the present invention, a dry powder composition of a treprostinil prodrug is provided. The dry powder composition includes:
(a) a compound of Formula (I):

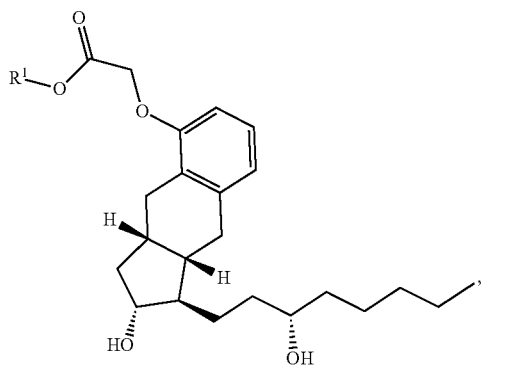

or an enantiomer, diastereomer, or a pharmaceutically acceptable salt thereof, wherein $R^1$ is tetradecyl, pentadecyl, hexadecyl, heptadecyl, or octadecyl, and the compound of Formula (I), or an enantiomer, diastereomer, or a pharmaceutically acceptable salt thereof is present at from about 0.1 wt % to about 3 wt % of the total weight of the dry powder composition;
(b) from about 0.01 wt % to about 3 wt % of DSPE-PEG2000,
(c) from about 10 wt % to about 50 wt % of leucine, and the balance being
(d) a sugar selected from the group consisting of trehalose and mannitol. The entirety of (a), (b), (c), and (d) is 100 wt %.

In some embodiments, the compound of Formula (I), or an enantiomer, diastereomer, or a pharmaceutically acceptable salt thereof is present at about 0.1 wt %, about 0.3 wt %, about 0.5 wt %, about 0.7 wt %, about 1 wt %, about 1.3 wt %, about 1.5 wt %, about 1.7 wt %, about 2.0 wt %, about 2.3 wt %, about 2.5 wt %, about 2.7 wt %, or about 3 wt % of the total weight of the dry powder composition. In a further embodiment, the compound of Formula (I), or an enantiomer, diastereomer, or a pharmaceutically acceptable salt thereof is present at about 1.5 wt % of the total weight of the dry powder composition. The compound of Formula (I) and pharmaceutically acceptable salts thereof are treprostinil prodrugs as disclosed in International Application Publication WO 2015/061720, the disclosure of which is incorporated herein by reference in its entirety. In some embodiments, the leucine is present at about 10 wt %, about 15 wt %, about 20 wt %, about 25 wt %, about 30 wt %, about 35 wt %, about 40 wt %, about 45 wt %, or about 50 wt % of the total weight of the dry powder composition.

PEG refers to polyethylene glycol, also known as polyethylene oxide (PEO) or polyoxyethylene (POE), depending on its molecular weight. The DSPE-PEG2000 may include a branched or unbranched PEG molecule with an average PEG molecular weight of 2000 g/mol. In one embodiment, (b) is DSPE-PEG2000 present at from about 0.03 wt % to about 2.1 wt % of the total weight of the dry powder composition. In another embodiment, (b) is DSPE-PEG2000 present at from about 0.05 wt % to about 1.5 wt % of the total weight of the dry powder composition.

In one embodiment of the compound of Formula (I), or an enantiomer, diastereomer, or a pharmaceutically acceptable salt thereof, $R^1$ is tetradecyl. In a further embodiment, $R^1$ is linear tetradecyl.

In another embodiment of the compound of Formula (I), or an enantiomer, diastereomer, or a pharmaceutically acceptable salt thereof, $R^1$ is pentadecyl. In a further embodiment, $R^1$ is linear pentadecyl.

In another embodiment of the compound of Formula (I), or an enantiomer, diastereomer, or a pharmaceutically acceptable salt thereof, $R^1$ is heptadecyl. In a further embodiment, $R^1$ is linear heptadecyl.

In another embodiment of the compound of Formula (I), or an enantiomer, diastereomer, or a pharmaceutically acceptable salt thereof, $R^1$ is octadecyl. In a further embodiment, $R^1$ is linear octadecyl.

In another embodiment of the compound of Formula (I), or an enantiomer, diastereomer, or a pharmaceutically acceptable salt thereof, $R^1$ is hexadecyl. In a further embodiment, $R^1$ is linear hexadecyl, i.e., the compound of Formula (I), or an enantiomer, diastereomer, or a pharmaceutically acceptable salt thereof, is a compound of Formula (II):

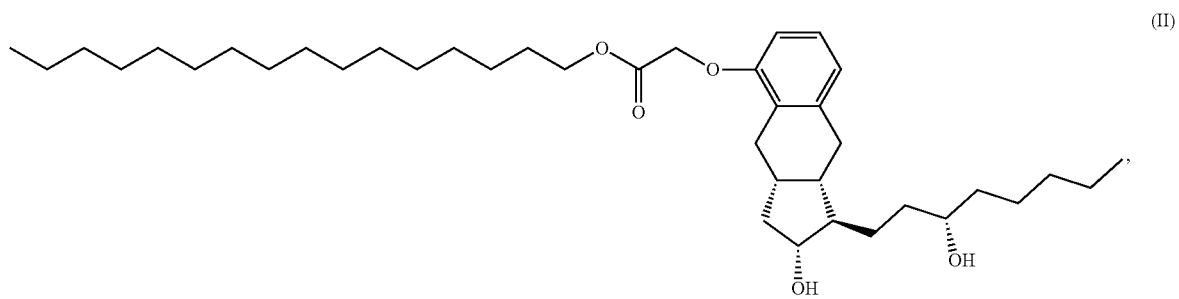 [SMILES: CCCCCCCCCCCCCCCCOC(=O)COc1cccc2c1C[C@H]1C[C@@H](O)[C@H](CC[C@@H](O)CCCCC)[C@H]1C2]

or an enantiomer, diastereomer, or a pharmaceutically acceptable salt thereof. In one embodiment, the compound of Formula (I) or a pharmaceutically acceptable salt thereof is a compound of Formula (II) or a pharmaceutically acceptable salt thereof. In a further embodiment, the compound of Formula (I) or a pharmaceutically acceptable salt thereof is a compound of Formula (II). In a further embodiment, the compound of Formula (I) is a compound of Formula (II). The compound of Formula (II) is also referred to herein as C16TR or treprostinil palmitil. In the present application, C16TR and treprostinil palmitil are used interchangeably and refer to the compound of Formula (II).

In one embodiment, (a) is a compound of Formula (I) or a pharmaceutically acceptable salt thereof. In a further embodiment, (a) is a compound of Formula (I). In another embodiment, (a) is a compound of Formula (II) or a pharmaceutically acceptable salt thereof. In a further embodiment, (a) is a compound of Formula (II).

In one embodiment, the compound of Formula (I) or (II), or an enantiomer, diastereomer, or a pharmaceutically acceptable salt thereof is present at from about 0.5 wt % to about 2 wt % of the total weight of the dry powder composition, and the DSPE-PEG2000 is present at from about 0.05 wt % to about 2 wt % of the total weight of the dry powder composition. In a further embodiment, the DSPE-PEG2000 is present at from about 0.15 wt % to about 1.4 wt % of the total weight of the dry powder composition. In a further embodiment, the DSPE-PEG2000 is present at from about 0.25 wt % to about 1 wt % of the total weight of the dry powder composition. In some embodiments, the compound of Formula (I) or (II), or a pharmaceutically acceptable salt thereof is present at from about 0.5 wt % to about 2 wt % of the total weight of the dry powder composition. In some embodiments, the compound of Formula (I) or (II) is present at from about 0.5 wt % to about 2 wt % of the total weight of the dry powder composition.

In one embodiment, the compound of Formula (I) or (II), or an enantiomer, diastereomer, or a pharmaceutically acceptable salt thereof is present at from about 1 wt % to about 2 wt % of the total weight of the dry powder composition, and the DSPE-PEG2000 is present at from about 0.1 wt % to about 2 wt % of the total weight of the dry powder composition. In a further embodiment, the DSPE-PEG2000 is present at from about 0.3 wt % to about 1.4 wt % of the total weight of the dry powder composition. In a further embodiment, the DSPE-PEG2000 is present at from about 0.5 wt % to about 1 wt % of the total weight of the dry powder composition. In some embodiments, the compound of Formula (I) or (II), or a pharmaceutically acceptable salt thereof is present at from about 1 wt % to about 2 wt % of the total weight of the dry powder composition. In some embodiments, the compound of Formula (I) or (II) is present at from about 1 wt % to about 2 wt % of the total weight of the dry powder composition.

In one embodiment, the compound of Formula (I) or (II), or an enantiomer, diastereomer, or a pharmaceutically acceptable salt thereof is present at from about 1.2 wt % to about 1.8 wt % of the total weight of the dry powder composition, and the DSPE-PEG2000 is present at from about 0.12 wt % to about 1.8 wt % of the total weight of the dry powder composition. In a further embodiment, the DSPE-PEG2000 is present at from about 0.36 wt % to about 1.26 wt % of the total weight of the dry powder composition. In a further embodiment, the DSPE-PEG2000 is present at from about 0.6 wt % to about 0.9 wt % of the total weight of the dry powder composition. In some embodiments, the compound of Formula (I) or (II), or a pharmaceutically acceptable salt thereof is present at from about 1.2 wt % to about 1.8 wt % of the total weight of the dry powder composition. In some embodiments, the compound of Formula (I) or (II) is present at from about 1.2 wt % to about 1.8 wt % of the total weight of the dry powder composition.

In one embodiment, the compound of Formula (I) or (II), or an enantiomer, diastereomer, or a pharmaceutically acceptable salt thereof is present at from about 1 wt % to about 1.5 wt % of the total weight of the dry powder composition, and the DSPE-PEG2000 is present at from about 0.1 wt % to about 1.5 wt % of the total weight of the dry powder composition. In a further embodiment, the DSPE-PEG2000 is present at from about 0.3 wt % to about 1.05 wt % of the total weight of the dry powder composition. In a further embodiment, the DSPE-PEG2000 is present at from about 0.5 wt % to about 0.75 wt % of the total weight of the dry powder composition. In some embodiments, the compound of Formula (I) or (II), or a pharmaceutically acceptable salt thereof is present at from about 1 wt % to about 1.5 wt % of the total weight of the dry powder composition. In some embodiments, the compound of Formula (I) or (II) is present at from about 1 wt % to about 1.5 wt % of the total weight of the dry powder composition.

In one embodiment, the compound of Formula (I) or (II), or an enantiomer, diastereomer, or a pharmaceutically acceptable salt thereof is present at from about 1.4 wt % to about 1.6 wt % of the total weight of the dry powder composition, and the DSPE-PEG2000 is present at from about 0.14 wt % to about 1.6 wt % of the total weight of the dry powder composition. In a further embodiment, the DSPE-PEG2000 is present at from about 0.42 wt % to about 1.12 wt % of the total weight of the dry powder composition. In a further embodiment, the DSPE-PEG2000 is present at from about 0.7 wt % to about 0.8 wt % of the total weight of the dry powder composition. In some embodiments, the compound of Formula (I) or (II), or a pharmaceutically acceptable salt thereof is present at from about 1.4 wt % to about 1.6 wt % of the total weight of the dry powder composition. In some embodiments, the compound of Formula (I) or (II) is present at from about 1.4 wt % to about 1.6 wt % of the total weight of the dry powder composition.

In one embodiment, the compound of Formula (I) or (II), or an enantiomer, diastereomer, or a pharmaceutically acceptable salt thereof is present at about 1 wt % of the total weight of the dry powder composition, and the DSPE-PEG2000 is present at from about 0.1 wt % to about 1 wt % of the total weight of the dry powder composition. In a further embodiment, the DSPE-PEG2000 is present at from about 0.3 wt % to about 0.7 wt % of the total weight of the dry powder composition. In a further embodiment, the DSPE-PEG2000 is present at about 0.5 wt % of the total weight of the dry powder composition. In some embodiments, the compound of Formula (I) or (II), or a pharmaceutically acceptable salt thereof is present at about 1 wt % of the total weight of the dry powder composition. In some embodiments, the compound of Formula (I) or (II) is present at about 1 wt % of the total weight of the dry powder composition.

In one embodiment, the compound of Formula (I) or (II), or an enantiomer, diastereomer, or a pharmaceutically acceptable salt thereof is present at about 1.5 wt % of the total weight of the dry powder composition, and the DSPE-PEG2000 is present at from about 0.15 wt % to about 1.5 wt % of the total weight of the dry powder composition. In a further embodiment, the DSPE-PEG2000 is present at from about 0.45 wt % to about 1.05 wt % of the total weight of the dry powder composition. In a further embodiment, the DSPE-PEG2000 is present at about 0.75 wt % of the total weight of the dry powder composition. In some embodiments, the compound of Formula (I) or (II), or a pharmaceutically acceptable salt thereof is present at about 1.5 wt % of the total weight of the dry powder composition. In some embodiments, the compound of Formula (I) or (II) is present at about 1.5 wt % of the total weight of the dry powder composition.

In some embodiments, the compound of Formula (I) or (II), or an enantiomer, diastereomer, or a pharmaceutically acceptable salt thereof is present at from about 0.1 wt % to about 3 wt %, from about 0.5 wt % to about 2 wt %, from about 1 wt % to about 2 wt %, from about 1.2 wt % to about 1.8 wt %, from about 1 wt % to about 1.5 wt %, from about 1.4 wt % to about 1.6 wt %, about 1 wt %, or about 1.5 wt % of the total weight of the dry powder composition, and the weight ratio of the DSPE-PEG2000 to the compound of Formula (I) or (II), or an enantiomer, diastereomer, or a pharmaceutically acceptable salt thereof is in a range of from about 0.1:1 (DSPE-PEG2000: compound of Formula (I) or (II)) to about 1:1 (DSPE-PEG2000: compound of Formula (I) or (II)), or from about 0.3:1 (DSPE-PEG2000: compound of Formula (I) or (II)) to about 0.7:1 (DSPE-PEG2000: compound of Formula (I) or (II)), e.g., about 0.1:1, about 0.2:1, about 0.3:1, about 0.4:1, about 0.5:1, about 0.6:1, about 0.7:1, about 0.8:1, about 0.9:1, or about 1:1. In one embodiment, the weight ratio of the DSPE-PEG2000 to the compound of Formula (I) or (II), or an enantiomer, diastereomer, or a pharmaceutically acceptable salt thereof is in a range of from about 0.1:1 (DSPE-PEG2000: compound of Formula (I) or (II)) to about 1:1 (DSPE-PEG2000: compound of Formula (I) or (II)). In another embodiment, the weight ratio of the DSPE-PEG2000 to the compound of Formula (I) or (II), or an enantiomer, diastereomer, or a pharmaceutically acceptable salt thereof is in a range of from about 0.3:1 (DSPE-PEG2000: compound of Formula (I) or (II)) to about 0.7:1 (DSPE-PEG2000: compound of Formula (I) or (II)).

In some embodiments, the weight ratio of the DSPE-PEG2000 to the compound of Formula (I) or (II), or an enantiomer, diastereomer, or a pharmaceutically acceptable salt thereof is about 0.5:1 (DSPE-PEG2000: compound of Formula (I) or (II)). At this weight ratio, in one embodiment, the compound of Formula (I) or (II), or an enantiomer, diastereomer, or a pharmaceutically acceptable salt thereof is present at from about 1 wt % to about 2 wt % of the total weight of the dry powder composition, and the DSPE-PEG2000 is present at from about 0.5 wt % to about 1 wt % of the total weight of the dry powder composition. In another embodiment, the compound of Formula (I) or (II), or an enantiomer, diastereomer, or a pharmaceutically acceptable salt thereof is present at from about 1.2 wt % to about 1.8 wt % of the total weight of the dry powder composition, and the DSPE-PEG2000 is present at from about 0.6 wt % to about 0.9 wt % of the total weight of the dry powder composition. In another embodiment, the compound of Formula (I) or (II), or an enantiomer, diastereomer, or a pharmaceutically acceptable salt thereof is present at from about 1.4 wt % to about 1.6 wt % of the total weight of the dry powder composition, and the DSPE-PEG2000 is present at from about 0.7 wt % to about 0.8 wt % of the total weight of the dry powder composition. In another embodiment, the compound of Formula (I) or (II), or an enantiomer, diastereomer, or a pharmaceutically acceptable salt thereof is present at about 1.5 wt % of the total weight of the dry powder composition, and the DSPE-PEG2000 is present at about 0.75 wt % of the total weight of the dry powder composition. In some embodiments, the compound of Formula (I) or (II), or a pharmaceutically acceptable salt thereof is present at each of the above-mentioned weight percentages or weight percentage ranges in the dry powder composition. In some embodiments, the compound of Formula (I) or (II) is present at each of the above-mentioned weight percentages or weight percentage ranges in the dry powder composition.

In one embodiment, the leucine is present at from about 15 wt % to about 40 wt % of the total weight of the dry powder composition. In a further embodiment, the leucine is present at from about 18 wt % to about 33 wt % of the total weight of the dry powder composition. In a further embodiment, the leucine is present at from about 20 wt % to about 30 wt %, e.g., about 20 wt %, about 25 wt %, or about 30 wt % of the total weight of the dry powder composition. In a further embodiment, the leucine is present at from about 25 wt % to about 30 wt % of the total weight of the dry powder composition. In a further embodiment, the leucine is present at from about 27 wt % to about 30 wt % of the total weight of the dry powder composition. In one embodiment, the leucine is present at about 20 wt % of the total weight of the dry powder composition. In another embodiment, the leucine is present at about 30 wt % of the total weight of the dry powder composition.

In some embodiments, the sugar in the dry powder composition is trehalose. In other embodiments, the sugar in the dry powder composition is mannitol.

In one embodiment, the dry powder composition includes (a) about 1.5 wt % of the compound of Formula (I) or (II), or an enantiomer, diastereomer, or a pharmaceutically acceptable salt thereof, (b) about 0.7 wt % of the DSPE-PEG2000, (c) about 29.3 wt % of the leucine, and the balance being (d) trehalose. In a further embodiment, (a) in the dry powder composition is about 1.5 wt % of the compound of Formula (I) or (II), or a pharmaceutically acceptable salt thereof. In a further embodiment, (a) in the dry powder composition is about 1.5 wt % of the compound of Formula (I) or (II). In some embodiments, $R^1$ is hexadecyl in the compound of Formula (I). In a further embodiment, $R^1$ is linear hexadecyl in the compound of Formula (I), i.e., the compound of Formula (I) is a compound of Formula (II).

In another embodiment, the dry powder composition includes (a) about 1 wt % of the compound of Formula (I) or (II), or an enantiomer, diastereomer, or a pharmaceutically acceptable salt thereof, (b) about 0.5 wt % of the DSPE-PEG2000, (c) about 29.6 wt % of the leucine, and the balance being (d) trehalose. In a further embodiment, (a) in the dry powder composition is about 1 wt % of the compound of Formula (I) or (II), or a pharmaceutically acceptable salt thereof. In a further embodiment, (a) in the dry powder composition is about 1 wt % of the compound of Formula (I) or (II). In some embodiments, $R^1$ is hexadecyl in the compound of Formula (I). In a further embodiment, $R^1$ is linear hexadecyl in the compound of Formula (I), i.e., the compound of Formula (I) is a compound of Formula (II).

In another embodiment, the dry powder composition includes (a) about 1 wt % of the compound of Formula (I) or (II), or an enantiomer, diastereomer, or a pharmaceutically acceptable salt thereof, (b) about 0.5 wt % of the DSPE-PEG2000, (c) about 19.7 wt % of the leucine, and the balance being (d) trehalose. In a further embodiment, (a) in the dry powder composition is about 1 wt % of the compound of Formula (I) or (II), or a pharmaceutically acceptable salt thereof. In a further embodiment, (a) in the dry powder composition is about 1 wt % of the compound of Formula (I) or (II). In some embodiments, $R^1$ is hexadecyl in the compound of Formula (I). In a further embodiment, $R^1$ is linear hexadecyl in the compound of Formula (I), i.e., the compound of Formula (I) is a compound of Formula (II).

In another embodiment, the dry powder composition includes (a) about 1.5 wt % of the compound of Formula (I) or (II), or an enantiomer, diastereomer, or a pharmaceutically acceptable salt thereof, (b) about 0.7 wt % of the DSPE-PEG2000, (c) about 19.6 wt % of the leucine, and the balance being (d) trehalose. In a further embodiment, (a) in the dry powder composition is about 1.5 wt % of the compound of Formula (I) or (II), or a pharmaceutically acceptable salt thereof. In a further embodiment, (a) in the dry powder composition is about 1.5 wt % of the compound of Formula (I) or (II). In some embodiments, $R^1$ is hexadecyl in the compound of Formula (I). In a further embodiment, $R^1$ is linear hexadecyl in the compound of Formula (I), i.e., the compound of Formula (I) is a compound of Formula (II).

In another embodiment, the dry powder composition includes (a) about 1.5 wt % of the compound of Formula (I) or (II), or an enantiomer, diastereomer, or a pharmaceutically acceptable salt thereof, (b) about 0.7 wt % of the DSPE-PEG2000, (c) about 29.3 wt % of the leucine, and the balance being (d) mannitol. In a further embodiment, (a) in the dry powder composition is about 1.5 wt % of the compound of Formula (I) or (II), or a pharmaceutically acceptable salt thereof. In a further embodiment, (a) in the dry powder composition is about 1.5 wt % of the compound of Formula (I) or (II). In some embodiments, $R^1$ is hexadecyl in the compound of Formula (I). In a further embodiment, $R^1$ is linear hexadecyl in the compound of Formula (I), i.e., the compound of Formula (I) is a compound of Formula (II).

In another embodiment, the dry powder composition includes (a) about 1.5 wt % of the compound of Formula (I) or (II), or an enantiomer, diastereomer, or a pharmaceutically acceptable salt thereof, (b) about 0.75 wt % of the DSPE-PEG2000, (c) about 29.30 wt % of the leucine, and (d) about 68.45 wt % of the mannitol. In a further embodiment, (a) in the dry powder composition is about 1.5 wt % of the compound of Formula (I) or (II), or a pharmaceutically acceptable salt thereof. In a further embodiment, (a) in the dry powder composition is about 1.5 wt % of the compound of Formula (I) or (II). In some embodiments, $R^1$ is hexadecyl in the compound of Formula (I). In a further embodiment, $R^1$ is linear hexadecyl in the compound of Formula (I), i.e., the compound of Formula (I) is a compound of Formula (II). In one embodiment, the dry powder composition includes (a) about 1.5 wt % of the compound of Formula (II), (b) about 0.75 wt % of the DSPE-PEG2000, (c) about 29.30 wt % of the leucine, and (d) about 68.45 wt % of the mannitol.

In another embodiment, the dry powder composition includes (a) about 1 wt % of the compound of Formula (I) or (II), or an enantiomer, diastereomer, or a pharmaceutically acceptable salt thereof, (b) about 0.5 wt % of the DSPE-PEG2000, (c) about 29.6 wt % of the leucine, and the balance being (d) mannitol. In a further embodiment, (a) in the dry powder composition is about 1 wt % of the compound of Formula (I) or (II), or a pharmaceutically acceptable salt thereof. In a further embodiment, (a) in the dry powder composition is about 1 wt % of the compound of Formula (I) or (II). In some embodiments, $R^1$ is hexadecyl in the compound of Formula (I). In a further embodiment, $R^1$ is linear hexadecyl in the compound of Formula (I), i.e., the compound of Formula (I) is a compound of Formula (II).

In another embodiment, the dry powder composition includes (a) about 1.5 wt % of the compound of Formula (I) or (II), or an enantiomer, diastereomer, or a pharmaceutically acceptable salt thereof, (b) about 0.7 wt % of the DSPE-PEG2000, (c) about 19.6 wt % of the leucine, and the balance being (d) mannitol. In a further embodiment, (a) in the dry powder composition is about 1.5 wt % of the compound of Formula (I) or (II), or a pharmaceutically acceptable salt thereof. In a further embodiment, (a) in the dry powder composition is about 1.5 wt % of the compound of Formula (I) or (II). In some embodiments, $R^1$ is hexadecyl in the compound of Formula (I). In a further embodiment, $R^1$ is linear hexadecyl in the compound of Formula (I), i.e., the compound of Formula (I) is a compound of Formula (II).

In another embodiment, the dry powder composition includes (a) about 1 wt % of the compound of Formula (I) or (II), or an enantiomer, diastereomer, or a pharmaceutically acceptable salt thereof, (b) about 0.5 wt % of the DSPE-PEG2000, (c) about 19.7 wt % of the leucine, and the balance being (d) mannitol. In a further embodiment, (a) in the dry powder composition is about 1 wt % of the compound of Formula (I) or (II), or a pharmaceutically acceptable salt thereof. In a further embodiment, (a) in the dry powder composition is about 1 wt % of the compound of Formula (I) or (II). In some embodiments, $R^1$ is hexadecyl in the compound of Formula (I). In a further embodiment, $R^1$ is linear hexadecyl in the compound of Formula (I), i.e., the compound of Formula (I) is a compound of Formula (II).

Mass median aerodynamic diameter (MMAD) is the value of aerodynamic diameter for which 50% of the mass in a given aerosol is associated with particles smaller than the median aerodynamic diameter (MAD), and 50% of the mass is associated with particles larger than the MAD. MMAD can be determined by impactor measurements, e.g., the Andersen Cascade Impactor (ACT) or the Next Generation Impactor (NGI). In some embodiments, the dry powder composition is in the form of an aerosol comprising particles with an MMAD of from about 1 μm to about 5 μm, from about 1 μm to about 3 μm, from about 1.3 μm to about 2.0 μm, or from about 1.7 μm to about 2.7 μm, as measured by NGI. In one embodiment, the sugar in the dry powder composition is mannitol. In another embodiment, the sugar in the dry powder composition is trehalose.

In one embodiment, the sugar in the dry powder composition is mannitol, and the dry powder composition is in the form of an aerosol comprising particles with an MMAD of from about 1 μm to about 3 μm, as measured by NGI. In another embodiment, the sugar in the dry powder composition is mannitol, and the dry powder composition is in the form of an aerosol comprising particles with an MMAD of from about 1.7 m to about 2.7 m, as measured by NGI.

"Fine particle fraction" or "FPF" refers to the fraction of an aerosol having a particle size less than 5 μm in diameter, as measured by cascade impaction. FPF is usually expressed as a percentage. FPF has been demonstrated to correlate to the fraction of the powder that is deposited in the lungs of the patient. In some embodiments, the dry powder composition is in the form of an aerosol comprising particles with an FPF of at least 20%, at least 30%, at least 40%, at least 50%, from about 30% to about 60%, from about 35% to about 55%, or from about 40% to about 50%, as measured by NGI. In one embodiment, the sugar in the dry powder composition is mannitol. In another embodiment, the sugar is trehalose.

Tap density of a powder is the ratio of the mass of the powder to the volume occupied by the powder after it has been tapped for a defined period of time. The tap density of a powder represents its random dense packing. Tap density can be determined using the method of USP Bulk Density and Tapped Density, United States Pharmacopeia convention, Rockville, Md., 10th Supplement, 4950-4951, 1999. In some embodiments, the dry powder composition comprises particles having a tap density of from about 0.2 g/ml to about 0.8 g/ml, or from about 0.3 g/ml to about 0.6 g/ml. In one embodiment, the sugar in the dry powder composition is mannitol. In another embodiment, the sugar in the dry powder composition is trehalose.

The dry powder compositions of the present disclosure may be produced from liquid compositions using lyophilization or spray-drying techniques. When lyophilization is used, the lyophilized composition may be milled to obtain the finely divided dry powder containing particles within the desired size range described above. When spray-drying is used, the process is carried out under conditions that result in a finely divided dry powder containing particles within the desired size range described above. Exemplary methods of preparing dry powder forms of pharmaceutical compositions are disclosed in WO 96/32149, WO 97/41833, WO 98/29096, and U.S. Pat. Nos. 5,976,574, 5,985,248, and 6,001,336; the disclosure of each of which is incorporated herein by reference in their entireties. Exemplary spray drying methods are described in U.S. Pat. Nos. 6,848,197 and 8,197,845, the disclosure of each of which is incorporated herein by reference in their entireties.

In some embodiments, the dry powder compositions of the present disclosure are prepared by the following process. Stock solutions of a compound of Formula (I) or (II), or an enantiomer, diastereomer, or a pharmaceutically acceptable salt thereof and the DSPE-PEG2000 are prepared using an organic solvent, such as an alcohol (e.g., 1-propanol). Aqueous stock solutions of a sugar (e.g., mannitol or trehalose) and leucine are also prepared. Afterwards required amounts of the above stock solutions are added to a mixture of water and the organic solvent to form a spray drying feed solution. In the spray drying feed solution, the volume ratio of water to the organic solvent may be from about 3:2 to about 1:1.

Spray drying is initiated by starting the drying gas flow and heating up the drying gas by setting the desired inlet temperature at, for example, from about 120° C. to about 160° C., or from about 135° C. to about 150° C. After the spray dryer outlet temperature reaches a suitable temperature, for example, at from about 55° C. to about 65° C., the liquid skid inlet is set to allow blank solvents to be atomized with the aid of nitrogen into the spray dryer, and the system is allowed to cool and stabilize. Product filter pulsing is initiated and product filter purge flow is set, for example, to 10 to 20 scfh. After the system stabilizes, the liquid skid inlet is switched to the feed solution prepared above and the process is continued till the feed solution runs out. At the point when the feed solution runs out, the liquid skid inlet is switched back to blank solvents which are allowed to spray for from about 5 to about 20 minutes. At this point, powder is collected at the bottom of the product filter. After spraying the blank solvent for from about 5 to about 20 minutes, the system is shut down by shutting down the liquid lines, atomization gas, drying gas heater, drying gas inlet and finally the exhaust.

In one embodiment, the dry powder compositions of the present disclosure are delivered to the lungs of a subject via inhalation using a dry powder inhaler (DPI). In one embodiment, the dry powder inhaler is a single dose dry powder inhaler. A propellant-free device, a DPI delivers dry powder to the lungs of a subject using the subject's inspiration. The unit dose of a dry powder composition used in a DPI device is often a dry powder blister disc of hard capsule.

Exemplary DPI devices suitable for delivering the dry powder compositions of the present disclosure include the devices described in the following paragraphs, as well as the DPIs described in U.S. Pat. Nos. 6,766,799, 7,278,425 and 8,496,002, the disclosure of each of which is herein incorporated by reference in their entireties.

The AIR® inhaler (Alkermes) includes a small, breath-activated system that delivers porous powder from a capsule. The porous particles have an aerodynamic diameter of 1-m. See International Patent Application Publication Nos. WO 99/66903 and WO 00/10541, the disclosure of each of which is incorporated herein by reference in their entireties.

Aerolizer™ (Novartis) is a single dose dry powder inhaler. In this device, dry powder medicament is stored in a capsule and released by piercing the capsule wall with TEFLON-coated steel pins. See U.S. Pat. Nos. 6,488,027 and 3,991,761, the disclosure of each of which is incorporated herein by reference in their entireties.

Bang Olufsen provides a breath actuated inhaler using blister strips with up to sixty doses. The dose is made available only during the inhalation by a novel trigger mechanism. The device is equipped with a dose counter and can be disposed of after all doses have been used. See EP 1522325, the disclosure of which is incorporated herein by reference in its entirety.

Clickhaler® (Innovata PLC) is a large reservoir breath-activated multidose device. See U.S. Pat. No. 5,437,270, the disclosure of which is incorporated herein by reference in its entirety.

DirectHaler™ (Direct-Haler A/S) is a single dose, pre-metered, pre-filled, disposable DPI device made from polypropylene. See U.S. Pat. No. 5,797,392, the disclosure of which is incorporated herein by reference in its entirety.

Diskus™ (GlaxoSmithKline) is a disposable small DPI device that holds up to 60 doses contained in double foil blister strips to provide moisture protection. See GB2242134, the disclosure of which is incorporated herein by reference in its entirety.

Eclipse™ (Aventis) is a breath actuated re-usable capsule device capable of delivering up to 20 mg of a dry power composition. The powder is sucked from the capsule into a vortex chamber where a rotating ball assists in powder disaggregation as a subject inhales. See U.S. Pat. No. 6,230,707 and WO 9503846, the disclosure of each of which is incorporated herein by reference in their entireties.

Flexhaler® is a plastic breath-activated dry powder inhaler and is amenable for use with the dry powder compositions provided herein.

FlowCaps® (Hovione) is a capsule-based, re-fillable, re-usable passive dry-powder inhaler that holds up to 14 capsules. The inhaler itself is moisture-proof See U.S. Pat. No. 5,673,686, the disclosure of which is incorporated herein by reference in its entirety.

Gyrohaler® (Vectura) is a passive disposable DPI containing a strip of blisters. See GB2407042, the disclosure of which is incorporated herein by reference in its entirety.

The HandiHaler® (Boehringer Ingelheim GmbH) is a single dose DPI device. It can deliver up to 30 mg of a dry powder composition in capsules. See International Patent Application Publication No. WO 04/024156, the disclosure of which is incorporated herein by reference in its entirety.

MicroDose DPI (Microdose Technologies) is a small electronic DPI device. It uses piezoelectric vibrator (ultrasonic frequencies) to deaggragate the drug powder in an aluminum blister (single or multiple dose). See U.S. Pat. No. 6,026,809, the disclosure of which is incorporated herein by reference in its entirety.

Nektar Dry Powder Inhaler® (Nektar) is a palm-sized and easy-to-use device. It provides convenient dosing from standard capsules and flow-rate-independent lung deposition.

Nektar Pulmonary Inhaler® (Nektar) efficiently removes powders from the packaging, breaks up the particles and creates an aerosol cloud suitable for deep lung delivery. It enables the aerosolized particles to be transported from the device to the deep lung during a patient's breath, reducing losses in the throat and upper airways. Compressed gas is used to aerosolize the powder. See AU4090599 and U.S. Pat. No. 5,740,794, the disclosure of each of which is incorporated herein by reference in their entireties.

NEXT DPI™ is a device featuring multidose capabilities, moisture protection, and dose counting. The device can be used regardless of orientation (upside down) and doses only when proper aspiratory flow is reached. See EP 1196146, U.S. Pat. No. 6,528,096, WO0178693, and WO0053158, the disclosure of each of which is incorporated herein by reference in their entireties.

Neohaler® is a capsule-based plastic breath-activated dry powder inhaler.

Oriel™ DPI is an active DPI that utilizes a piezoelectric membrane and nonlinear vibrations to aerosolize powder formulations. See International Patent Application Publication No. WO 0168169, the disclosure of which is incorporated herein by reference in its entirety.

RS01 monodose dry powder inhaler developed by Plastiape in Italy features a compact size and a simple and effective perforation system and is suited to both gelatin and HMPC capsules.

Pressair™ is a plastic breath-activated dry powder inhaler.

Pulvinal® inhaler (Chiesi) is a breath-actuated multi-dose (100 doses) dry powder inhaler. The dry powder is stored in a reservoir which is transparent and clearly marked to indicate when the 100th dose has been delivered. See U.S. Pat. No. 5,351,683, the disclosure of which is incorporated herein by reference in its entirety.

The Rotohaler® (GlaxoSmithKline) is a single use device that utilizes capsules. See U.S. Pat. Nos. 5,673,686 and 5,881,721, the disclosure of each of which is incorporated herein by reference in their entireties.

Rexam DPI (Rexam Pharma) is a single dose, reusable device designed for use with capsules. See U.S. Pat. No. 5,651,359 and EP 0707862, the disclosure of each of which is incorporated herein by reference in their entireties.

S2 (Innovata PLC) is a re-useable or disposable single-dose DPI for the delivery of a dry powder composition in high concentrations. Its dispersion mechanism requires minimal patient effort to achieve excellent drug delivery to the patients' lungs. S2 is easy to use and has a passive engine so no battery or power source is required. See AU3320101, the disclosure of which is incorporated herein by reference in its entirety.

SkyeHaler® DPI (SkyePharma) is a multidose device containing up to 300 individual doses in a single-use, or replaceable cartridge. The device is powered by breath and requires no coordination between breathing and actuation. See U.S. Pat. No. 6,182,655 and WO97/20589, the disclosure of each of which is incorporated herein by reference in their entireties.

Taifun® DPI (LAB International) is a multiple-dose (up to 200) DPI device. It is breath actuated and flow rate independent. The device includes a unique moisture-balancing drug reservoir coupled with a volumetric dose metering system for consistent dosing. See U.S. Pat. No. 6,132,394, the disclosure of which is incorporated herein by reference in its entirety.

The TurboHaler® (AstraZeneca) is described in U.S. Pat. No. 5,983,893, the disclosure of which is incorporated herein by reference in its entirety. This DPI device is an inspiratory flow-driven, multi-dose dry-powder inhaler with a multi-dose reservoir that provides up to 200 doses of a dry powder composition and a dose range from a few micrograms to 0.5 mg.

The Twisthaler® (Schering-Plough) is a multiple dose device with a dose counting feature and is capable of 14-200 actuations. A dry powder composition is packaged in a cartridge that contains a desiccant. See U.S. Pat. No. 5,829,434, the disclosure of which is incorporated herein by reference in its entirety.

Ultrahaler® (Aventis) combines accurate dose metering and good dispersion. It is an easy-to-use, discrete, pocket-sized device with a numerical dose counter, dose taken indicator and a lock-out mechanism. The device is capable of delivering up to 20 mg of a dry powder composition. Ultrahaler® is described in U.S. Pat. No. 5,678,538 and WO2004026380, the disclosure of each of which is incorporated herein by reference in their entireties.

Xcelovair™ (Meridica/Pfizer) holds 60 pre-metered, hermetically sealed doses in the range of 5-20 mg. The device provides moisture protection under accelerated conditions of 40° C./75% RH. The dispersion system maximizes the fine particle fraction, delivering up to 50% fine particle mass.

In another aspect, a system comprising (i) one of the dry powder compositions described herein and (ii) a dry powder inhaler (DPI) for administration of the dry powder composition is provided. The DPI includes (a) a reservoir comprising the dry powder composition disclosed herein, and (b) a means for introducing the dry powder composition into the patient via inhalation. The reservoir in one embodiment, comprises the dry powder composition of the present invention in a capsule or in a blister pack. The material for the shell of a capsule can be gelatin, cellulose derivatives, starch, starch derivatives, chitosan, or synthetic plastics. The DPI may be a single dose or a multidose inhaler. In addition, the DPI may be pre-metered or device-metered. In one embodiment, the dry powder inhaler is a single dose dry powder inhaler.

The system in one embodiment, is used for treating pulmonary hypertension, portopulmonary hypertension, or pulmonary fibrosis. The system includes the dry powder composition disclosed herein, i.e., a dry powder composition comprising a compound of Formula (I) or (II), or an enantiomer, diastereomer, or a pharmaceutically acceptable salt thereof, and a DPI. In one embodiment, the dry powder composition comprises a compound of Formula (I) or (II), or a pharmaceutically acceptable salt thereof. In another embodiment, the dry powder composition comprises a compound of Formula (I) or (II). The dry powder inhaler may be one described above, may be a single dose or a multidose inhaler, and/or may be pre-metered or device-metered. In one embodiment, the dry powder inhaler is a single dose dry powder inhaler.

In another aspect of the invention, a method for treating pulmonary hypertension (PH) in a patient in need thereof is provided. The method includes administering an effective amount of the dry powder composition disclosed herein, i.e., a dry powder composition comprising a compound of Formula (I) or (II), or an enantiomer, diastereomer, or a pharmaceutically acceptable salt thereof, to the lungs of the patient by inhalation via a dry powder inhaler. In one embodiment, the dry powder composition comprises a compound of Formula (I) or (II), or a pharmaceutically acceptable salt thereof. In another embodiment, the dry powder composition comprises a compound of Formula (I) or (II). In one embodiment, the administering includes aerosolizing the dry powder composition via a DPI to provide an aerosolized dry powder composition, and administering the aerosolized dry powder composition to the lungs of the patient via inhalation by the DPI. In some embodiments, the aerosolized dry powder composition comprises particles with an MMAD of from about 1 μm to about 10 μm, from about 1 μm to about 7 μm, from about 1 μm to about 5 μm, or from about 1 μm to about 3 μm, as measured by NGI. In one embodiment, the aerosolized dry powder composition comprises particles with an FPF of from about 40% to about 70%, from about 30% to about 60%, or from about 50% to about 60%, as measured by NGI.

The World Health Organization (WHO) has classified PH into five groups. Group 1 PH includes pulmonary arterial hypertension (PAH), idiopathic pulmonary arterial hypertension (IPAH), familial pulmonary arterial hypertension (FPAH), and pulmonary arterial hypertension associated with other diseases (APAH). For example, pulmonary arterial hypertension associated with collagen vascular disease (e.g., scleroderma), congenital shunts between the systemic and pulmonary circulation, portal hypertension and/or HIV infection are included in group 1 PH. Group 2 PH includes pulmonary hypertension associated with left heart disease, e.g., atrial or ventricular disease, or valvular disease (e.g., mitral stenosis). WHO group 3 pulmonary hypertension is characterized as pulmonary hypertension associated with lung diseases, e.g., chronic obstructive pulmonary disease (COPD), interstitial lung disease (ILD), and/or hypoxemia. Group 4 pulmonary hypertension is pulmonary hypertension due to chronic thrombotic and/or embolic disease. Group 4 PH is also referred to as chronic thromboembolic pulmonary hypertension. Group 4 PH patients experience blocked or narrowed blood vessels due to blood clots. Group 5 PH is the "miscellaneous" category, and includes PH caused by blood disorders (e.g., polycythemia vera, essential thrombocythemia), systemic disorders (e.g., sarcoidosis, vasculitis) and/or metabolic disorders (e.g., thyroid disease, glycogen storage disease).

The methods provided herein can be used to treat group 1 (i.e., pulmonary arterial hypertension or PAH), group 2, group 3, group 4 or group 5 PH patients, as characterized by the WHO. In one embodiment of the methods, the pulmonary hypertension treated is chronic thromboembolic pulmonary hypertension.

In another embodiment of the methods, the pulmonary hypertension treated is pulmonary arterial hypertension (PAH). In some embodiments, the PAH treated is class I PAH, class II PAH, class III PAH, or class IV PAH, as characterized by the New York Heart Association (NYHA).

In one embodiment, the PAH is class I PAH, as characterized by the NYHA.

In another embodiment, the PAH is class II PAH, as characterized by the NYHA.

In yet another embodiment, the PAH is class III PAH, as characterized by the NYHA.

In still another embodiment, the PAH is class IV PAH, as characterized by the NYHA.

In another aspect, the present disclosure provides a method for treating portopulmonary hypertension (PPH) in a patient in need thereof. The method includes administering an effective amount of the dry powder composition disclosed herein, i.e., a dry powder composition comprising a compound of Formula (I) or (II), or an enantiomer, diastereomer, or a pharmaceutically acceptable salt thereof, to the lungs of the patient by inhalation via a dry powder inhaler. In one embodiment, the dry powder composition comprises a compound of Formula (I) or (II), or a pharmaceutically acceptable salt thereof. In another embodiment, the dry powder composition comprises a compound of Formula (I) or (II). In one embodiment, the administering includes aerosolizing the dry powder composition with a dry powder inhaler (DPI) to provide an aerosolized dry powder composition, and administering the aerosolized dry powder composition to the lungs of the patient via the DPI. In some embodiments, the aerosolized dry powder composition comprises particles with an MNAD of from about 1 μm to about 10 μm, from about 1 μm to about 7 μm, from about 1 μm to about 5 μm, or from about 1 μm to about 3 μm, as measured by NGI. In one embodiment, the aerosolized dry powder composition comprises particles with an FPF of from about 40% to about 70%, from about 30% to about 60%, or from about 50% to about 60%, as measured by NGI.

In some embodiments, the PH, PAH, or PPH patient treated by the disclosed methods manifests one or more of the following therapeutic responses: (1) a reduction in the pulmonary vascular resistance index (PVRI) from pretreatment value, (2) a reduction in mean pulmonary artery pressure from pretreatment value, (3) an increase in the hypoxemia score from pretreatment value, (4) a decrease in the oxygenation index from pretreatment values, (5) improved right heart function, as compared to pretreatment, and (6) improved exercise capacity (e.g., as measured by the six-minute walk test) compared to pretreatment.

In one embodiment of the disclosed methods, the PH, PAH, or PPH patient is administered the dry powder composition once daily. In another embodiment of the disclosed methods, the PH, PAH, or PPH patient is administered the dry powder composition twice daily. In still another embodiment of the disclosed methods, the PH, PAH, or PPH patient is administered the dry powder composition three or more times daily. In one embodiment, the administration is with food. In one embodiment, each administration comprises 1 to 5 doses (puffs) from a DPI, for example 1 dose (1 puff), 2 doses (2 puffs), 3 doses (3 puffs), 4 doses (4 puffs) or 5 doses (5 puffs). The DPI, in one embodiment, is small and transportable by the patient. In one embodiment, the dry powder inhaler is a single dose dry powder inhaler.

In still another aspect, the present disclosure provides a method for treating pulmonary fibrosis in a patient in need thereof. The method includes administering an effective amount of the dry powder composition disclosed herein, i.e., a dry powder composition comprising a compound of Formula (I) or (II), or an enantiomer, diastereomer, or a pharmaceutically acceptable salt thereof, to the lungs of the patient by inhalation via a dry powder inhaler. In one embodiment, the dry powder composition comprises a compound of Formula (I) or (II), or a pharmaceutically acceptable salt thereof. In another embodiment, the dry powder composition comprises a compound of Formula (I) or (II). In one embodiment, the administering includes aerosolizing the dry powder composition with a DPI to form an aerosolized dry powder composition, and administering the aerosolized dry powder composition to the lungs of the patient via the DPI. In some embodiments, the aerosolized dry powder composition comprises particles with an MMAD of from about 1 μm to about 10 μm, from about 1 μm to about 7 μm, from about 1 μm to about 5 μm, or from about 1 μm to about 3 μm, as measured by NGI. In one embodiment, the aerosolized dry powder composition comprises particles with an FPF of from about 40% to about 70%, from about 30% to about 60%, or from about 50% to about 60%, as measured by NGI.

The patient, in one embodiment, is administered the dry power composition once daily, twice daily, or three or more times daily. In one embodiment, the administration is with food. In one embodiment, each administration comprises 1 to 5 doses (puffs) from a DPI, for example 1 dose (1 puff), 2 doses (2 puffs), 3 doses (3 puffs), 4 doses (4 puffs) or 5 doses (5 puffs). The DPI, in one embodiment, is small and transportable by the patient. In one embodiment, the dry powder inhaler is a single dose dry powder inhaler.

EXAMPLES

The present invention is further illustrated by reference to the following Examples. However, it should be noted that these Examples, like the embodiments described above, are illustrative and are not to be construed as restricting the scope of the invention in any way.

Example 1—Preparation and Characterization of Inhalable Dry Powder Formulations Comprising the Compound of Formula (II) (Treprostinil Palmitil)

This example describes mannitol and trehalose-based dry powder formulations comprising treprostinil palmitil represented by Formula (II), their preparations by spray drying using Buchi B-290 spray dryer equipped with Inert Loop Condenser B-295 and Dehumidifier B-296, and the characterization and stability testing of the formulations.

The mannitol-based treprostinil palmitil dry powder formulations, with components treprostinil palmitil/DSPE-PEG2000/Mannitol/Leucine (1/0.5/80/20, 1.5/0.75/80/20, 2/1/80/20, w/w) were successfully made. The feed stock was made by dissolving all components in 1-propanol/$H_2O$ co-solvent system (50/50, v/v), without the addition of ammonium bicarbonate. The spray drying yields for mannitol-based dry powder were above 90%. The collected dry powder had spherical particles, crystalline XRD profile, and low moisture content.

The trehalose-based treprostinil palmitil dry powder formulations, with components of treprostinil palmitil/DSPE-PEG2000/Trehalose/Leucine (1/0.5/80/20, 1/0.5/70/30, 1.5/0.75/80/20, 2/1/80/20, w/w), were created by spray drying the feed stock containing all components dissolved in 1-propanol/$H_2O$ co-solvent system (50/50, v/v), without the addition of ammonium bicarbonate. The trehalose-based dry powder contained collapsed particles, exhibiting crystalline leucine and amorphous trehalose. Trehalose-based dry powder showed good physical stability over 3 months.

Materials and Methods

1. Materials
   Phosphate buffered saline: PBS, PH 7.4, Cat. No. 10010 (Life technologies), or equivalent
   Sodium chloride: ACS Reagent (JT Baker, Cat. No. 3628-05), or equivalent
   Treprostinil palmitil, Formula II, above
   DSPE-PEG2000: N-(Methylpolyoxyethylene oxycarbonyl)-1,2-distearoyl-sn-glycero-3-phosphoethanolamine, sodium salt, SUNBRIGHT@DSPE-020CN (NOF, Tokyo, Japan), or equivalent
   D-lactose, monohydrate, (Sigma)
   L-leucine, (Sigma)
   Ammonium bicarbonate (Sigma)
   Absolute ethanol (Fisher Sci)
   1-propanol (Fisher Sci)

2. Equipment
   Buchi B-290 Spray Dryer with Inert Loop Condenser B-295, Dehumidifier B-296, Two-fluid nozzle ID 0.7 mm, and high-performance cyclonic separator (Buchi).
   SEM: Zeiss-Sigma FE-SEM (Germany)
   XRD: (PANalytical, Netherlands)
   DSC 250, TA Instruments, New Castle, DE, USA.
   Tapped density tester, JV 1000, (Copley Scientific, UK)
   NGI: Next Generation Impactor, (MSP Corporation, MN, USA)
   PSD: RODOS/M, (Sympatec, Germany)
   Karl Fischer titrator: Aquastar, AQV33, EMD.
   DLS: Mobiu(©, Atlas, (Wyatt Technology, Santa Barbara, CA)
   High Performance Liquid Chromatograph: Waters Alliance Model 2695. HPLC
   software: Waters Empower™ 3
   Magnetic stir plate 3. Preparation of Dry Powder Formulation Comprising Treprostinil Palmitil, DSPE-PEG2000, Trehalose, and Leucine at a Weight Ratio of 1:0.5:80:20

TABLE 1

Formulation details for trehalose-based treprostinil palmitil dry powder

| Excipients | Solvent | Composition treprostinil palmitil/DSPE-PEG2000/ Treh/Leu/ ammonium bicarbonate (ABC) (mg/mL) | Composition treprostinil palmitil/DSPE-PEG2000/ Trehalose/ Leucine Weight Ratio | Feed-Solid (mg/ml) |
|---|---|---|---|---|
| DSPE-PEG2000/ Trehalose/ Leucine | 1-propanol (50% in water, v/v) | 0.2/0.1/16/4/1 | 1/0.5/80/20 | 20.3 |

Preparation of Stock Solutions:
   Treprostinil palmitil: 10 mg/mL in 1-propanol
   DSPE-PEG2000: 10 mg/mL in 1-propanol
   Trehalose: 150 mg/mL in DI water
   Leucine stock: 20 mg/mL in DI water Preparation of Spray Drying Feed Solution:
   According to Table 1, the spray drying feed solution was prepared at a 1:100 weight ratio of treprostinil palmitil to a total of trehalose and leucine. Final feed solution had 50% of 1-propanol and 20.3 mg/mL of solid (Table 2).

Trehalose and leucine stock solutions were added into water phase first, followed by the addition of 1-propanol and sonication in water bath. Then, treprostinil palmitil (Formula (II)) and DSPE-PEG2000 were added separately. Stirring was applied through the whole process.

TABLE 2

Preparation of spray drying stock for trehalose-based dry powder

|  | Treprostinil Palmitil | DSPE-PEG2000 | 1-propanol | Trehalose | Leucine | $H_2O$ |
|---|---|---|---|---|---|---|
| Stock (mg/mL) | 10 | 10 | N/A | 150 | 20 | N/A |
| Weight ratio | 1 | 0.5 | N/A | 80 | 20 | N/A |

TABLE 2-continued

Preparation of spray drying stock for trehalose-based dry powder

|  | Treprostinil Palmitil | DSPE-PEG2000 | 1-propanol | Trehalose | Leucine | H$_2$O |
|---|---|---|---|---|---|---|
| Volume (100 mL) | 2 | 1 | 47 | 10.7 | 20 | 20.3 |
| Conc (mg/mL) | 0.2 | 0.1 | N/A | 16 | 4 | N/A |

Spray Drying Process of Trehalose-Based Dry Powder Containing Treprostinil Palmitil/DSPE-PEG2000/Treh/Leu (1/0.5/80/20):

Spray drying was performed using spray dryer Buchi B-290 under the following parameters: 150° C. inlet temperature, 64° C. outlet temperature, 414 L/h spray air flow (36 mm, height in rotameter), 35% m³/h as aspiration rate, and a feed-rate of 7.5 mL/min (22%). Table 3 summarizes the process parameters.

TABLE 3

Parameters in spray drying process for trehalose-based dry powder

| Inlet T (° C.) | Outlet T (° C.) | Aspiration | Spray gas flow | Feed-rate |
|---|---|---|---|---|
| 150 | 64 | 100% (35 m³/h) | 36 mm (414 L/h) | 22% (7.5 mL/min) |

4. Preparation of Dry Powder Formulation Comprising Treprostinil Palmitil, DSPE-PEG2000, Mannitol, and Leucine at a Weight Ratio of 1:0.5:80:20

TABLE 4

Formulation details for mannitol-based treprostinil palmitil dry powder

| Excipients | Solvent | Composition treprostinil palmitil/DSPE-PEG2000/Man/Leu/ABC (mg/mL) | Composition treprostinil palmitil/DSPE-PEG2000/Man/Leu Weight Ratio | Feed-Solid (mg/ml) |
|---|---|---|---|---|
| DSPE-PEG2000/Mannitol/Leucine | 1-propanol (50% in water, v/v) | 0.2/0.1/16/4 | 1/0.5/80/20 | 20.3 |

Preparation of Stock Solutions:
  Treprostinil palmitil: 10 mg/mL in 1-propanol
  DSPE-PEG2000: 10 mg/mL in 1-propanol
  Mannitol: 150 mg/mL in DI water
  Leucine stock: 20 mg/mL in DI water Preparation of Spray Drying Feed Solution:
  According to Table 4, the spray drying feed solution was prepared at a 1:100 weight ratio of treprostinil palmitil to a total of mannitol and leucine. Final feed solution had 50% of 1-propanol and 20.3 mg/mL of solid (Table 5).

Mannitol and leucine stock solutions were added into water phase first, followed by the addition of propanol and sonication in water bath. Then, treprostinil palmitil and DSPE-PEG2000 were added separately. Stirring was applied through the whole process.

TABLE 5

Preparation of spray drying stock for mannitol-based dry powder

|  | Treprostinil Palmitil | DSPE-PEG2000 | 1-propanol | Mannitol | Leucine | H$_2$O |
|---|---|---|---|---|---|---|
| Stock (mg/mL) | 10 | 10 | N/A | 150 | 20 | N/A |
| Weight Ratio | 1 | 0.5 | N/A | 80 | 20 | N/A |
| Volume (100 mL) | 2 | 1 | 47 | 10.7 | 20 | 20.3 |
| Conc (mg/mL) | 0.2 | 0.1 | N/A | 16 | 4 | N/A |

Spray drying process of mannitol-based dry powder composed of treprostinil palmitil/DSPE-PEG2000/Mannitol/Leu (1/0.5/80/20):

Spray drying was performed using spray dryer Buchi B-290 under the following parameters: 135° C. inlet temperature, 60° C. outlet temperature, 414 L/h spray air flow (36 mm, height in rotameter), 35% $m^3$/h as aspiration rate, and a feed-rate of 7.5 mL/min (22%). Table 6 summarizes the process parameters.

TABLE 6

Parameters in spray drying process for mannitol-based dry powder

| Inlet T (° C.) | Outlet T (° C.) | Aspiration | Spray gas flow | Feed-rate |
|---|---|---|---|---|
| 135 | 60 | 100% (35 $m^3$/h) | 36 mm (414 L/h) | 22% (7.5 mL/min) |

5. Characterization of Dry Powder

Surface Electron Microscopy (SEM)

Dry powder sample (as received) was poured on a carbon tape and then coated with 20 nm gold (Au) using an Electron Microscopy Sciences (EMS150T ES) sputter coater. Field emission-scanning electron microscopy (FE-SEM) was used to observe the particle morphologies using a Zeiss-Sigma FE-SEM (Germany) with an operating voltage of 5 keV. The working distance was kept between 8 to 10 mm to obtain relatively high resolution.

X-Ray Diffraction Test (XRD)

Dry powder sample (as received) was packed in the zero-background sample holder and then X-ray diffraction (XRD) was employed for assessment of the structural characteristics using a PANalytical (Netherlands) X'Pert Diffractometer at 45 kV and 40 mA with Cu Kα (λ=1.540598 Å) radiation at a scanning rate of 0.04 rad degrees per min. The scanning range was between 4° to 400 degrees (2θ) with a time per step of 97.92 seconds and a step size of 0.0131°.

Differential Scanning Calorimetry (DSC)

Around 5-10 mg of dry powder was weighed into DSC sample pan which was then hermetically sealed. Test was performed as follows: equilibrate at 20° C., modulate temperature 0.32° C. for 60 seconds, isothermal 1.0 min, ramp 5° C./min to 180.0° C.

Particle Size Distribution (PSD) by Laser Diffraction

Around 15 mg-20 mg of dry powder was put into the required glass tube. The Sympatech-HOLOS-REDOS mode was used. Test was performed as follows:

| | |
|---|---|
| Measuring range | R1: 0.1/0.18 . . . 35 μm |
| Trigger condition | Rodos standard trigger |
| Disperser | Rodos (RO-AS-15 mm) |
| Disperser type | RODOS/M |
| Injector | 4 mm with 0 cascade elements |
| Primary pressure | 0.5 bar |

Moisture Content Test (Karl Fischer)

The moisture content in dry powder was analyzed using Karl Fischer. Approximately 30 mg of sample was weighed out and transferred to the titration vessel. The equipment, materials and operating parameters were used as described below:

Materials/Equipment:

(1) Titrator: Aquastar AQV33 Karl Fischer Titrator with 5 mL burette installed, with an associated balance (2) Balance: analytical balance capable of weighing up to 4-decimal places with an interface capable to connect to the Aquastar Titrator.

(3) Water Standard 1% NIST (4) Dessicant 100% indicating or Molecular Sieve, Type 4A, 1/16 Pellets (5) Lint free cloth, Kimwipe (6) Weighing boats (7) Syringe 3 mL Solutions:

(1) Titrant: Aquastar CombiTitrant 2

(2) Solvent: 60/40 Methanol/Formamide

Instrument Parameters and Conditions:

(1) Drift: <50 g/min (2) Stir speed: 40%

(3) Mix time: 300 sec (4) Termination: Relative Drift

Bulk and Tap Density

The density test was performed via the tapped density tester, JV 1000 (Coply Scientific, UK). The following procedures were followed. Clean glass tube, dry with compressed air; weigh glass tube, record as W1; transfer dry powder into glass tube, mark the height as A, and record weight as W2; seal the top with parafilm; put the glass tube into a 5 mL graduated cylinder, tapping for 10 min; mark the height as B after tapping; remove powder from tube, clean and dry with compressed air; weight glass tube, record as W3; add water to level B, and record weight as W5; add water to level A, and record weight as W4. (assuming the density of water equals 1 g/mL)

| | |
|---|---|
| Dry powder loading | W2-W1 |
| Volume of bulk density | (W4-W3)/1 g/mL |
| Volume of tap density | (W5-W3)/1 g/mL |
| Bulk density | dry powder loading/volume of bulk density |
| Tap density | dry powder loading/volume of tap density |

Aerodynamic Particle Size Distribution (APSD) Using NGI

Around 20 mg of powder, filled in the size 3 Vcaps HPMC capsule, were dispersed through a commercial inhaler (Plastiape RS01) into a next generation cascade impactor (NGI) (Copley Scientific, UK) operated at a volumetric flow rate of 60 L/min and actuated for 4 seconds. Drug content collected at each stage from the NGI apparatus was assessed by HPLC-MS. Fine particle fraction (FPF) was defined as the drug mass (<5 μm) deposited in the NGI divided by the emitted dose.

HPLC Assay

Treprostinil (TRE) and treprostinil palmitil concentrations were determined using a Waters Alliance Model 2695 equipped with a PDA Detector (Waters 2996) and Corona Charged Aerosol Detector (Thermo Fisher Scientific).

Column: ACE 3 C8 HPLC Column 4.6×50 (Mac-Mod Analytical, Cat. No. ACE1120546)

Column temperature: 25° C.

Mobile phase A: acetonitrile 25%, methanol 25%, water 50%, formic acid 0.1%, triethylamine 0.01%

Mobile phase B: acetonitrile 50%, methanol 50%, formic acid 0.1%, triethylamine 0.01%

Flow rate: 1 mL/min

Gradient to measure TRE:

Injection volume: 50 μL

UV wavelength: 270+2.4 nm

Samples and standards were dissolved in acetonitrile 33%, methanol 33%, water 33%

Calibration was fitted by a power function Log(Area)=A+ B*Log(Conc)

Retention time TRE~1.8 min, C16TR~ 7.6 min

Total recording time 9 min

Results

1. Batches of Mannitol-Based Treprostinil Palmitil Dry Powder

Different batches of mannitol-based treprostinil palmitil dry powders were prepared by spray drying. In those batches, the treprostinil palmitil amount in dry powder varied from 1 to 5 (weight ratio, w/w), while the ratio of treprostinil palmitil to DSPE-PEG2000 was kept the same at 2 to 1. The leucine content ranged between 0 to 30% (w/w) of dry powder. The effect of ammonium bicarbonate was also investigated. During the spray drying process, the inlet temperature varied from 120° C. to 150° C. Table 7A shows the compositions and the inlet temperatures for the different batches of mannitol-based treprostinil palmitil dry powders. For each batch, the amounts of treprostinil palmitil, DSPE-PEG2000, mannitol, and leucine are indicated by weight ratio. The amounts of treprostinil palmitil and leucine are also indicated by their approximate weight percentages represented by their proportions in the weight ratio. Table 7B shows the targeted weight percentages of treprostinil palmitil, DSPE-PEG2000, mannitol, and leucine in each batch calculated based on the weight ratio.

TABLE 7A

Batches of mannitol-based treprostinil palmitil dry powders

| Batch# | Composition treprostinil palmitil/DSPE-PEG2000/Man/Leu Weight Ratio | Approximate wt % of treprostinil palmitil in dry powder | Approximate wt % of leucine in dry powder | Ammonium bicarbonate (mg/mL) | Inlet T (° C.) |
|---|---|---|---|---|---|
| SD-NNP-182 | 1/0.5/100/0 | 1 | 0 | 0 | 120 |
| SD-NNP-181 | 1/0.5/100/0 | 1 | 0 | 0 | 135 |
| SD-NNP-180 | 1/0.5/90/10 | 1 | 10 | 0 | 135 |
| SD-NNP-171 | 1/0.5/80/20 | 1 | 20 | 0 | 120 |
| SD-NNP-175 | 1/0.5/80/20 | 1 | 20 | 0 | 120 |
| SD-NNP-170 | 1/0.5/80/20 | 1 | 20 | 0 | 135 |
| SD-NNP-179 | 1/0.5/80/20 | 1 | 20 | 0 | 135 |
| SD-NNP-174 | 1/0.5/80/20 | 1 | 20 | 0 | 135 |
| SD-NNP-167 | 1/0.5/80/20 | 1 | 20 | 0 | 150 |
| SD-NNP-168 | 1/0/80/20 | 1 | 20 | 0 | 150 |
| SD-NNP-172 | 1/0.5/80/20 | 1 | 20 | 0.5 | 120 |
| SD-NNP-173 | 1/0.5/80/20 | 1 | 20 | 0.5 | 135 |
| SD-NNP-176 | 1/0.5/70/30 | 1 | 30 | 0 | 120 |
| SD-NNP-177 | 1/0.5/70/30 | 1 | 30 | 0 | 135 |
| SD-NNP-183 | 1.5/0.75/80/20 | 1.5 | 20 | 0 | 135 |
| SD-NNP-184 | 2/1.0/80/20 | 2 | 20 | 0 | 135 |
| SD-NNP-190 | 3/1.5/80/20 | 3 | 20 | 0 | 135 |
| SD-NNP-191 | 5/2.5/80/20 | 5 | 20 | 0 | 135 |

TABLE 7B

Amounts of treprostinil palmitil, DSPE-PEG2000, mannitol, and leucine expressed in weight ratios and corresponding targeted weight percentages in batches of mannitol-based treprostinil palmitil dry powders

| Batch# | Composition treprostinil palmitil/DSPE-PEG2000/Man/Leu Weight Ratio | Composition Wt % | | | |
|---|---|---|---|---|---|
| | | Treprostinil Palmitil | DSPE-PEG2000 | Mannitol | Leucine |
| SD-NNP-182 | 1/0.5/100/0 | 0.99 | 0.49 | 98.5 | 0 |
| SD-NNP-181 | 1/0.5/100/0 | 0.99 | 0.49 | 98.5 | 0 |
| SD-NNP-180 | 1/0.5/90/10 | 0.99 | 0.49 | 88.7 | 9.85 |
| SD-NNP-171 | 1/0.5/80/20 | 0.99 | 0.49 | 78.8 | 19.7 |
| SD-NNP-175 | 1/0.5/80/20 | 0.99 | 0.49 | 78.8 | 19.7 |
| SD-NNP-170 | 1/0.5/80/20 | 0.99 | 0.49 | 78.8 | 19.7 |
| SD-NNP-179 | 1/0.5/80/20 | 0.99 | 0.49 | 78.8 | 19.7 |
| SD-NNP-174 | 1/0.5/80/20 | 0.99 | 0.49 | 78.8 | 19.7 |
| SD-NNP-167 | 1/0.5/80/20 | 0.99 | 0.49 | 78.8 | 19.7 |
| SD-NNP-168 | 1/0/80/20 | 0.99 | 0 | 79.2 | 19.8 |
| SD-NNP-172 | 1/0.5/80/20 | 0.99 | 0.49 | 78.8 | 19.7 |
| SD-NNP-173 | 1/0.5/80/20 | 0.99 | 0.49 | 78.8 | 19.7 |
| SD-NNP-176 | 1/0.5/70/30 | 0.99 | 0.49 | 68.9 | 29.6 |
| SD-NNP-177 | 1/0.5/70/30 | 0.99 | 0.49 | 68.9 | 29.6 |
| SD-NNP-183 | 1.5/0.75/80/20 | 1.47 | 0.73 | 78.2 | 19.6 |
| SD-NNP-184 | 2/1.0/80/20 | 1.94 | 0.97 | 77.7 | 19.4 |

TABLE 7B-continued

Amounts of treprostinil palmitil, DSPE-PEG2000, mannitol, and leucine expressed in weight ratios and corresponding targeted weight percentages in batches of mannitol-based treprostinil palmitil dry powders

| Batch# | Composition treprostinil palmitil/ DSPE-PEG2000/ Man/Leu Weight Ratio | Composition Wt % | | | |
|---|---|---|---|---|---|
| | | Treprostinil Palmitil | DSPE-PEG2000 | Mannitol | Leucine |
| SD-NNP-190 | 3/1.5/80/20 | 2.87 | 1.44 | 76.6 | 19.1 |
| SD-NNP-191 | 5/2.5/80/20 | 4.65 | 2.33 | 74.4 | 18.6 |

1.1. Effect of Leucine Content on the Spray Drying Recovery

The effect of leucine on the properties of mannitol-based treprostinil palmitil dry powder was evaluated. Four leucine loads were evaluated, 0%, 10%, 20% and 30%. An increase in the mannitol loads was applied to compensate for the decrease in the leucine content.

TABLE 8

Effect of leucine on spray drying recovery and powder density

| Batch # | Leucine content, (w/w) | Composition treprostinil palmitil/ DSPE-PEG2000/ Man/Leu Wt ratio | Spray drying recovery (%) | Bulk density, (g/mL) | Tap density, (g/mL) |
|---|---|---|---|---|---|
| SD-NNP-181 | 0 | 1/0.5/100/0 | 33.18 | N/A | N/A |
| SD-NNP-180 | 10 | 1/0.5/90/10 | 92.98 | 0.237 | 0.425 |
| SD-NNP-179 | 20 | 1/0.5/80/20 | 92.24 | 0.360 | 0.651 |
| SD-NNP-177 | 30 | 1/0.5/70/30 | 85.23 | 0.246 | 0.522 |

Spray drying recovery (0%) was low from the batch that did not contain leucine. The recovery rate increased significantly as the leucine levels were increased to 10% and 20%. The recovery rate then dropped slightly when the leucine content was increased further to 30% (FIG. 1). The batch with 200% of leucine had the highest value for powder density (Table 8).

1.2. Effect of Leucine Content (30%, 20%, 10% and 0%) on the Powder Morphology,

SEM was performed to examine the effect of leucine content on the powder surface (FIGS. 2A-2D). The change in leucine content gave rise to different weight ratios of mannitol to leucine, i.e., 70/30, 80/20, 90/10, and 100/0.

Figure 2A:
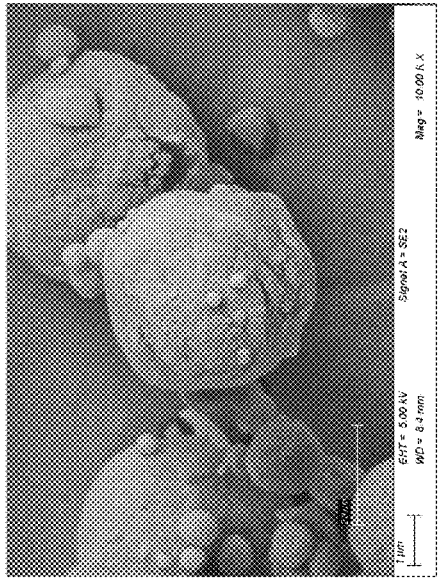
FIGS. 2A-2D are SEM images of mannitol-based C16TR (treprostinil palmitil) dry powders containing different amounts of leucine as indicated.
Figure 2B:
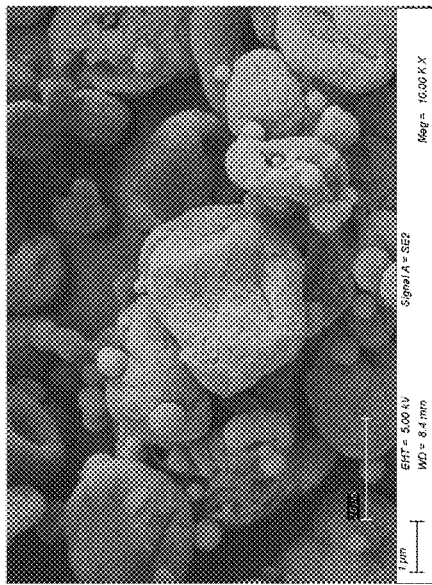
Figure 2C:
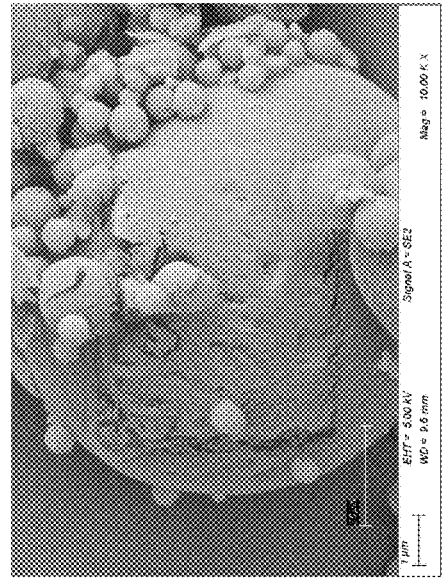
Figure 2D:
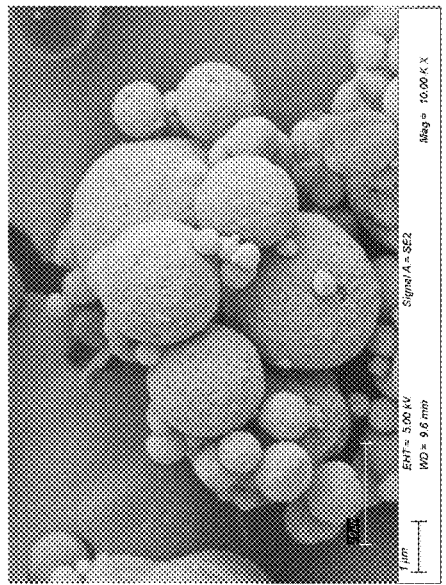

Treprostinil palmitil dry powder samples with different weight ratios of mannitol to leucine (70/30, 80/20, 90/10, and 100/0) were generated. The SEM data showed that increasing the leucine content from 20% to 30% resulted in powder with the crimped surface (FIGS. 2A and 2B). Dry powder without leucine was broken after spray drying, along with a low recovery rate (FIG. 2D). In further studies, 20% of leucine was used.

1.3. Effect of Leucine Content on the PSD (Tested by Laser Diffraction)

Three batches of mannitol-based dry powders, containing 10, 20 and 30% of leucine (w/w), were investigated by laser diffraction. The batch information was shown in Table 9.

TABLE 9

Effect of leucine on particle size distribution (laser diffraction)

| Batch# | Leucine in dry powder, (w/w) | Composition treprostinil palmitil/ DSPE-PEG2000/ Man/Leu Wt ratio | D10, μm | D50, μm | D90, μm | Span |
|---|---|---|---|---|---|---|
| SD-NNP-177 | 30 | 1/0.5/70/30 | 1.13 | 4.74 | 9.34 | 1.73 |
| SD-NNP-179 | 20 | 1/0.5/80/20 | 0.61 | 2.75 | 6.58 | 2.17 |
| SD-NNP-180 | 10 | 1/0.5/90/10 | 0.79 | 3.67 | 8.06 | 1.98 |

Figure 3:
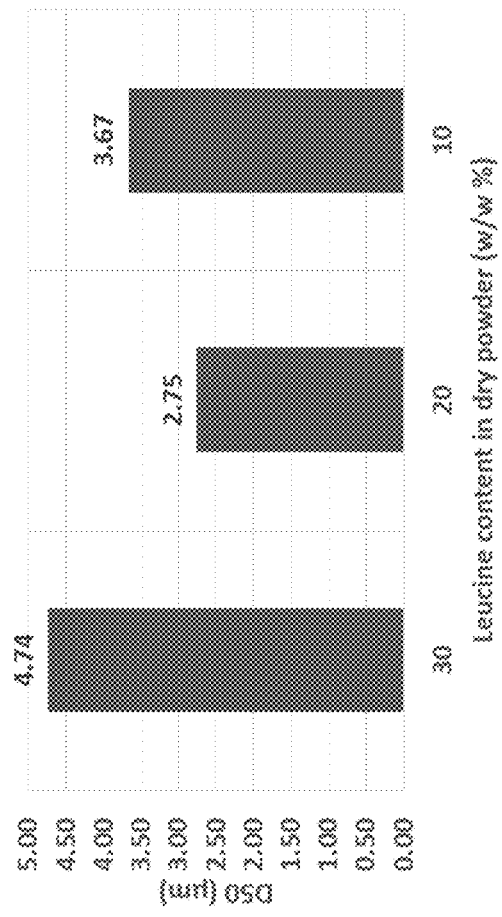
FIG. 3 is a graph showing the effect of leucine content on particle size distribution measured by laser diffraction in mannitol-based C16TR (treprostinil palmitil) dry powders.

As shown in FIG. 3, the formulation with 20% of leucine had the smallest particle size (D50). Formulations with 20% of leucine would be used in further studies in this example.

1.4. Effect of Various Amounts of Treprostinil Palmitil on MMAD

Different amounts of treprostinil palmitil were incorporated into the mannitol-based dry powder formulations, with an aim to investigate their effects on dry powder properties. As shown in Table 10, five batches of dry powders with treprostinil palmitil ranging from 1% to 5% and the weight ratio of treprostinil palmitil/DSPE-PEG2000 of 2:1 were prepared.

TABLE 10

Batches of mannitol-based treprostinil palmitil dry powders for studying the effect of treprostinil palmitil content on MMAD

| Batch# | Treprostinil Palmitil (%) | Treprostinil palmitil/ DSPE-PEG2000/Man/Leu (wt ratio) |
|---|---|---|
| SD-NNP-179 | 1 | 1/0.5/80/20 |
| SD-NNP-183 | 1.5 | 1.5/0.75/80/20 |
| SD-NNP-184 | 2 | 2/1/80/20 |
| SD-NNP-190 | 3 | 3/1.5/80/20 |
| SD-NNP-191 | 5 | 5/2.5/80/20 |

Figure 4:
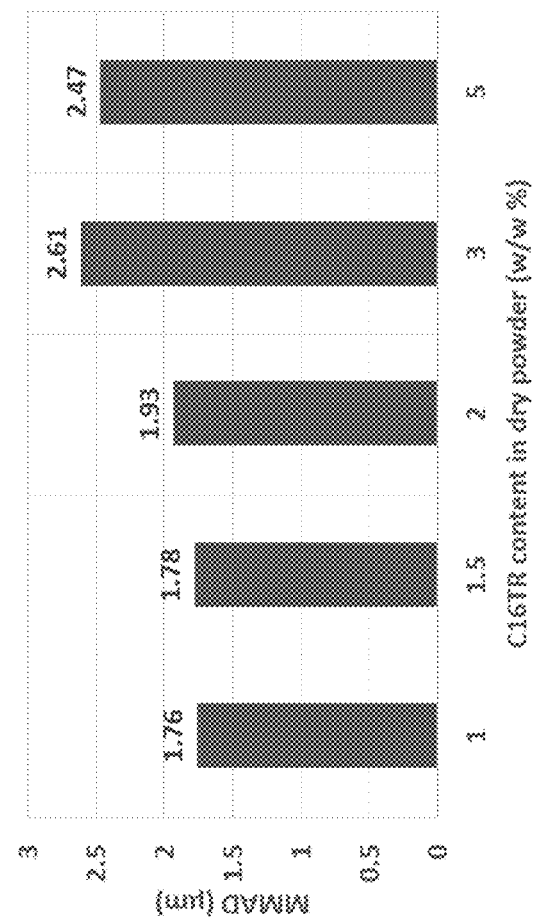
FIG. 4 is a graph showing the effect of C16TR (treprostinil palmitil) content on MMAD of mannitol-based C16TR (treprostinil palmitil) dry powders.

The value of MMAD was constant when there was 1 to 2% of treprostinil palmitil in the dry powder, and it increased significantly when treprostinil palmitil was increased to 3 to 5% (FIG. 4).

Figure 5A:
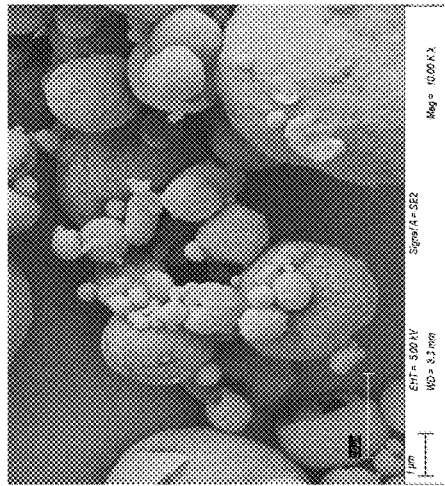
FIGS. 5A-5C are SEM images of mannitol-based C16TR (treprostinil palmitil) dry powders spray dried at different inlet temperatures. The images of the upper panel were taken at high magnification and the images of the lower panel were taken at low magnification.
Figure 5A:
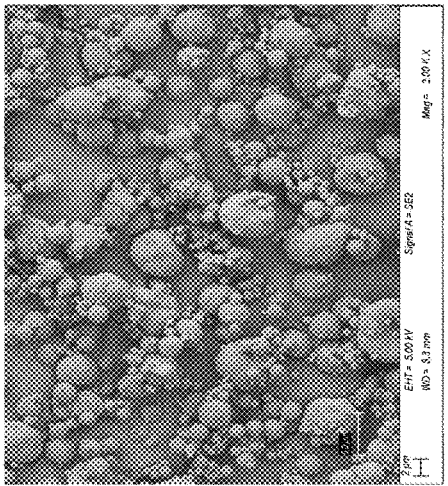
Figure 5B:
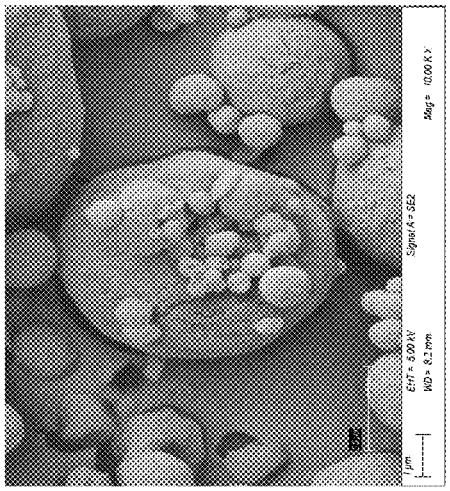
Figure 5B:
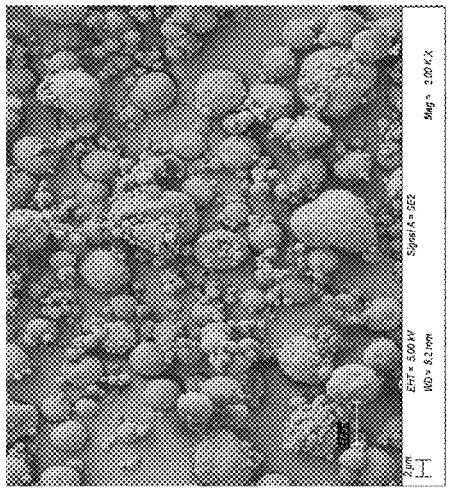
Figure 5C:
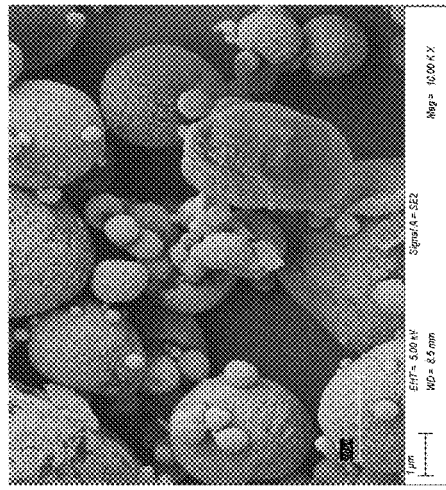
Figure 5C:
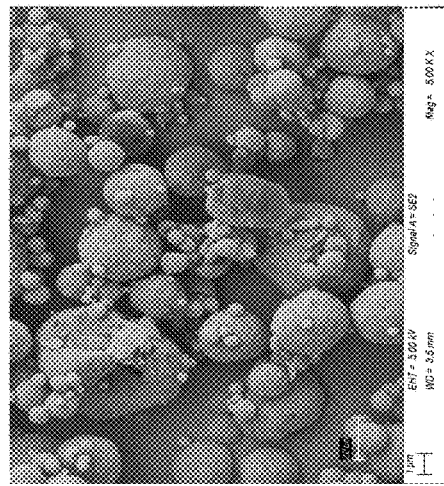

1.5. Effect of Spray Drying Inlet Temperature at 150° C., 135° C. and 120° C. on Powder Morphology Mannitol-based treprostinil palmitil dry powders with the same component ratios were generated at different inlet temperatures, i.e., 150° C., 135° C., and 120° C. (Table 11). The effect of the inlet temperature on the dry powder morphology was investigated first. SEM revealed that less surface breakage was present in the dry powder samples spray dried at lower inlet temperatures of 135° C. and 120° C. (FIGS. 5A-5C). Since no significant difference was noticed between 135° C. and 120° C. (FIGS. 5B and 5C), the inlet temperature of 135° C. was used in further investigations.

TABLE 11

Mannitol-based dry powders spray dried at different inlet temperatures

| Batch# | Composition treprostinil palmitil/DSPE-PEG2000/Man/Leu (Wt ratio) | Spray drying inlet temperature (° C.) |
|---|---|---|
| SD-NNP-167 | 1/0.5/80/20 | 150 |
| SD-NNP-170 | 1/0.5/80/20 | 135 |
| SD-NNP-171 | 1/0.5/80/20 | 120 |

Figure 6A:
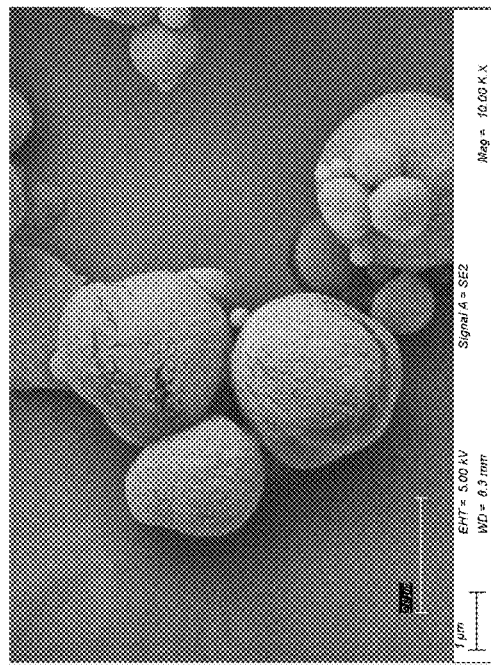
FIGS. 6A and 6B are SEM images showing the morphology of mannitol-based C16TR (treprostinil palmitil) dry powders spray dried at the inlet temperature of 135° C. with or without ammonium bicarbonate (ABC, 0.5 mg/mL). The images of the upper panel were taken at high magnification and the images of the lower panel were taken at low magnification.
Figure 6A:
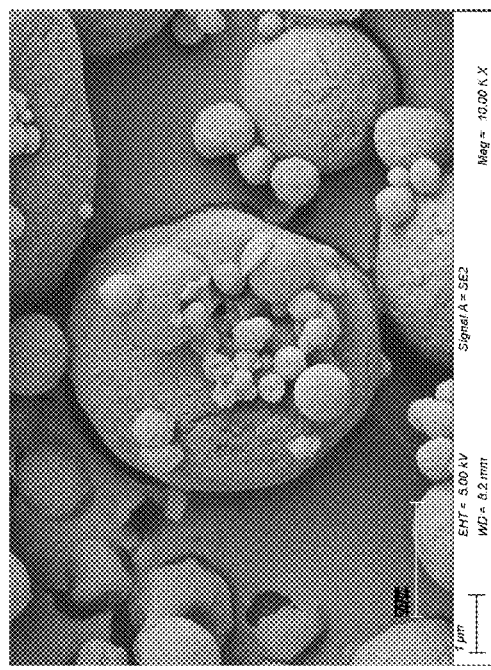
Figure 6B:
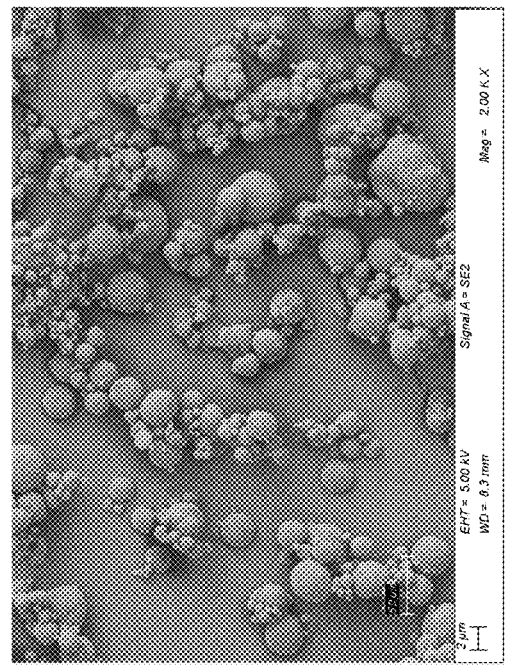
Figure 6B:
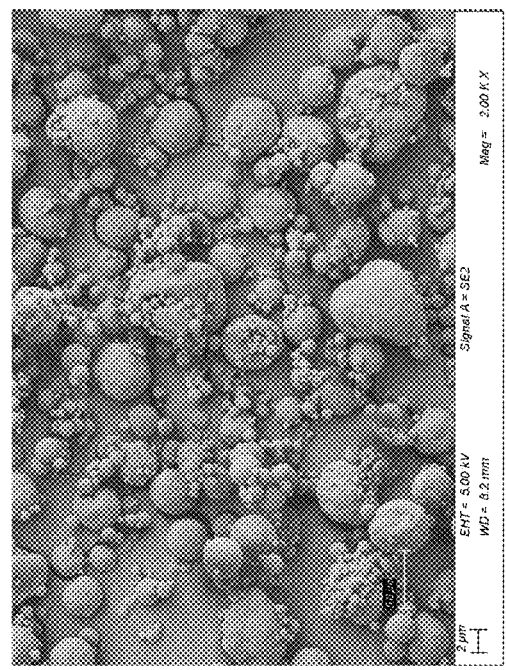

1.6. Effect of Ammonium Bicarbonate (ABC) in the Feed Stock on Mannitol-Based Treprostinil Palmitil Dry Powder Morphology The effect of ABC on the mannitol-based treprostinil palmitil dry powder morphology was examined by adding or not ABC to the feed stock when preparing the dry powder (Table 12). No powder surface change was observed by the addition of ABC (FIGS. 6A and 6B). Therefore, ABC would not be applied in mannitol-based treprostinil palmitil dry powder.

TABLE 12

Batches of mannitol-based treprostinil palmitil dry powders with or without ammonium bicarbonate (ABC)

| Batch # | Composition treprostinil palmitil/DSPE-PEG2000/Man/Leu (Wt ratio) | ABC (mg/ml) |
|---|---|---|
| SD-NNP-170 | 1/0.5/80/20 | 0 |
| SD-NNP-173 | 1/0.5/80/20 | 0.5 |

Figure 7A:
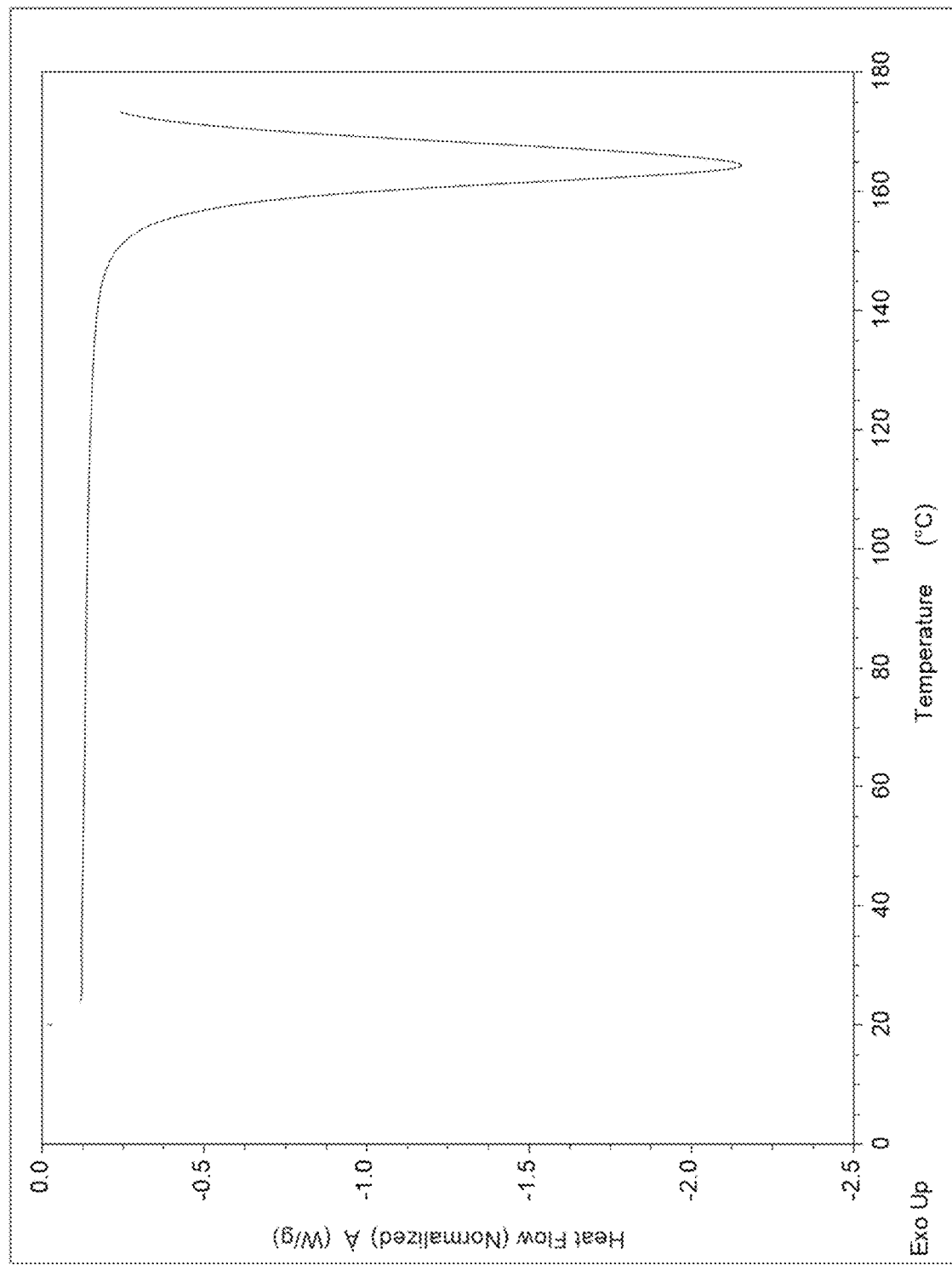
FIG. 7A is a graph showing the DSC data of the mannitol-based C16TR (treprostinil palmitil) dry powder batch SD-NNP-179.
Figure 7B:
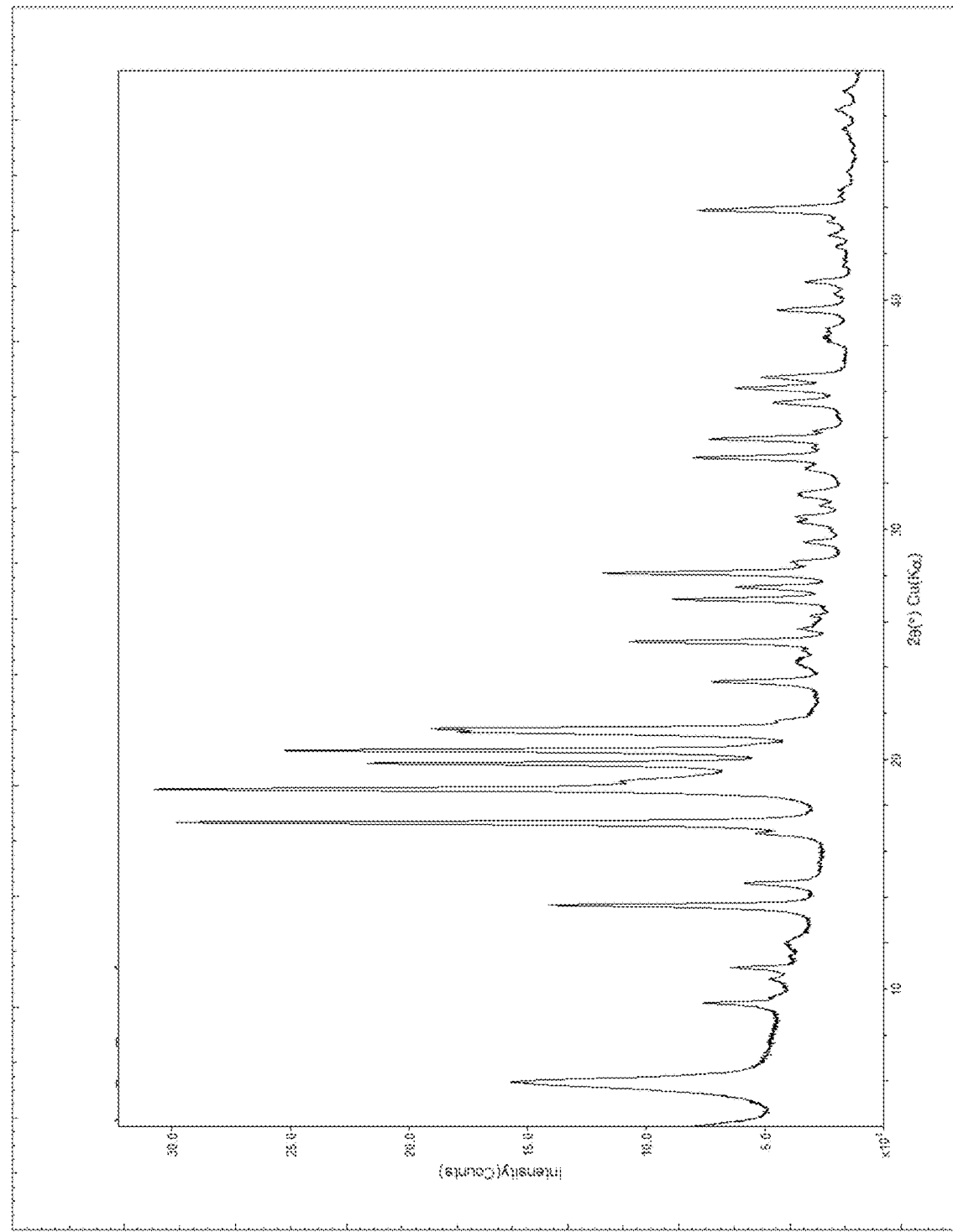
FIG. 7B is a graph showing the X-ray diffraction data of the mannitol-based C16TR (treprostinil palmitil) dry powder batch SD-NNP-179.

1.7. Physical-Chemical Properties of Mannitol-Based Treprostinil Palmitil Dry Powder The mannitol-based treprostinil palmitil dry powder was generated by spray drying a solution containing all the components. It was anticipated that the mannitol-based dry powder would show some amorphous properties, such as Tg in DSC test and broad peaks in powder X-ray diffraction test (XRD). FIGS. 7A and 7B showed the DSC and XRD data, respectively, from batch SD-NNP-179 which had 1% of treprostinil palmitil and 20% of leucine. No Tg was detected and sharp peaks in powder XRD were observed from this batch. These two characteristics were also noticed from other batches, regardless of the difference in the composition and the spray drying condition.

2. Batches of Trehalose-Based Treprostinil Palmitil Dry Powder

Different batches of trehalose-based treprostinil palmitil dry powders were made using spray drying. Table 13A shows the compositions of the batches and the inlet temperatures used for the spray drying process. For each batch, the amounts of treprostinil palmitil, DSPE-PEG2000, trehalose, and leucine are indicated by weight ratio. Table 13B shows the targeted weight percentages of treprostinil palmitil, DSPE-PEG2000, trehalose, and leucine in each batch calculated based on the weight ratio. The batches varied in the treprostinil palmitil content from 1 to 2% (weight ratio, w/w), while the ratio of treprostinil palmitil to DSPE-PEG2000 was kept the same at 2 to 1. The leucine content in the batches was 20% or 30% (w/w). During the spray drying process, the inlet temperature varied from 110° C. to 155° C.

TABLE 13A

Batches of trehalose-based treprostinil palmitil dry powders

| Batch | Excipients | Organic solvent | Composition treprostinil palmitil/DSPE-PEG2000/ Sugar/Leu Wt ratio | Inlet T (° C.) |
|---|---|---|---|---|
| SD-NNP-P144 | Treh/Leu | 1-Prop | 0/0/80/20 | 110 |
| SD-NNP-111 | Treh/Leu | 1-Prop | 0/0/80/20 | 130 |
| SD-NNP-P143 | Treh/Leu | 1-Prop | 0/0/80/20 | 150 |
| SD-NNP-169 | Treh/Leu | 1-Prop | 1/0/80/20 | 150 |
| SD-NNP-112 | DSPE-PEG2000/ Treh/Leu | 1-Prop | 0/0.5/80/20 | 130 |
| SD-NNP-162 | DSPE-PEG2000/ Treh/Leu | 1-Prop | 1/0.5/80/20 | 150 |
| SD-NNP-163 | DSPE-PEG2000/ Treh/Leu | 1-Prop | 1/0.5/70/30 | 150 |
| SD-NNP-188 | DSPE-PEG2000/ Treh/Leu | 1-Prop | 1.5/0.75/80/20 | 150 |
| SD-NNP-189 | DSPE-PEG2000/ Treh/Leu | 1-Prop | 2/1/80/20 | 150 |
| SD-NNP-P141 | Treh/Lac/Leu | EtOH | 0/0/40/40/20 | 155 |
| SD-NNP-140 | Treh/Leu | EtOH | 0/0/80/20 | 155 |

TABLE 13B

Amounts of treprostinil palmitil, DSPE-PEG2000, trehalose, and leucine expressed in weight ratios and corresponding targeted weight percentages in batches of trehalose-based treprostinil palmitil dry powders

| Batch | Excipients | Composition treprostinil palmitil/ DSPE-PEG2000/ Sugar/Leu (Wt ratio) | Composition wt % | | | |
|---|---|---|---|---|---|---|
| | | | treprostinil palmitil | DSPE-PEG2000 | Trehalose | Leucine |
| SD-NNP-P144 | Treh/Leu | 0/0/80/20 | 0 | 0 | 80 | 20 |
| SD-NNP-111 | Treh/Leu | 0/0/80/20 | 0 | 0 | 80 | 20 |
| SD-NNP-P143 | Treh/Leu | 0/0/80/20 | 0 | 0 | 80 | 20 |
| SD-NNP-169 | Treh/Leu | 1/0/80/20 | 0.99 | 0 | 79.2 | 19.8 |
| SD-NNP-112 | DSPE-PEG2000/ Treh/Leu | 0/0.5/80/20 | 0 | 0.50 | 79.6 | 19.9 |

TABLE 13B-continued

Amounts of treprostinil palmitil, DSPE-PEG2000, trehalose, and leucine expressed in weight ratios and corresponding targeted weight percentages in batches of trehalose-based treprostinil palmitil dry powders

| Batch | Excipients | Composition treprostinil palmitil/ DSPE-PEG2000/ Sugar/Leu (Wt ratio) | Composition wt % | | | |
|---|---|---|---|---|---|---|
| | | | treprostinil palmitil | DSPE-PEG2000 | Trehalose | Leucine |
| SD-NNP-162 | DSPE-PEG2000/Treh/Leu | 1/0.5/80/20 | 0.99 | 0.49 | 78.8 | 19.7 |
| SD-NNP-163 | DSPE-PEG2000/Treh/Leu | 1/0.5/70/30 | 0.99 | 0.49 | 68.9 | 29.6 |
| SD-NNP-188 | DSPE-PEG2000/Treh/Leu | 1.5/0.75/80/20 | 1.47 | 0.73 | 78.2 | 19.6 |
| SD-NNP-189 | DSPE-PEG2000/Treh/Leu | 2/1/80/20 | 1.94 | 0.97 | 77.7 | 19.4 |
| SD-NNP-P141 | Treh/lac/leu | 0/0/40/40/20 | Not Calculated | | | |
| SD-NNP-140 | Treh/leu | 0/0/80/20 | 0 | 0 | 80 | 20 |

2.1. Effect of Leucine Content on the Powder Morphology

Figure 8B:
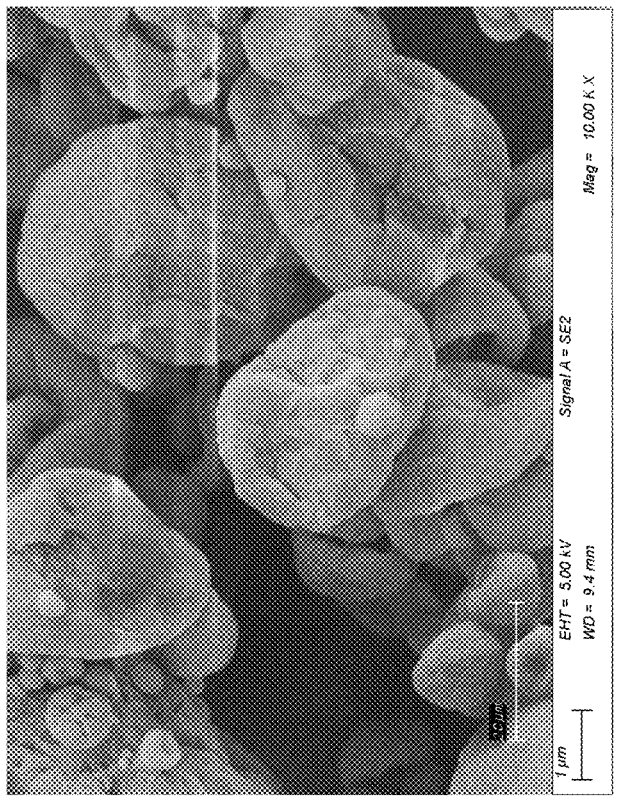
FIGS. 8A and 8B are SEM images showing the effect of leucine content on the morphology of the trehalose-based C16TR (treprostinil palmitil) dry powders.
Figure 8A:
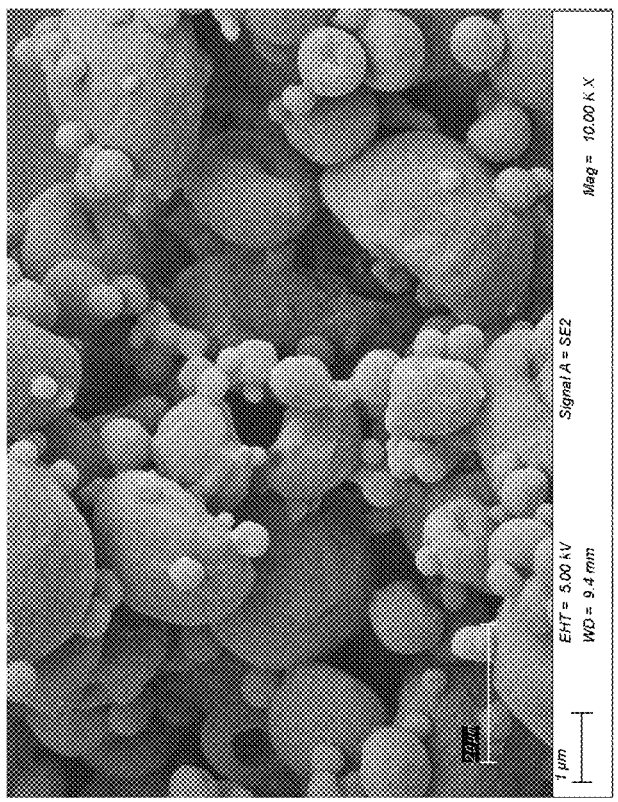

Trehalose-based treprostinil palmitil dry powders with two levels of leucine (2000 and 300%) were prepared (Table 14). The SEM data showed that increasing the leucine content from 20% to 3000 resulted in the wrinkled powder surface (FIGS. 8A and 8B).

2.2. Effect of Leucine Content on the Powder Aerosol Performance

We incorporated two levels of leucine, i.e., 20% and 30%, into the trehalose-based treprostinil palmitil dry powders, and compared their particle size (D50, laser diffraction) and MMAD (Table 14).

TABLE 14

Effect of leucine content on the aerosol performance of trehalose-based treprostinil palmitil dry powder

| Batch | Composition treprostinil palmitil/ DSPE-PEG2000/ Treh/Leu Wt ratio | D50 (μm), PSD test | MMAD (μm), NGI test | Throat + Presep (%), NGI test | Emitted dose (%), NGI test |
|---|---|---|---|---|---|
| SD-NNP-162 | 1/0.5/80/20 | 2.680 | 1.41 | 41.9 | 80.5 |
| SD-NNP-163 | 1/0.5/70/30 | 2.970 | 1.37 | 26.2 | 82.1 |

The data in Table 14 indicate that the dry powder with 30% of leucine had a larger geometric particle size (D50) and a lower deposition of powder on throat and pre-separator as compared to that with 20% of leucine. The low solubility of leucine would cause the leucine to precipitate first. The higher amount of leucine would trigger the precipitation quicker, generating larger particles. However, there was no significant difference in MMAD.

2.3. Effect of Treprostinil Palmitil Content on Dry Powder Aerosol Performance.

Different amounts of treprostinil palmitil were incorporated into the trehalose-based treprostinil palmitil dry powders, with an aim to investigate their effects on dry powder properties. As shown in Table 15, four batches of dry powders were prepared with the treprostinil palmitil content ranging from 1% to 2% and the weight ratio of treprostinil palmitil/DSPE-PEG2000 fixed at 2:1.

TABLE 15

Effect of treprostinil palmitil content on dry powder aerosol performance

| Batch | Composition treprostinil palmitil/ DSPE-PEG2000/ Treh/Leu Wt ratio | MMAD (μm), NGI test | FPF, <5.0 μm (%), NGI test | Throat + Presep (%), NGI test |
|---|---|---|---|---|
| SD-NNP-162 | 1/0.5/80/20 | 1.41 | 40.49 | 41.9 |
| SD-NNP-163 | 1/0.5/70/30 | 1.37 | 55.93 | 26.2 |
| SD-NNP-188 | 1.5/0.75/80/20 | 1.88 | 33.54 | 47.0 |
| SD-NNP-189 | 2/1/80/20 | 1.96 | 33.10 | 46.0 |

With more treprostinil palmitil in the dry powder, MMAD and deposition on throat and pre-separator increased while the fine particle fraction (FPF) decreased (Table 15).

2.4. Effect of Spray Drying Inlet Temperature on the Powder Morphology

The inlet temperature in spray drying process was expected to influence the properties of dry powder, such as moisture content, particle size and powder morphology. Two inlet temperatures of 130° C. and 150° C. were investigated with the batches of trehalose-based vehicle dry powders shown in Table 16.

TABLE 16

Batches of trehalose-based vehicle dry powders and corresponding inlet temperatures in spray drying process

| Batch | Excipients | Feed stock solvent | Composition treprostinil palmitil/ DSPE-PEG2000/ Treh/Leu Wt ratio | Inlet T (° C.) |
|---|---|---|---|---|
| SD-NNP-111 | Treh/Leu | 1-Prop 50% | 0/0/80/20 | 130 |
| SD-NNP-P143 | Treh/Leu | 1-Prop 50% | 0/0/80/20 | 150 |
| SD-NNP-112 | DSPE-PEG2000/ Treh/Leu | 1-Prop 50% | 0/0.5/80/20 | 130 |

Figure 9B:
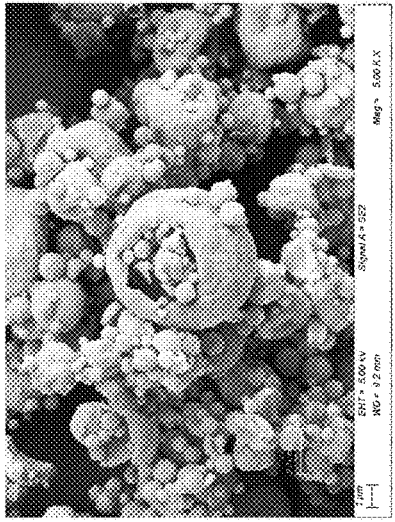
FIGS. 9A-9C are SEM images showing the effect of spray drying inlet temperature on the morphology of the trehalose-based C16TR (treprostinil palmitil) dry powders.
Figure 9A:
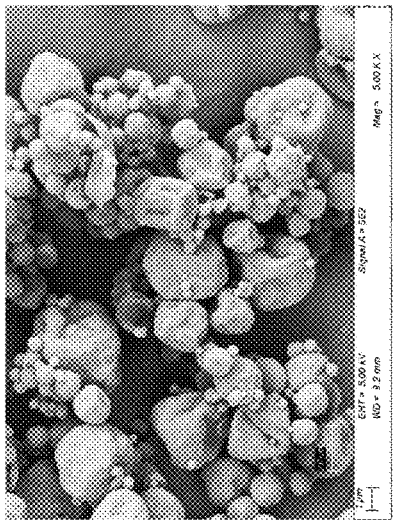
Figure 9C:
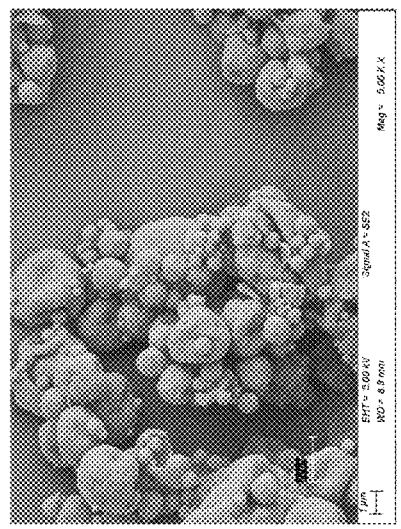

SEM revealed that a high inlet temperature of 150° C. caused the powder to break (FIGS. 9A-9C). However, to prevent high moisture in the final dry powder, 150° C. would be used for trehalose-based dry powder containing treprostinil palmitil.

2.5. Physical-Chemical Properties of Trehalose-Based Dry Powder

Similar to the mannitol-based treprostinil palmitil dry powder, the trehalose-based treprostinil palmitil dry powder was produced by spray drying a solution containing all of the components. It was anticipated that the dry powder would show some amorphous properties, such as Tg in DSC and broad peaks in powder X-ray diffraction (XRD).

Figure 10A:
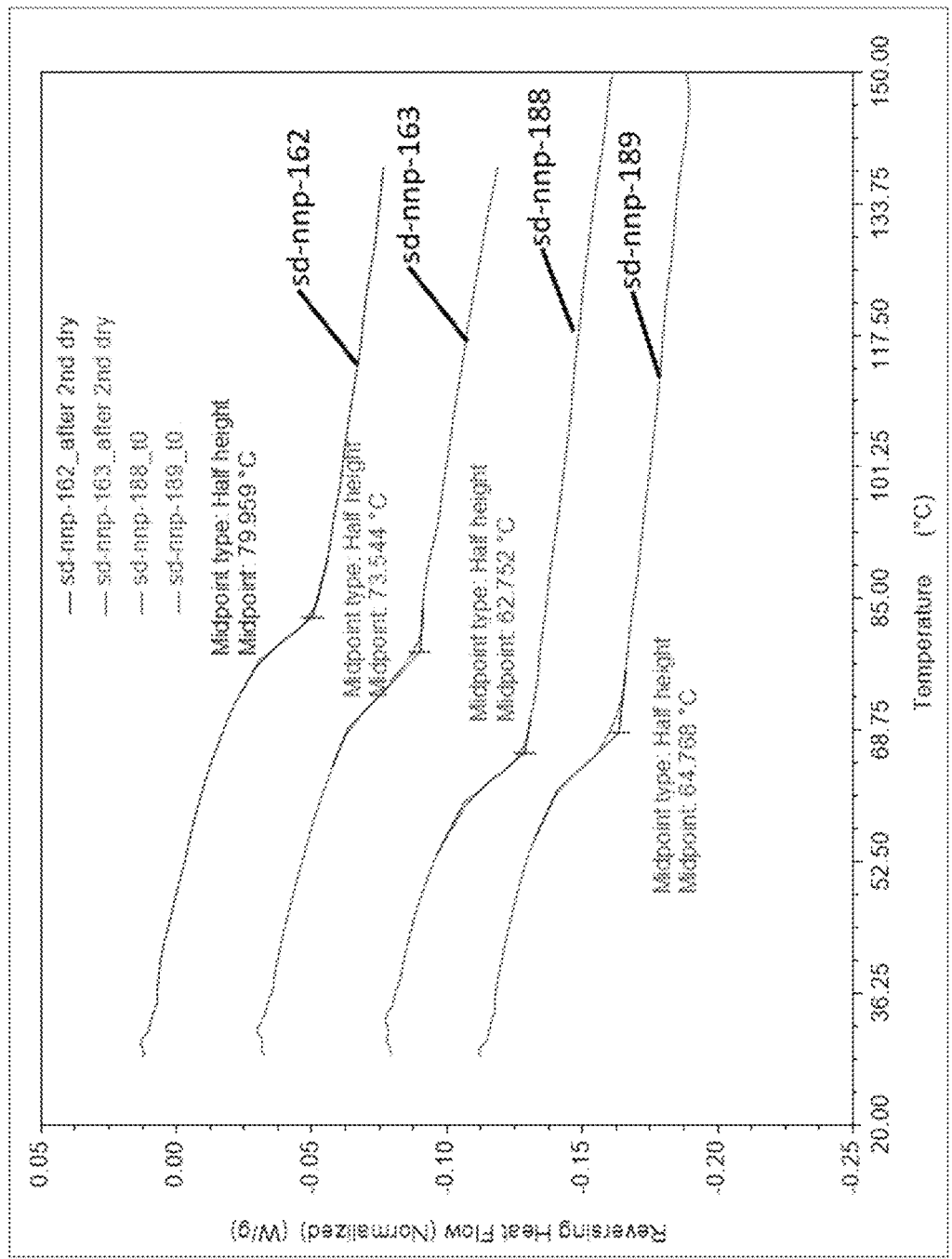
FIG. 10A is a graph showing the DSC data of the trehalose-based C16TR (treprostinil palmitil) dry powders.
Figure 10B:
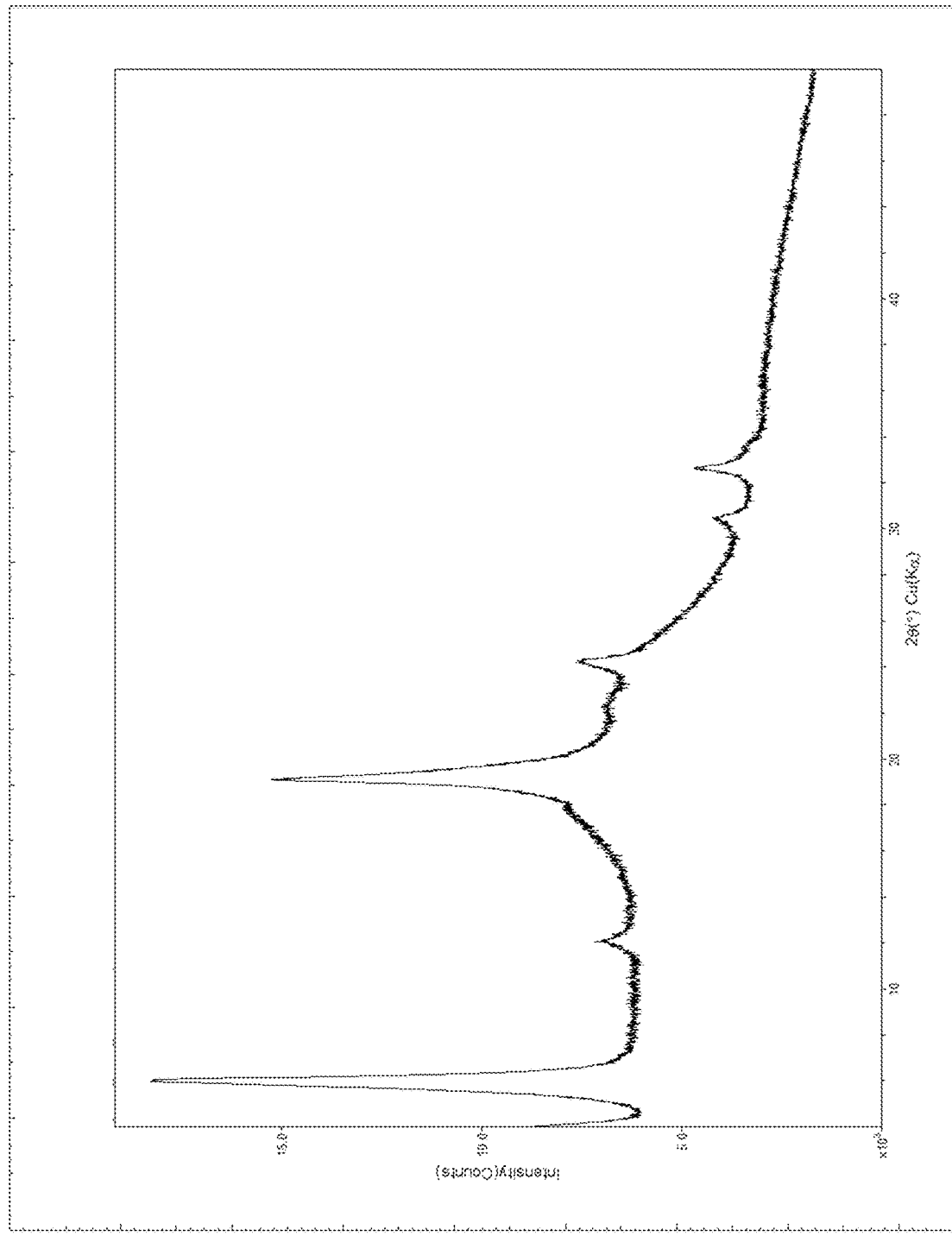
FIG. 10B is a graph showing the X-ray diffraction data of the trehalose-based C16TR (treprostinil palmitil) dry powders.

The batches of trehalose-based treprostinil palmitil dry powders shown in Table 17 were subjected to DSC and XRD. In the DSC test, a Tg was observed for all the batches, ranging from 64° C. to 80° C. The Tg could be increased if the powder experienced a $2^{nd}$ drying via overnight lyophilization, as observed in batches SD-NNP-162 and SD-NNP-163, due to a reduction of moisture in the dry powder (FIG. 10A). Compared to that from the mannitol-based dry powder, the XRD from the trehalose-based dry powder showed fewer sharp peaks (FIG. 10B), which was ascribed to the amorphous state of trehalose. All of the batches showed similar XRD data regardless of the difference in the weight ratio of the components and the spray drying condition. Table 17 shows the additional properties of the batches of the dry powder, including MMAD, FPF, and throat+pre-separator deposition.

TABLE 17

Batches of trehalose-based treprostinil palmitil dry powders for studying the physical-chemical properties

| Batch | Composition treprostinil palmitil/ DSPE-PEG2000/ Treh/Leu Wt ratio | MMAD (μm), NGI test | FPF, <5.0 μm (%), NGI test | Throat + Presep (%), NGI test |
|---|---|---|---|---|
| SD-NNP-162 | 1/0.5/80/20 | 1.41 | 40.49 | 41.9 |
| SD-NNP-163 | 1/0.5/70/30 | 1.37 | 55.93 | 26.2 |
| SD-NNP-188 | 1.5/0.75/80/20 | 1.88 | 33.54 | 47.0 |
| SD-NNP-189 | 2/1/80/20 | 1.96 | 33.10 | 46.0 |

3. Dynamic Vapor Sorption (DVS) Profile of Mannitol and Trehalose-Based Dry Powder Moisture may be introduced into a dry powder formulation during spray drying, packaging, and storage, causing product instability and package issues. Upon spray drying, moisture in dry powder may be reduced via second drying. However, during packaging, powders may absorb moisture when they are exposed to the environment, even under a humidity control condition. Moisture absorption of the mannitol and trehalose-based treprostinil palmitil dry powders was examined.

Figure 11:
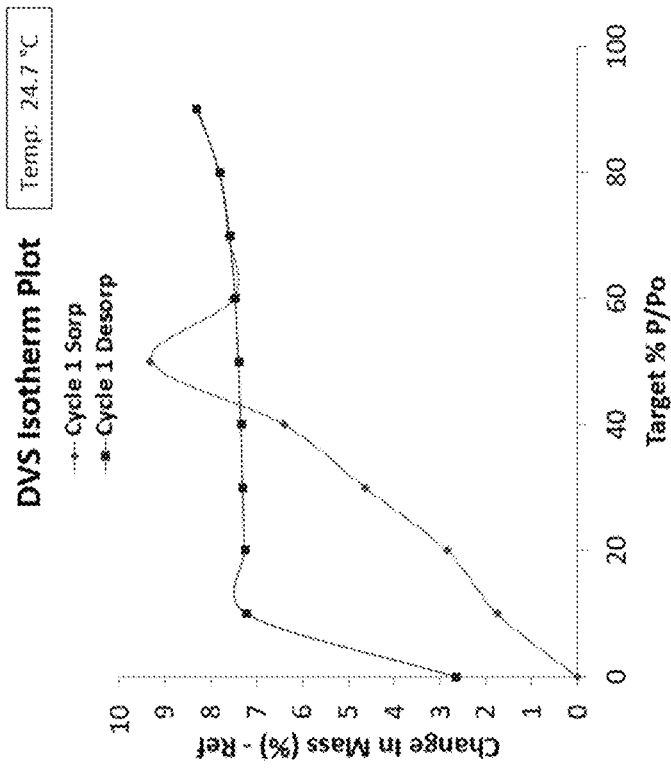
FIG. 11 is a DVS isotherm plot showing moisture absorption of the mannitol-based C16TR (treprostinil palmitil) dry powder batch SD-NNP-167 (C16TR (treprostinil palmitil)/DSPE-PEG2000/Man/Leu, 1/0.5/80/20).

As shown in FIG. 11, the mannitol-based treprostinil palmitil dry powder could absorb up to 0.3% of moisture when the RH % was increased from 0 to 40%. Compared to a lactose-based treprostinil palmitil dry powder, the mannitol-based dry powder absorbed much less moisture, probably because the mannitol-based dry powder contained crystalline mannitol and leucine and the stable form for both are un-hydrated form.

Figure 12:
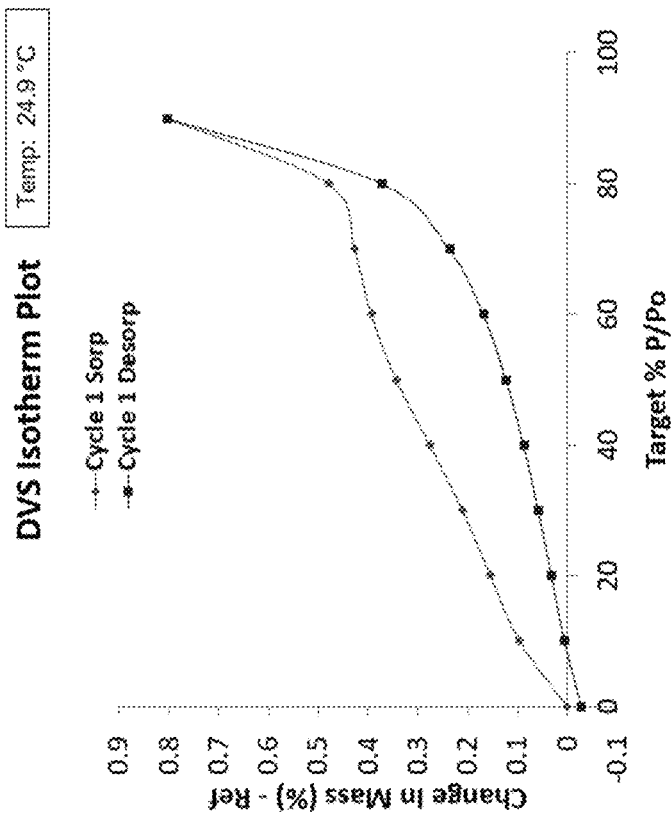
FIG. 12 is a DVS isotherm plot showing moisture absorption of the trehalose-based C16TR (treprostinil palmitil) dry powder batch SD-NNP-162 (C16TR (treprostinil palmitil)/DSPE-PEG2000/Treh/Leu, 1/0.5/80/20).
Figure 13:
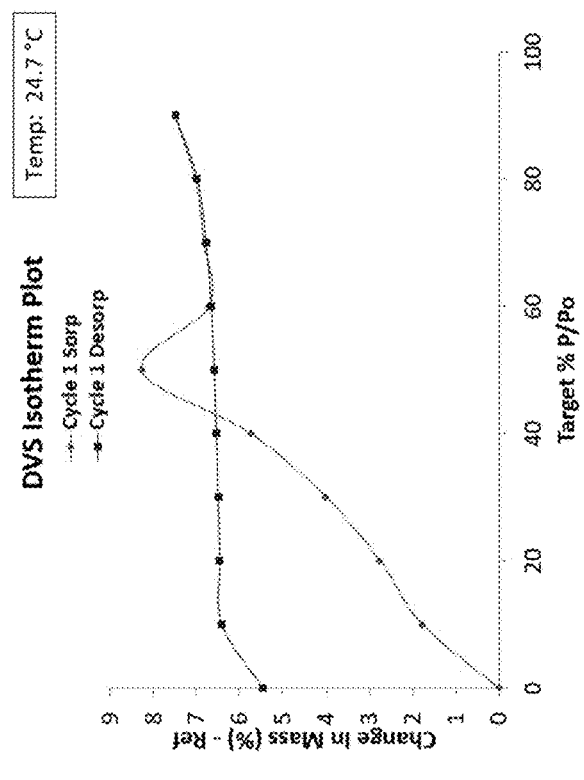
FIG. 13 is a DVS isotherm plot showing moisture absorption of the trehalose-based C16TR (treprostinil palmitil) dry powder batch SD-NNP-163 (C16TR (treprostinil palmitil)/DSPE-PEG2000/Treh/Leu, 1/0.5/70/30).

The moisture absorption profiles for the trehalose-based dry powders are shown in FIG. 12 (powder with 20% of leucine) and FIG. 13 (powder with 30% of leucine). The weight change for the trehalose based-dry powders reached the peak at 50% RH %. After that, the moisture uptake dropped due to the trehalose physical form change from amorphous to crystalline. The powder formulations with 20% and 30% of leucine had similar moisture uptake data, while the latter formulation had 1% less absorption. However, the difference was significant in the desorption process. The powder with 30% of leucine exhibited higher moisture residual at 0% RH %.

4. Stability Test for Mannitol-Based Treprostinil Palmitil Dry Powder

Figure 14:
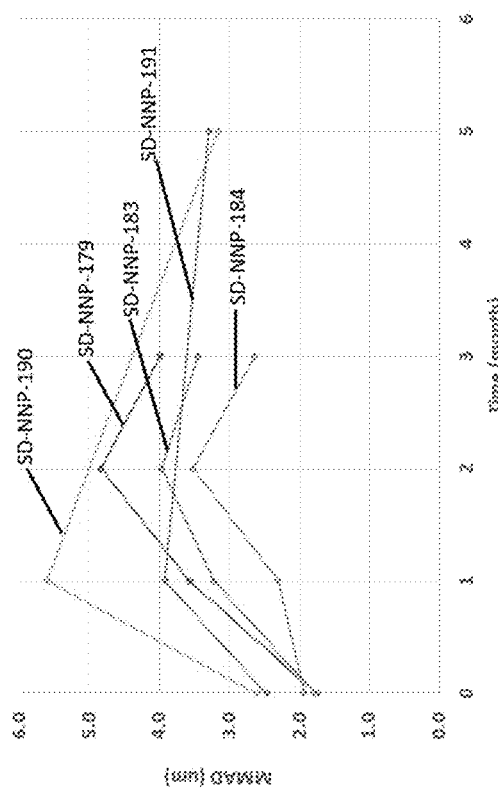
FIG. 14 is a graph showing the changes in MMAD in an accelerated stability study of the mannitol-based C16TR (treprostinil palmitil) dry powders.
Figure 15B:
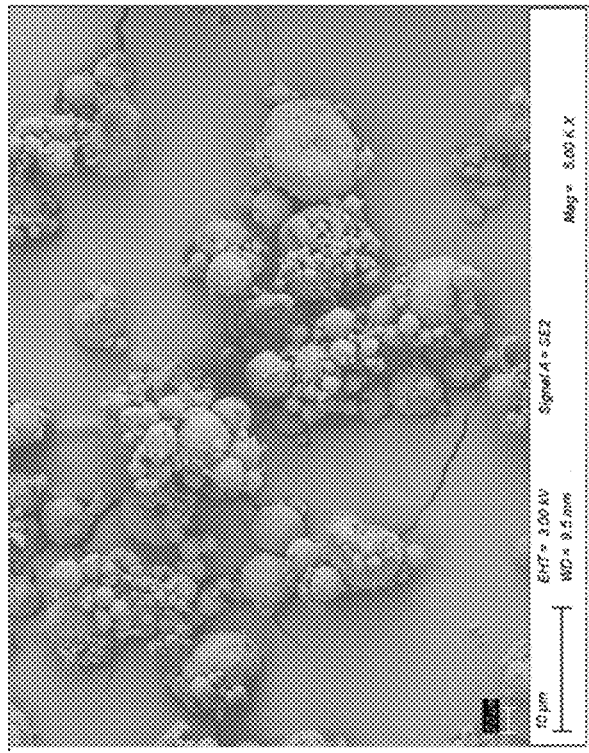
FIGS. 15A and 15B are SEM images of the mannitol-based C16TR (treprostinil palmitil) dry powder batch SD-NNP-179 with 1% of C16TR (treprostinil palmitil) at T0 and T3 (3 months), respectively.
Figure 15A:
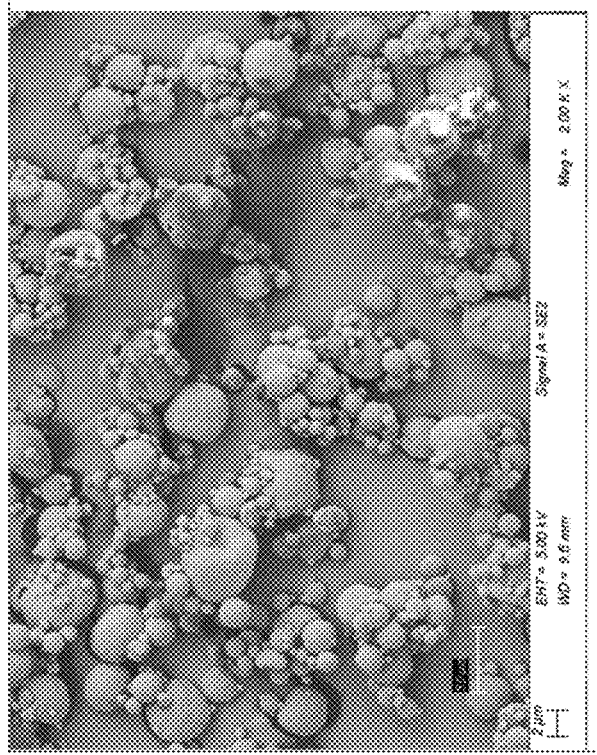
Figure 16A:
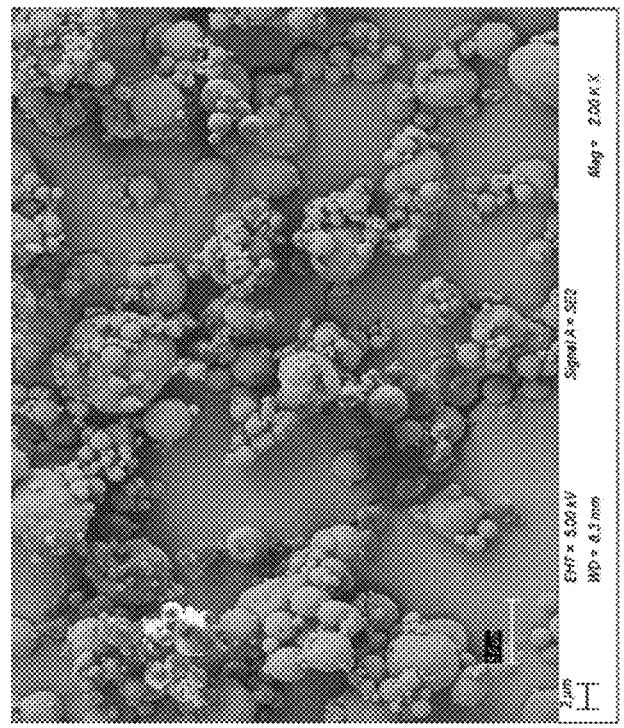
FIGS. 16A and 16B are SEM images of the mannitol-based C16TR (treprostinil palmitil) dry powder batch SD-NNP-183 with 1.5% of C16TR (treprostinil palmitil) at T0 and T3 (3 months), respectively.
Figure 16B:
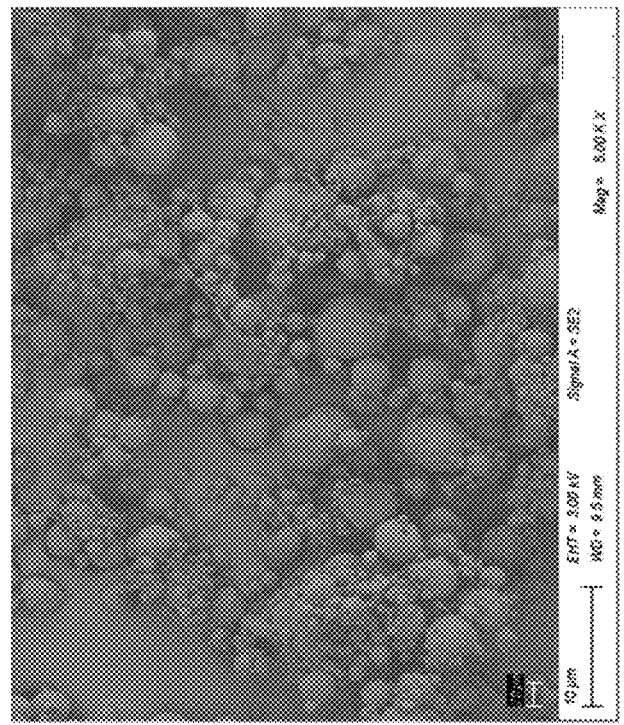
Figure 17B:
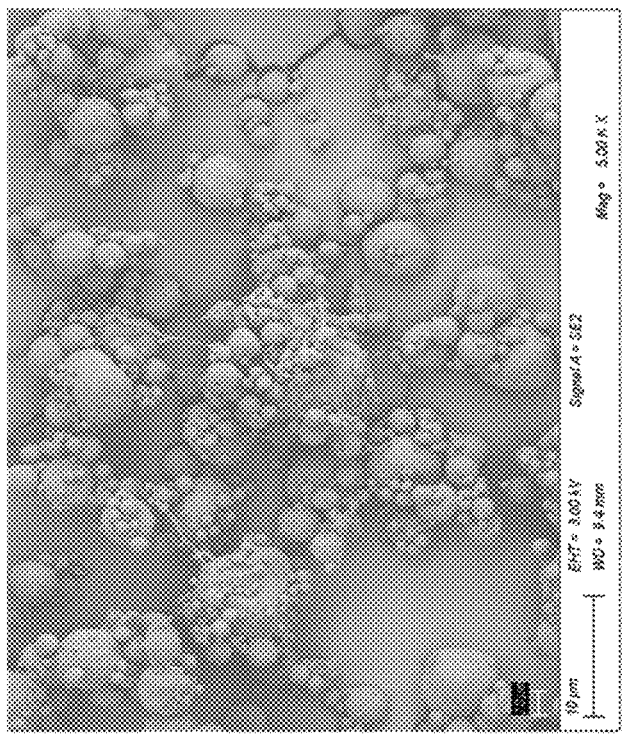
FIGS. 17A and 17B are SEM images of the mannitol-based C16TR (treprostinil palmitil) dry powder batch SD-NNP-184 with 2% of C16TR (treprostinil palmitil) at T0 and T3 (3 months), respectively.
Figure 17A:
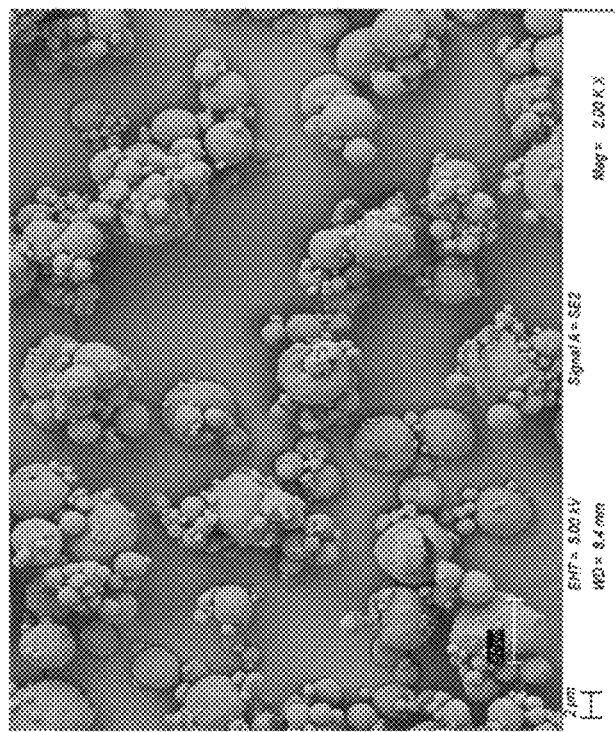
Figure 18B:
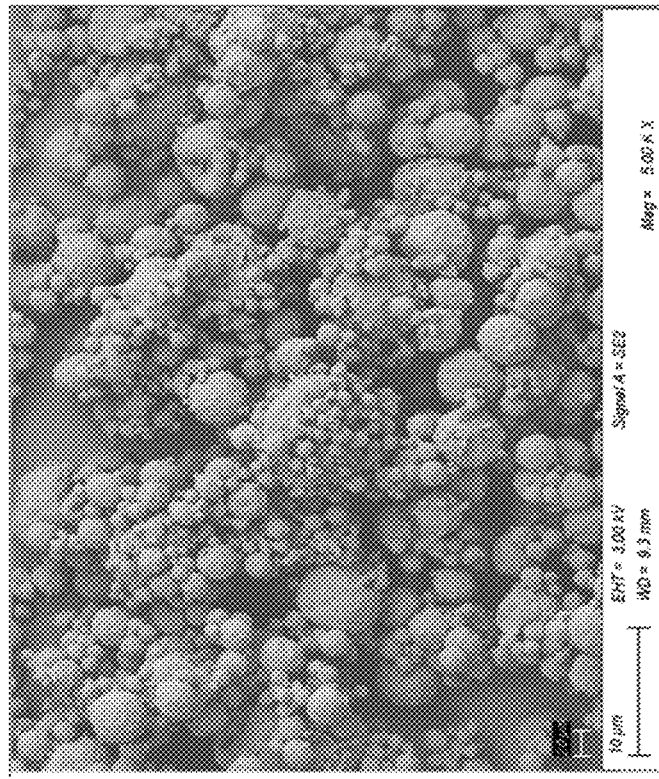
FIGS. 18A and 18B are SEM images of the mannitol-based C16TR (treprostinil palmitil) dry powder batches with 3% of C16TR (treprostinil palmitil) (SD-NNP-190) and 5% of C16TR (treprostinil palmitil) (SD-NNP-191), respectively, at T5 (5 months).
Figure 18A:
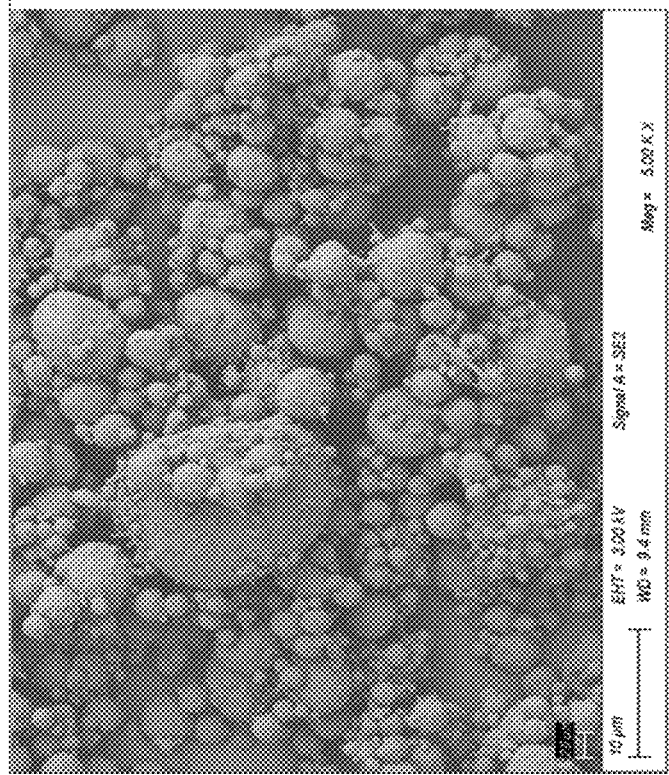

The stability test for the mannitol-based treprostinil palmitil dry powders was performed at 40° C. without humidity control, over 3 months. Five batches of mannitol-based treprostinil palmitil dry powders, containing 1, 1.5, 2, 3 and 5% of treprostinil palmitil, were investigated (Table 18). The NGI test showed that in general, the MMAD of the dry powders rose sharply at the 2-month time point and then fell back to a level similar to that at the 1-month time point (FIG. 14). The SEM data showed that dense small fibers grew on the powder surface (FIGS. 15A, 15B, 16A, 16B, 17A, 17B, 18A, and 18B).

TABLE 18

Batches of mannitol-based treprostinil palmitil dry powders for accelerated stability test

| Batch# | Treprostinil Palmitil (%) | Treprostinil palmitil/ DSPE-PEG2000/Man/Leu (wt ratio) |
|---|---|---|
| SD-NNP-179 | 1 | 1/0.5/80/20 |
| SD-NNP-183 | 1.5 | 1.5/0.75/80/20 |
| SD-NNP-184 | 2 | 2/1/80/20 |
| SD-NNP-190 | 3 | 3/1.5/80/20 |
| SD-NNP-191 | 5 | 5/2.5/80/20 |

Table 19 shows the details of the stability data of the mannitol-based treprostinil palmitil dry powder batches. In all the batches of mannitol-based dry powders containing 2000 leucine, significant changes in MMAD and FPF were observed. Additionally, initial MN/AD was lower for the dry powders with 1, 1.5, and 2% of treprostinil palmitil, as compared to that for the dry powder with 3 and 5% of treprostinil palmitil.

TABLE 19

Stability data of mannitol-based treprostinil palmitil dry powder

| Batch# | Time (months) | APSD MMAD (μm) | APSD FPF 5.0 μm (%) | PSD D50 (μm) |
|---|---|---|---|---|
| SD-NNP-179 | 0 | 1.76 | 65.8 | 2.75 |
| | 1 | 3.57 | 35.4 | 3.54 |
| | 2 | 4.83 | 30.7 | 3.70 |
| | 3 | 3.99 | 36.3 | 3.32 |
| SD-NNP-183 | 0 | 1.78 | 52.0 | 2.78 |
| | 1 | 3.22 | 46.9 | 3.32 |
| | 2 | 3.97 | 28.3 | 3.50 |
| | 3 | 3.45 | 20.7 | 3.03 |
| SD-NN-184 | 0 | 1.93 | 45.5 | 3.44 |
| | 1 | 2.31 | 45.7 | 3.35 |
| | 2 | 3.52 | 35.8 | 3.88 |
| | 3 | 2.64 | 51.4 | 3.00 |
| SD-NNP-190 | 0 | 2.61 | 56.4 | 2.82 |
| | 1 | 5.61 | 13.1 | 3.81 |
| | 5 | 3.16 | 39.6 | 3.35 |
| SD-NNP-191 | 0 | 2.47 | 56.8 | 2.78 |
| | 1 | 3.92 | 33.1 | 3.99 |
| | 5 | 3.29 | 31.7 | 4.03 |

5. Stability Test for Trehalose-Based Dry Powder

The stability study on the trehalose-based dry powder formulations, with leucine at 20% or 30% and treprostinil palmitil ranging from 1% to 2%, was also performed under the same conditions as on the mannitol-based dry powder formulations. Over the 3.5 months of the study period, no significant changes were observed (Table 20 and FIGS. 21A, 21B, 22A, 22B, 23A, 23B, 24A, and 24B).

TABLE 20

Batches of trehalose-based treprostinil palmitil dry powder for stability test

| Batch# | Treprostinil Palmitil (%) | Treprostinil palmitil/ DSPE-PEG2000/ Treh/Leu (wt ratio) | 1 month | 1.5 months | 2 months | 2.5 months | 3.5 months |
|---|---|---|---|---|---|---|---|
| SD-NNP-162 | 1 | 1/0.5/80/20 | N/A | Stable | N/A | Stable | Stable |
| SD-NNP-163 | 1 | 1/0.5/70/30 | N/A | Stable | N/A | Stable | Stable |
| SD-NNP-188 | 1.5 | 1.5/0.75/80/20 | Stable | N/A | Stable | N/A | Stable |
| SD-NNP-189 | 2 | 2/1/80/20 | Stable | N/A | Stable | N/A | Stable |

Figure 19:
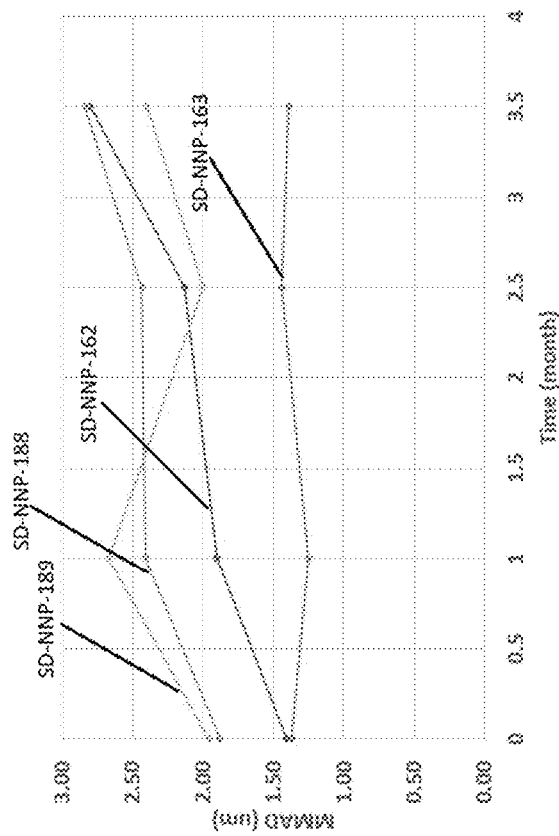
FIG. 19 is a graph showing the changes in MMAD in an accelerated stability study of the trehalose-based C16TR (treprostinil palmitil) dry powders.
Figure 20:
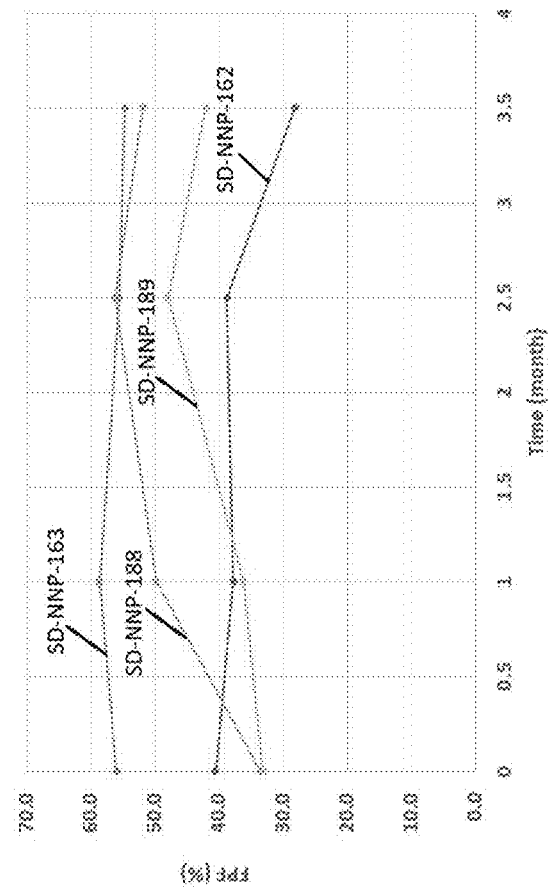
FIG. 20 is a graph showing the changes in FPF in an accelerated stability study of the trehalose-based C16TR (treprostinil palmitil) dry powders.
Figure 21B:
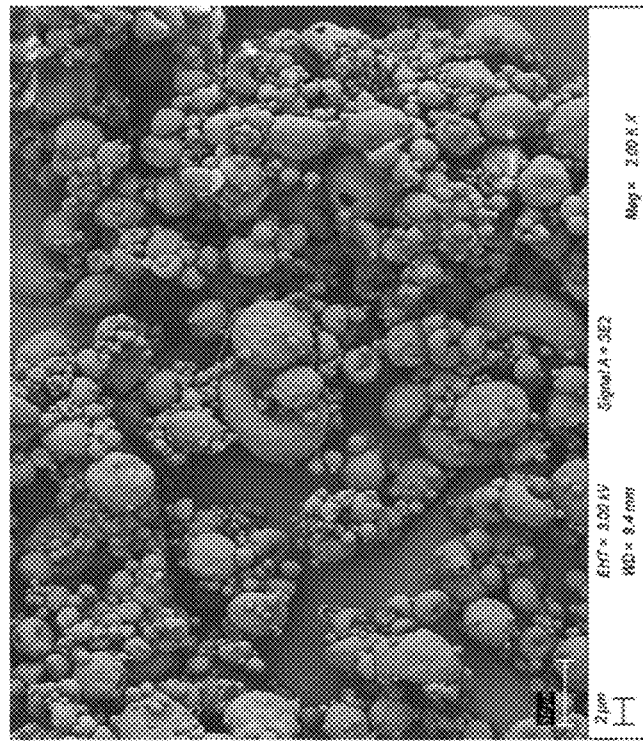
FIGS. 21A and 21B are SEM images of the trehalose-based C16TR (treprostinil palmitil) dry powder batch SD-NNP-162 with 1% of C16TR (treprostinil palmitil) at T0 and T3.5 (3.5 months), respectively.
Figure 21A:
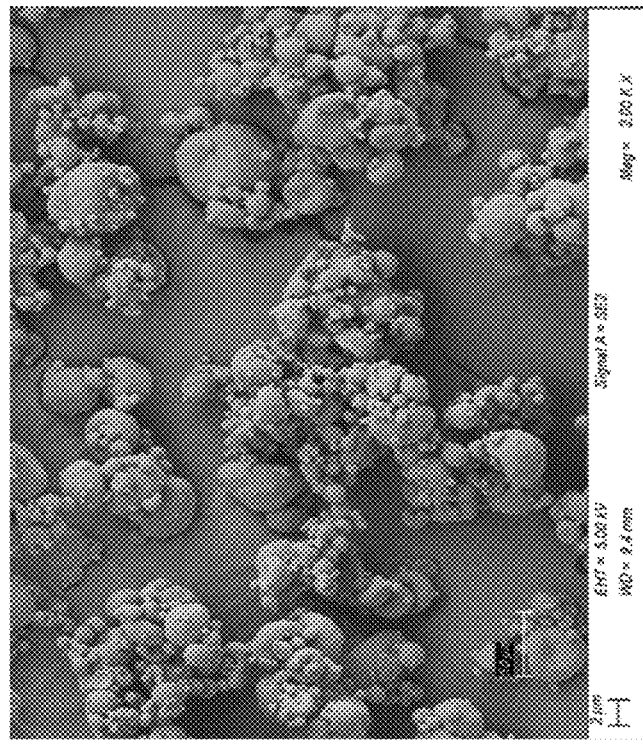
Figure 22B:
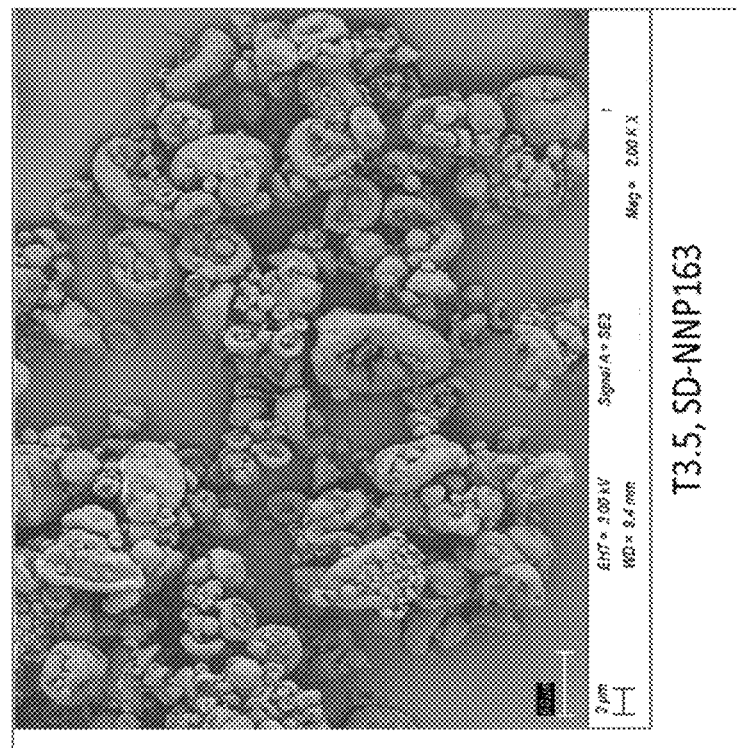
FIGS. 22A and 22B are SEM images of the trehalose-based C16TR (treprostinil palmitil) dry powder batch SD-NNP-163 with 1% of C16TR (treprostinil palmitil) at T0 and T3.5 (3.5 months), respectively.
Figure 22A:
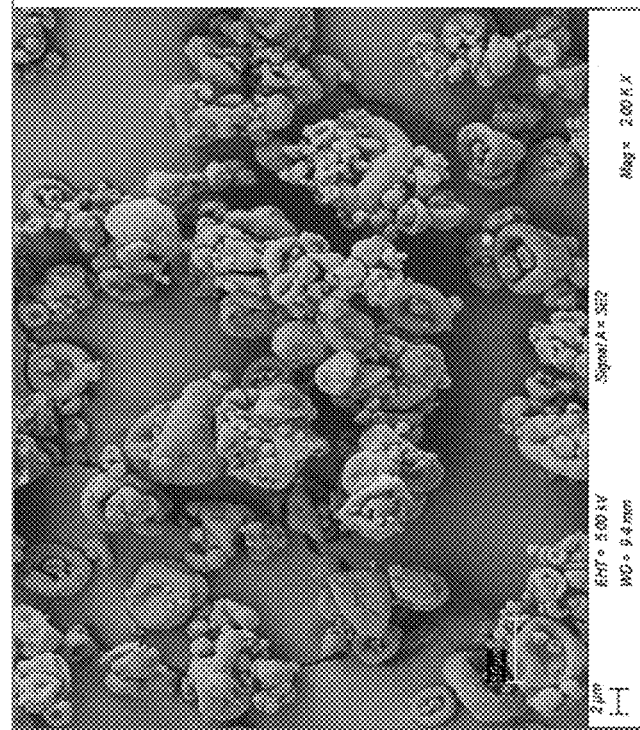
Figure 23B:
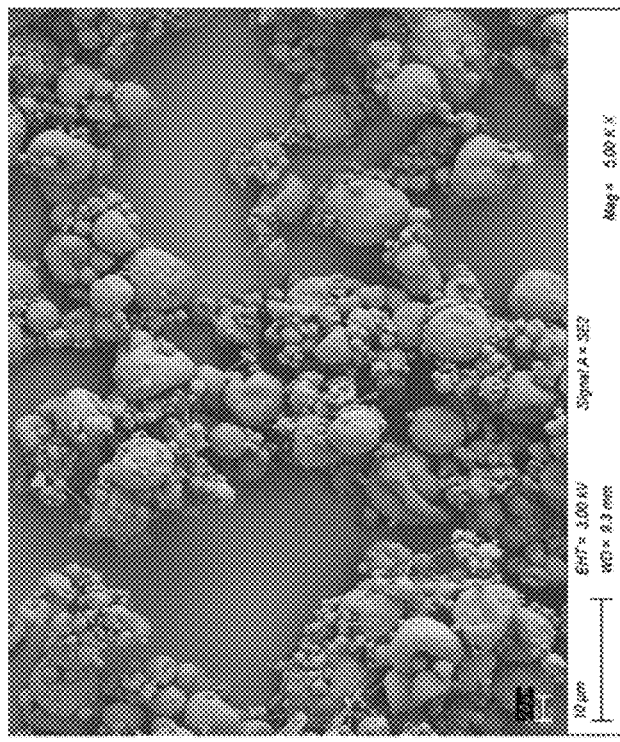
FIGS. 23A and 23B are SEM images of the trehalose-based C16TR (treprostinil palmitil) dry powder batch SD-NNP-188 with 1.5% of C16TR (treprostinil palmitil) at T0 and T3.5 (3.5 months), respectively.
Figure 23A:
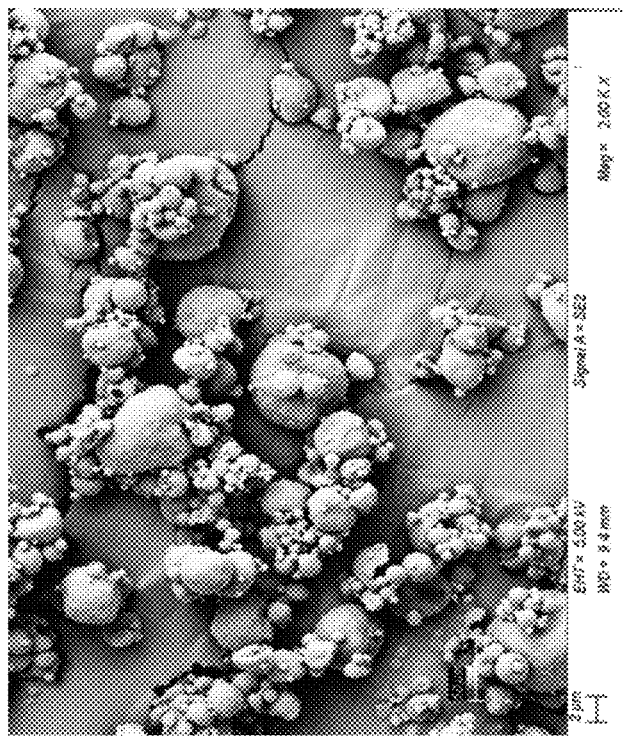
Figure 24B:
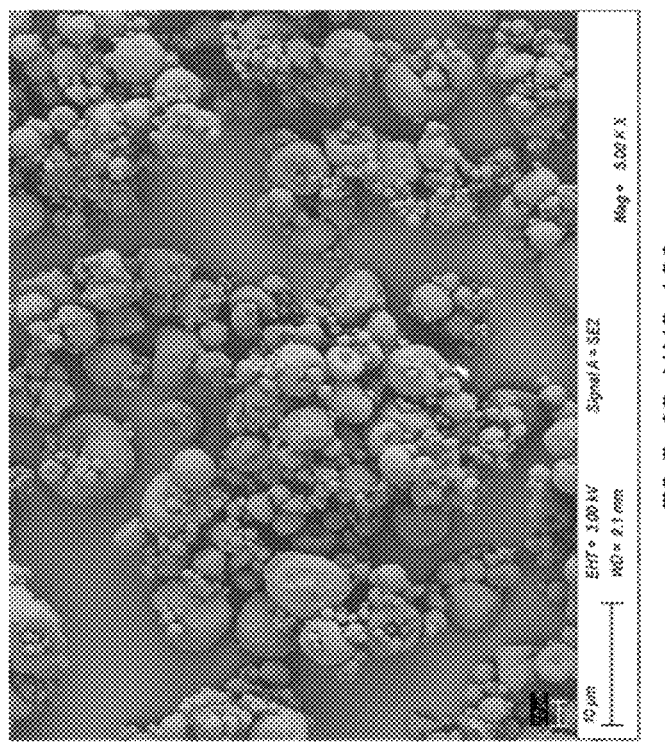
FIGS. 24A and 24B are SEM images of the trehalose-based C16TR (treprostinil palmitil) dry powder batch SD-NNP-189 with 2% of C16TR (treprostinil palmitil) at T0 and T3.5 (3.5 months), respectively.
Figure 24A:
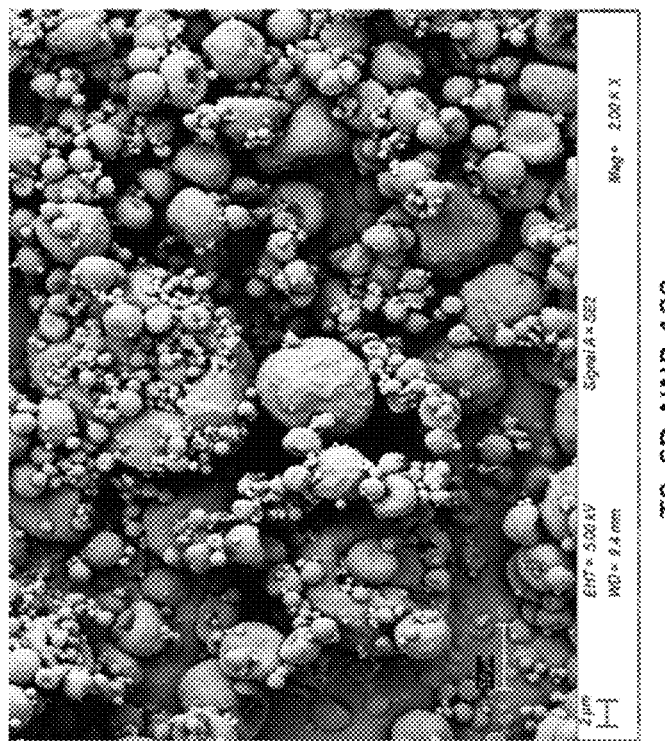

Table 21 shows the details of the stability data of the trahalose-based treprostinil palmitil dry powder batches. The MMAD increased significantly for batches SD-NNP-162 and SD-NNP-188 (Table 21 and FIG. 19). The FPF value decreased most notably for batch SD-NNP-162 (FIG. 20). Batch SD-NNP-163 (treprostinil palmitil 1%, leucine 30%) showed the lowest and stable MMAD and the highest stable FPF.

TABLE 21

Stability data of trehalose-based treprostinil palmitil dry powders

| Batch # | Time (months) | APSD MMAD (μm) | APSD FPF 5.0 μm (%) | PSD D50 (μm) |
|---|---|---|---|---|
| SD-NNP-162 | 0 | 1.41 | 40.5 | 2.68 |
| | 1 | 1.90 | 37.7 | 2.84 |
| | 2.5 | 2.13 | 38.7 | 2.74 |
| | 3.5 | 2.80 | 28.1 | 4.56 |

TABLE 21-continued

Stability data of trehalose-based treprostinil palmitil dry powders

| Batch # | Time (months) | APSD MMAD (μm) | APSD FPF 5.0 μm (%) | PSD D50 (μm) |
|---|---|---|---|---|
| SD-NNP-163 | 0 | 1.37 | 55.9 | 2.97 |
| | 1 | 1.25 | 58.7 | 3.01 |
| | 2.5 | 1.44 | 55.5 | 2.90 |
| | 3.5 | 1.39 | 54.6 | 4.62 |
| SD-NN-188 | 0 | 1.88 | 33.5 | 2.76 |
| | 1 | 2.41 | 49.7 | 3.00 |
| | 2.5 | 2.44 | 56.2 | 4.53 |
| | 3.5 | 2.84 | 51.8 | 2.98 |
| SD-NNP-189 | 0 | 1.96 | 33.1 | 2.84 |
| | 1 | 2.67 | 36.2 | 3.30 |
| | 2.5 | 2.00 | 47.9 | 4.92 |
| | 3.5 | 2.40 | 42.0 | 3.25 |

Summary of Findings for Mannitol-Based Treprostinil Palmitil Dry Powder Formulations In the mannitol-based treprostinil palmitil dry powder, addition of leucine led to a high spray drying recovery rate. The mannitol-based dry power with 20% of leucine displayed spherical particle shape and a low geometric diameter (D50=2.75 μm).

In the spray drying process, the inlet temperature varied from 120° C. to 150° C. did not impact the morphology of the mannitol-based treprostinil palmitil dry powder. Since the moisture content was around 1% from the dry powder produced under 135° C., the inlet temperature was set at 135° C.

No glass transitions were detected from the mannitol-based treprostinil palmitil dry powder in the DSC test, supporting the X-ray diffraction test (XRD) result indicating crystalline materials. In addition, the spray dried mannitol-based treprostinil palmitil dry powder was less hydroscopic, absorbing moisture less than 1% at 90% RH %.

In the stability test of the mannitol-based treprostinil palmitil dry powders, the MMAD rose sharply at 2-month time point for formulations with 1 to 2% of treprostinil palmitil, and at 1-month time point for formulations with higher treprostinil palmitil contents. The MMAD dropped at later time points. All formulations showed fibers on the powder surface after storage.

Summary of Findings for Trehalose-Based Treprostinil Palmitil Dry Powder Formulations The trehalose-based treprostinil palmitil dry powder containing 30% leucine had wrinkled surface and less powder deposited in the throat and pre-separator as compared to that containing 20% leucine. However, there was no significant difference in MMAD between the two.

The inlet temperature in the spray drying process was selected at 150° C. for achieving a lower moisture content in final dry powder.

Glass transition temperature (Tg) in the range of 64 to 80° C. was observed, indicating an amorphous state of trehalose in the dry powder. The trehalose-based treprostinil palmitil dry powder showed higher absorption of moisture compared to the mannitol-based treprostinil palmitil dry powder.

In the stability test, most of the trehalose-based treprostinil palmitil dry powder formulations tested exhibited no significant change in FPF. All formulations showed hair-like crystals on the powder surface after storage.

Taken together, the data of this example indicate that the content of treprostinil palmitil in the range up to 2 wt % did not affect the physical properties of the treprostinil palmitil dry powder. At 3 and 5 wt % treprostinil palmitil, an increase in initial MMAD of the mannitol-based powder was noted. Leucine content was found to be important for dry powder aerosol properties.

Example 2—Manufacture, Encapsulation, and Characterization of Inhalable Mannitol and Trehalose-Based Treprostinil Palmitil Dry Powder Formulations This example describes the manufacture by spray drying and encapsulation of four treprostinil palmitil dry powder formulations, i.e., formulations A, B, C, and D. Formulations A and D were mannitol-based and their compositions in both weight ratios and targeted weight percentages calculated based on the weight ratios are shown in Table 22. Formulations B and C are trehalose-based and their compositions in both weight ratios and targeted weight percentages calculated based on the weight ratios are shown in Table 23. This example also describes the characterization of formulations A-D for particle size, morphology, water content, solvent content, physical state, vapor sorption profile, thermal properties, and weight loss as a function of temperature.

TABLE 22

Compositions of formulations A and D in weight ratios and targeted weight percentages

| Formulation | Composition treprostinil palmitil/DSPE-PEG2000/Man/Leu Wt ratio | Composition Wt % | | | |
| --- | --- | --- | --- | --- | --- |
| | | Treprostinil Palmitil | DSPE-PEG2000 | Mannitol | Leucine |
| A | 1.5/0.75/80/20 | 1.47 | 0.73 | 78.24 | 19.56 |
| D | 1.5/0.75/70/30 | 1.47 | 0.73 | 68.46 | 29.34 |

TABLE 23

Compositions of formulations B and C in weight ratios and targeted weight percentages

| Formulation | Composition treprostinil palmitil/DSPE-PEG2000/Treh/Leu Wt ratio | Composition Wt % | | | |
| --- | --- | --- | --- | --- | --- |
| | | Treprostinil Palmitil | DSPE-PEG2000 | Trehalose | Leucine |
| B | 1.5/0.5/80/20 | 0.99 | 0.49 | 78.82 | 19.70 |
| C | 1.5/0.75/70/30 | 1.47 | 0.73 | 68.46 | 29.34 |

1. Spray Drying Manufacture of Formulations A, B, C, and D

Treprostinil palmitil dry powder formulations A, B, C, and D were manufactured using a BLD-200 spray dryer with in-going solids of approximately 55 grams each. Between each condition, a blank solvent solution was sprayed to ensure the previous formulation was cleared from the solution line. No additional cleaning of the spray dryer was conducted between conditions.

Each of the four formulations was prepared as an independent solution. Solutions were prepared at room temperature without light protection. For each solution preparation, the following steps were performed:

1. Leucine was dissolved in deionized water.
2. Sugar (mannitol or trehalose) was dissolved in deionized water.
3. The aqueous solution was filtered through a 0.2 μm PVDF membrane.
4. DSPE-PEG2000 was dissolved into 1-propanol.
5. Treprostinil palmitil was dissolved into 1-propanol.
6. Organic solution was added to the stirring aqueous solution.

The spray drying formulations and process conditions are listed in Table 24. Manufacturing yields ranged from 54 to 80% by mass. Packaging of bulk dry powder of each formulation was conducted in a dry glove box.

TABLE 24

Formulations and Spray Drying Conditions

| | A | B | C | D |
|---|---|---|---|---|
| | \multicolumn{4}{c}{Formulation} | | | |
| | \multicolumn{4}{c}{Composition (wt ratio)} | | | |
| | 1.5/0.75/80/20 treprostinil palmitil/DSPE-PEG2000/Man./Leu. | 1/0.5/80/20 treprostinil palmitil/DSPE-PEG2000/Treh./Leu. | 1.5/0.75/70/30 treprostinil palmitil/DSPE-PEG2000/Treh./Leu. | 1.5/0.75/70/30 treprostinil palmitil/DSPE-PEG2000/Man./Leu. |
| Solvent Blend (wt %) | \multicolumn{4}{c}{50/50 1-propanol/$H_2O$} | | | |
| Solids Loading (wt %) | \multicolumn{4}{c}{2} | | | |
| Dryer Scale | \multicolumn{4}{c}{BLD-200} | | | |
| Chamber Pressure | \multicolumn{4}{c}{Negative} | | | |
| Cyclone | \multicolumn{4}{c}{3-Inch} | | | |
| Atomizer | \multicolumn{4}{c}{Two-Fluid (1650/120)} | | | |
| Atomization Pressure | \multicolumn{4}{c}{45 PSIG (217 g/min, 13 kg/hr)} | | | |
| Drying Gas (g/min) | \multicolumn{4}{c}{1300 (78 kg/hr)} | | | |
| Feed rate (g/min) | \multicolumn{4}{c}{30} | | | |
| Inlet Temp (° C.) | \multicolumn{4}{c}{145} | | | |
| Outlet Temp (° C.) | \multicolumn{4}{c}{60} | | | |
| Outlet % RH (Calc.) | \multicolumn{4}{c}{8} | | | |
| Outlet % RS (Est.) | \multicolumn{4}{c}{1.3} | | | |
| In-going Solids (g) | \multicolumn{4}{c}{~55} | | | |
| Solids Yield (g) | 29.8 | 42.5 | 32.4 | 43.8 |
| % Yield | 54 | 77 | 59 | 80 |

2. Powder Encapsulation

Dry power formulations were encapsulated by using an Xcelodose 600S to fill 50-51 capsules per formulation. Relative humidity of suite was less than 30%. A summary of the encapsulation is shown in Table 25. For example, capsules were made from a typical batch of formulation D (containing 1.50 wt treprostinil palmitil, 0.75 wt % DSPE-PEG2000, 68.45 wt % mannitol, and 29.30 wt % leucine) by filling in each capsule 112.5 μg of treprostinil palmitil, 56.2 μg of DSPE-PEG2000, 5133.8 g of mannitol, and 2197.5 g of leucine. Other batches of formulation D with wt % for each component independently varying at or within ±50% of the typical wt % value as indicated above were observed to have equivalent properties and performance. Capsules were collected in glass jars and heat sealed in a foil bags with 0.5 g molecular sieve desiccant.

TABLE 25

Xcelodose Performance Summary

| Formulation | Composition (weight ratio) | Target Range (mg) | Machine Yield | Mean Fill (mg) | % RSD | Powder Used (mg) |
|---|---|---|---|---|---|---|
| A | 1.5/0.75/80/20 treprostinil palmitil/ DSPE-PEG2000/ Man./Leu. | 6.7 ± 0.7 | 92.4% | 6.6 ± 0.2 | 3.3 | ~370 |
| B | 1/0.5/80/20 treprostinil palmitil/ DSPE-PEG2000/ Treh./Leu. | 10.0 ± 1.0 | 96.1% | 10.2 ± 0.3 | 2.5 | ~530 |
| C | 1.5/0.75/70/30 treprostinil palmitil/ DSPE-PEG2000/ Treh./Leu. | 6.7 ± 0.7 | 96.3% | 6.6 ± 0.1 | 1.9 | ~350 |
| D | 1.5/0.75/70/30 treprostinil palmitil/ DSPE-PEG2000/ Man./Leu. | 6.7 ± 0.7 | 91.6% | 6.6 ± 0.2 | 2.6 | ~370 |

3. Analytical Characterization

Each of the four formulations was evaluated for the particle size distribution, particle morphology, water content, residual solvent, physical state, moisture sorption and thermal properties. A summary of the results is shown in Table 26.

Figure 30:
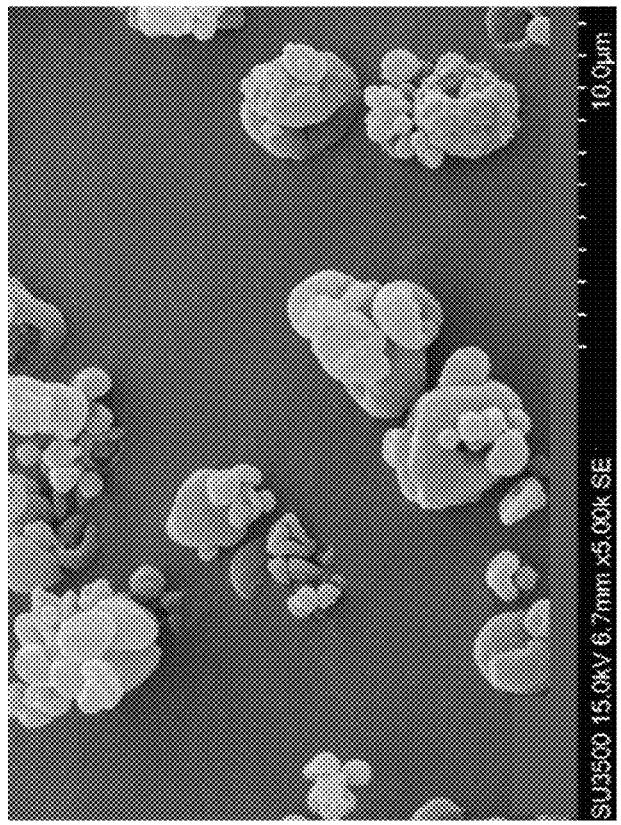
FIG. 30 is an SEM image of treprostinil palmitil dry powder formulation D.
Figure 29:
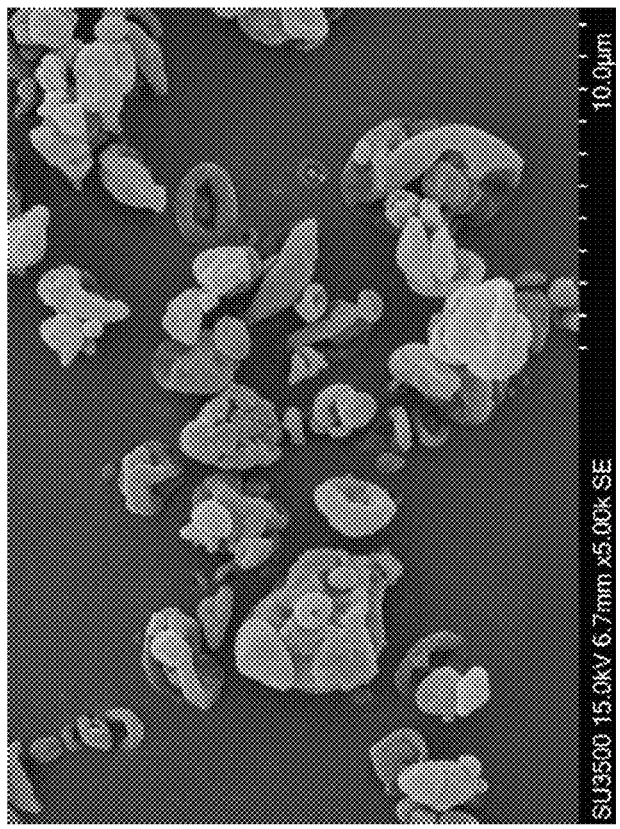
FIG. 29 is an SEM image of treprostinil palmitil dry powder formulation C.

FIG. 29 (formulation C) and FIG. 30 (formulation D). All the formulations contained full and collapsed spherical particles approximately 3 µm or less in diameter, consistent with the laser diffraction results. Formulation C appeared to be the most corrugated while formulation A appeared to be the most "smooth". The surface roughness may improve

TABLE 26

Analytical Characterization Summary

| | Formulation A | Formulation B | Formulation C | Formulation D |
|---|---|---|---|---|
| Particle Size Distribution | | | | |
| D(v 0.1), µm | 0.7 ± 0.01 | 0.7 ± 0.00 | 0.8 ± 0.01 | 0.8 ± 0.03 |
| D(v 0.5), µm | 1.7 ± 0.04 | 1.8 ± 0.02 | 1.8 ± 0.03 | 1.8 ± 0.05 |
| D(v 0.9), µm | 3.4 ± 0.06 | 3.6 ± 0.03 | 3.6 ± 0.07 | 3.5 ± 0.08 |
| Morphology | Collapsed spheres | Collapsed spheres | Collapsed spheres | Collapsed spheres |
| Water Content, Wt. % | 0.29 ± 0.01 | 1.65 ± 0.07 | 2.18 ± 0.02 | 0.39 ± 0.03 |
| Residual Solvent Wt. % | 0.09 | 0.43 | 0.21 | 0.07 |
| Physical State | Crystalline leucine Crystalline mannitol | Crystalline leucine Amorphous trehalose | Crystalline leucine Amorphous trehalose | Crystalline leucine Crystalline mannitol |
| Moisture sorption | Event at 50% RH | Event at 60% RH | Event at 60% RH | In-Process |
| Thermal Properties | | | | |
| $T_g$, ° C. | Not detected | 83 | 83 | Not detected |
| $T_m$, ° C. | 64, 164 | 64 | 64 | 64, 162 |

3.1. Particle Size Distributions

Figure 25:
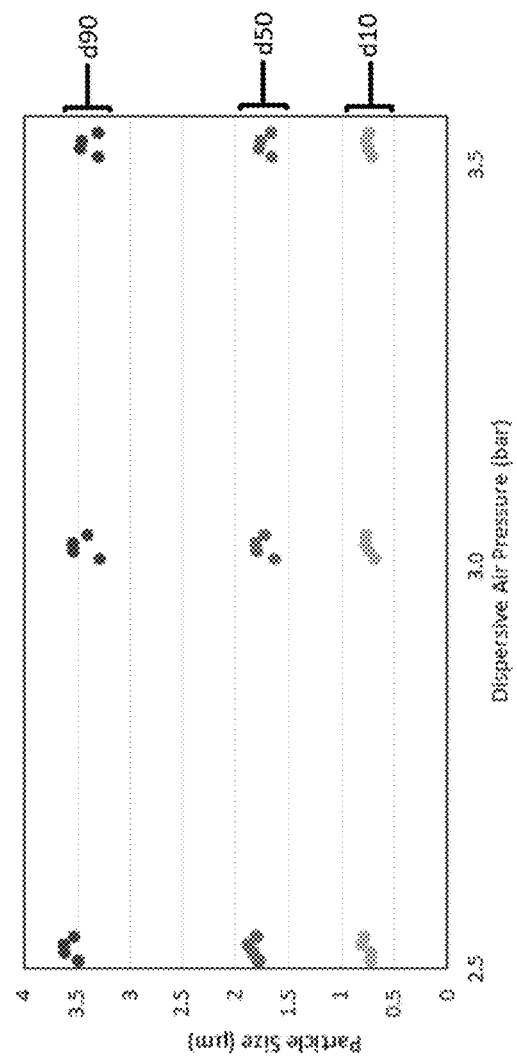
FIG. 25 is a graph showing pressure titration of spray dried treprostinil palmitil dry powder formulations A, B, C, and D. For visibility, data points are offset in order (A, B, C and D), within each air pressure category (left to right).
Figure 26:
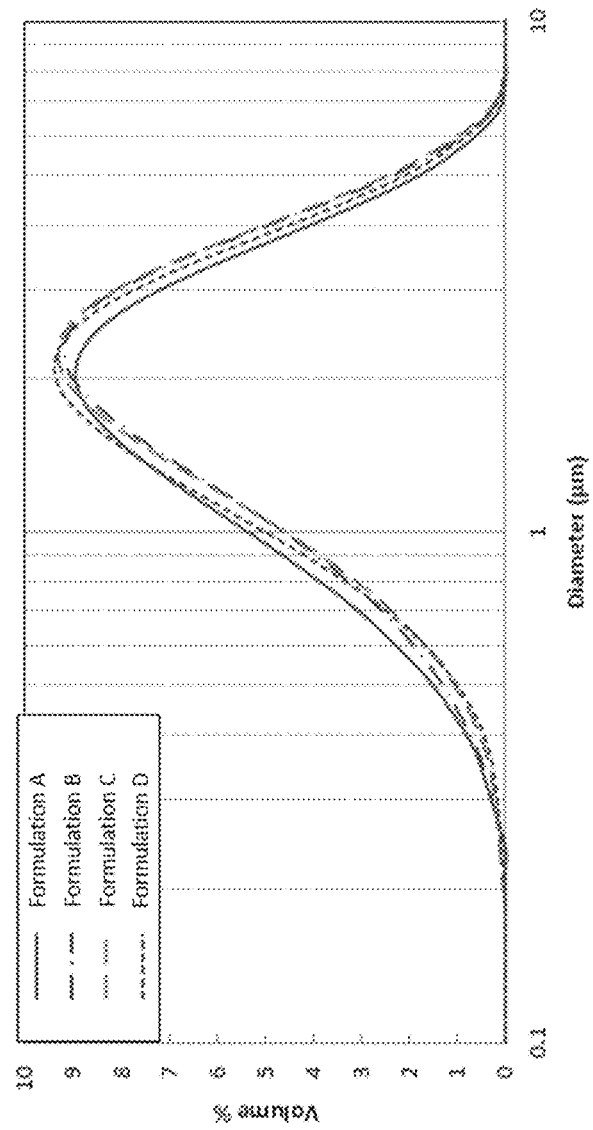
FIG. 26 is a graph showing particle size distributions of treprostinil palmitil dry powder formulations A, B, C, and D.
Figure 28:
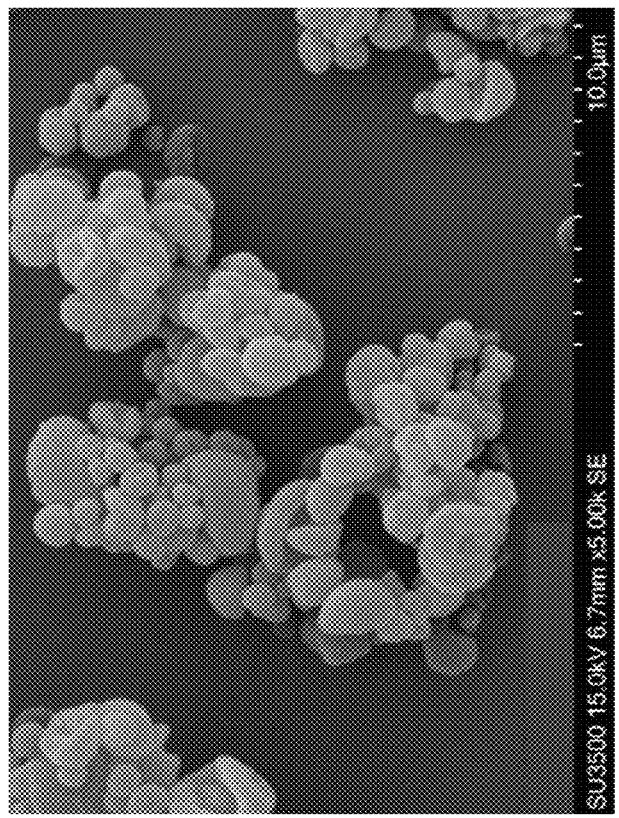
FIG. 28 is an SEM image of treprostinil palmitil dry powder formulation B.
Figure 27:
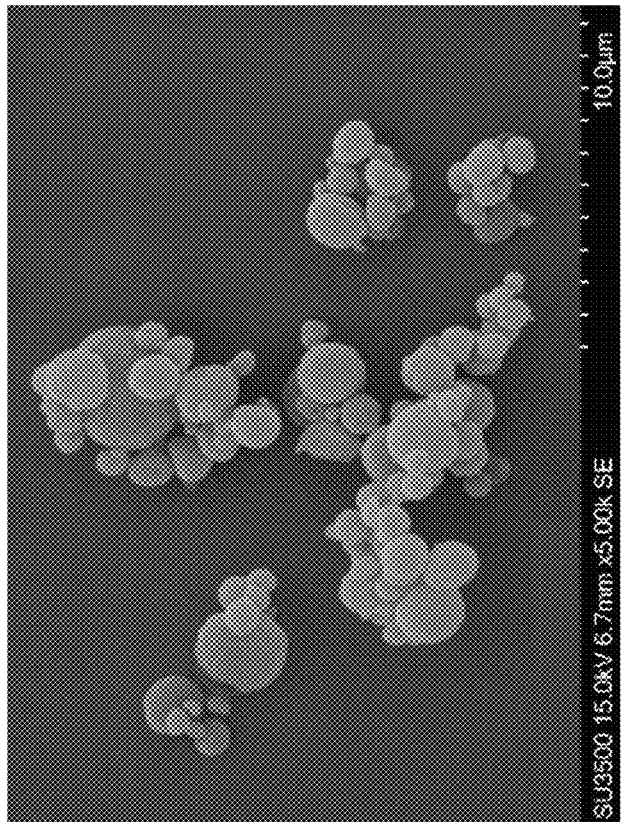
FIG. 27 is an SEM image of treprostinil palmitil dry powder formulation A.

As these formulations were targeted for respiratory delivery, the target particle size was to be less than 5 am. Particle size distributions were measured by laser diffraction on the Malvern Mastersizer 2000 with the Scirocco 2000 dry powder dispersion unit. An initial pressure titration screening on all samples was performed for method development (n=1), and it was observed that the results were almost identical between the three dispersive air pressures used (2.5, 3.0 and 3.5 bars) (FIG. 25). Based on this initial screen, an additional 2 replicates (n=2) were meas leucine (C and D) had lower residual 1-propanol as well as formulations containing mannitol (A and D).

TABLE 29

Residual Solvent

| Formulation | 1-Propanol Content (wt. %) | |
|---|---|---|
| | Wt % | PPM |
| A | 0.09 | 900 |
| B | 0.43 | 4300 |
| C | 0.21 | 2100 |
| D | 0.07 | 700 |

3.5. Powder X-Ray Diffraction

Sample crystallinity was assessed using a Rigaku MiniFlex 600 Powder X-ray diffractometer. Samples were prepared on 0.2 mm Zero Background Holder (ZBH) discs and run on the instrument from 3 to 40 2θ. Formulations A and D exhibited crystalline mannitol (likely polymorphic mixture) and leucine while formulations B and C exhibited crystalline leucine with amorphous trehalose.

Components may exhibit different diffraction intensities as neat material compared with a spray dried formulation. Formulations containing mannitol appeared to have similar diffraction patterns. Trehalose containing formulations also appeared to have similar amorphous diffraction patterns.

3.6. Differential Scanning Calorimetry (DSC)

Thermal transitions can be used to predict stability of the formulation. The four formulations were scanned on a TA Instruments Q2000 differential scanning calorimeter. Samples were equilibrated in a dry environment (<5% RH) overnight before they were hermetically sealed and run on the instrument. The modulation was set to +1.5° C./min with a heating ramp rate of 2.5° C./min from 0 to 180° C. A thermal event at 64° C. was observed for all the samples, and this event may correspond with the melt of treprostinil palmitil or DSPE-PEG2000.

No crystallization events were observed for the samples, a positive indicator for thermal stability. No glass transitions were detected for the mannitol-based formulations (A and D), supporting the powder X-ray diffraction (PXRD) results for crystalline material. Formulations A and D had a melt at 164° C., consistent with the melting temperature of mannitol. Formulations B and C exhibited glass transition at 83° C., likely due to amorphous trehalose. Formulation B also had thermal events at 133° C. and 158° C. not observed in other samples.

3.7. Thermal Gravimetric Analysis (TGA)

Thermal decomposition data for the formulations was measured using a TA Instruments Discovery Thermogravimetric Analyzer. Samples were run from 0 to 300° C. at a rate of 2.5° C./min. The formulations began to rapidly decompose after 180° C. Changes in weight were observed at around 100° C., corresponding with water content.

3.8. Dynamic Vapor Sorption

Water sorption and desorption profiles were measured on a Surface Measurement Systems DVS Advantage 1. Samples were run from 0 to 90% RH at 25° C. with step changes of 10% RH. All four formulations appeared to have a weight change event with an onset at around 50% or 60% RH, depending on the formulation. A second cycle was performed on the samples to assess water sorption rates post-crystallization. None of the samples was observed to change during the second cycle, and most samples did not retain water during the final desorption steps.

The sorption results from formulation D indicate a change at a higher humidity (around 70% RH) as compared to the results from formulation A. A slight loss in mass of formulation D was observed at around 50% RH compared with formulation A, which seemed to continually lose mass even with sorption of addition moisture from a higher humidity.

Uptake rate for the trehalose formulation indicates that it took approximately 50 to 90 minutes (depending on the level of leucine content) to reach moisture equilibration at a relative humidity of 40%. A lower leucine content took moisture faster than one with a higher leucine content.

3.9. Aerosol Performance of Capsules of Formulations a, C, and D Assessed by Aerodynamic Particle Size Distribution (APSD) by NGI Capsules of treprostinil palmitil dry powder formulations A, C, and D were stored for 1-3 months at 25° C. or 40° C. There was no change in the appearance of the encapsulated dry powder, e.g., no browning or obvious growth or change in hardness. Particle size distribution (PSD) of the dry powder formulations measured by laser diffraction was unaffected after 3 months of storage at 25° C. or 40° C.

Figure 31:
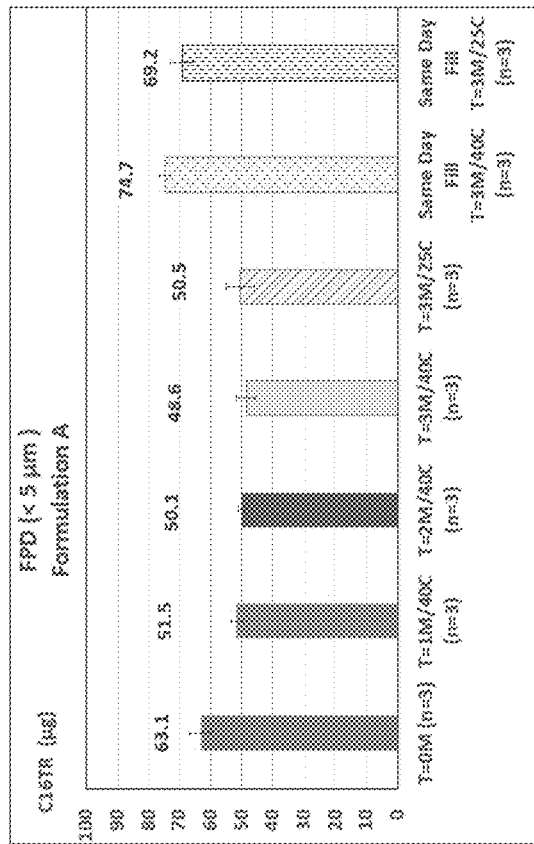
FIG. 31 is a graph showing the fine particle doses (FPD) of treprostinil palmitil dry powder formulation A at T=0 and after stored in capsules for 1-3 months at 25° C. or 40° C. as indicated, or after stored as bulk for 3 months at 25° C. or 40° C. and filled into capsules and dosed on the same day.
Figure 32:
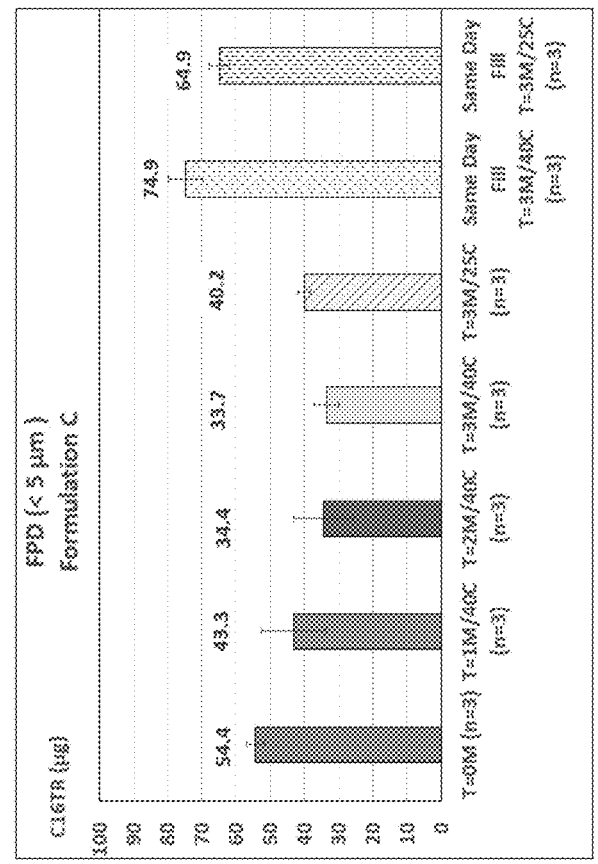
FIG. 32 is a graph showing the fine particle doses (FPD) of treprostinil palmitil dry powder formulation C at T=0 and after stored in capsules for 1-3 months at 25° C. or 40° C. as indicated, or after stored as bulk for 3 months at 25° C. or 40° C. and filled into capsules and dosed on the same day.
Figure 33:
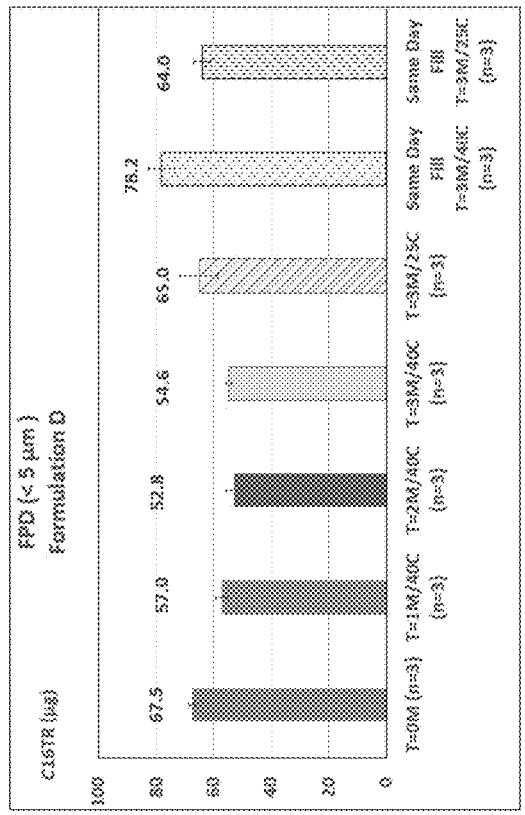
FIG. 33 is a graph showing the fine particle doses (FPD) of treprostinil palmitil dry powder formulation D at T=0 and after stored in capsules for 1-3 months at 25° C. or 40° C. as indicated, or after stored as bulk for 3 months at 25° C. or 40° C. and filled into capsules and dosed on the same day.

Treprostinil palmitil dry powder formulations A, C, and D were encapsulated, and the capsules were stored for 1 month, 2 months, or 3 months at 40° C., or were stored for 3 months at 25° C. The fine particle doses (FPDs) of the formulations from the stored capsules as well as the initial (T=0) FPDs of the formulations were measured by NGI. Treprostinil palmitil dry powder formulations A, C, and D were also stored as bulk for 3 months at 40° C. or 25° C., and were then filled into capsules and dosed for FPD determination on the same day. The FPD results for formulations A, C, and D are shown in FIGS. 31, 32, and 33, respectively. These data indicate that formulation D had the least change in FPD (−3.7%) after stored in capsules for 3 months at 25° C. Additionally, formulation D had a −5.2% change in FPD when stored as bulk for 3 months at 25° C. and filled into capsules and dosed on the same day. Furthermore, for each of formulations A, C, and D, storage at 40° C. did not appear predictive of long term storage at 25° C. for aerosol performance as measured by FPD. Based on these data, no conditioning or pretreatment of powder or capsules to modify aerosol performance is needed.

The emitted doses and total recovery rates of formulations A, C, and D from the capsules described above were also determined, with the results shown in Table 30.

TABLE 30

Emitted doses (as % of loaded dose) and total recovery rates of encapsulated treprostinil palmitil dry powder formulations A, C, and D

| Formulation | Conditions | % Emitted dose | % Total recovery |
|---|---|---|---|
| A | T = 0 M (n = 3) | 73.9 | 92.1 |
| | T = 1 M/40° C. (n = 3) | 64.2 | 81.8 |
| | T = 2 M/40° C. (n = 3) | 64.6 | 83.0 |
| | T = 3 M/40° C. (n = 3) | 66.0 | 85.8 |
| | T = 3 M/25° C. (n = 3) | 66.6 | 85.4 |
| | Same Day Fill T = 3 M/40° C. (n = 3) | 81.7 | 97.8 |
| | Same Day Fill T = 3 M/25° C. (n = 3) | 79.0 | 93.6 |
| C | T = 0 M (n = 3) | 65.7 | 96.3 |
| | T = 1 M/40° C. (n = 3) | 56.5 | 94.2 |
| | T = 2 M/40° C. (n = 3) | 46.8 | 91.4 |
| | T = 3 M/40° C. (n = 3) | 45.8 | 103.7 |
| | T = 3 M/25° C. (n = 3) | 52.1 | 93.9 |

TABLE 30-continued

Emitted doses (as % of loaded dose) and total recovery rates of encapsulated treprostinil palmitil dry powder formulations A, C, and D

| Formulation | Conditions | % Emitted dose | % Total recovery |
|---|---|---|---|
| | Same Day Fill T = 3 M/40° C. (n = 3) | 80.0 | 99.5 |
| | Same Day Fill T = 3 M/25° C. (n = 3) | 77.9 | 98.3 |
| D | T = 0 M (n = 3) | 81.8 | 98.0 |
| | T = 1 M/40° C. (n = 3) | 75.0 | 94.1 |
| | T = 2 M/40° C. (n = 3) | 72.8 | 92.9 |
| | T = 3 M/40° C. (n = 3) | 74.6 | 92.4 |
| | T = 3 M/25° C. (n = 3) | 80.4 | 98.4 |
| | Same Day Fill T = 3 M/40° C. (n = 3) | 88.3 | 106.0 |
| | Same Day Fill T = 3 M/25° C. (n = 3) | 79.9 | 96.6 |

The data above indicate that formulation D displayed the least change in emitted dose after stored in capsules for 3 months at 25° C., and after stored as bulk for 3 months at 25° C. and then filled into capsules and dosed on the same day. Taken together, based on the changes in the aerosol performance, formulation D appears stable for at least for 3 months at 25° C. Additionally, the stability data up to date supports a 6 months shelf life when stored at 2-8° C.

Example 3—Determination of Aerosol Performance of Trahalose-Based Treprostinil Palmitil Dry Powder Formulation Under Accelerated Storage Condition and Lung Pharmacokinetic Profile in Rats Following Inhalation of the Dry Powder Formulation Trahalose-based treprostinil palmitil dry powder composed of treprostinil palmitil, DSPE-PEG2000, trehalose (Treh) and leucine (Leu) in the weight ratio of 1:0.5:70:30 was produced by spray drying using a Buchi B-290 system as described in Example 1. The dry powder was stored in sealed glass vials at 40° C. and uncontrolled ambient humidity for an accelerated stability study. The aerosol performance of the powder was measured after 1.5, 2.5, and 3.5 months of storage.

Methods and Materials

1. Dynamic Vapor Sorption (DVS) Study

The moisture absorption curve was obtained using the Dynamic Vapor Sorption (DVS) automated gravimetric sorption system (DVS Intrinsic1 Plus, Surface Measurement System, PA, USA). Approximately 20 mg of powder was loaded, and subjected to a cycle of sorption/desorption isotherm (from 0% relative humidity (RH) to 90% RH to 0% RH again, in increments of 10% RH) at 25° C. The change in powder mass (%) with RH was determined and plotted.

2. DPI Device & Aerodynamic Particle Size Distribution (APSD) Testing

RS01 Mod.7 DPI Device (High Resistance, code 239700002AA, Plastiape, Italy) was used in this study. Mass median aerodynamic diameter (MMAD) of the trehalose-based treprostinil palmitil dry powder was measured using the Next Generation Impactor (NGI) at 60 L/min.

Approximately 15 mg of the treprostinil palmitil dry powder was loaded into a Size #3 HPMC capsule (Qualicaps, Inc.). This capsule was loaded into the DPI device and actuated to characterize the aerosol particle size distribution (APSD). The drug amount deposited on each impactor stage and filter was analyzed by High Performance Liquid Chromatography (HPLC).

3. Nose-Only Inhalation

The treprostinil palmitil dry powder was delivered through a 12-port nose-only inhalation chamber using a dry powder dispenser (Vilnius Aerosol Generator (VAG), CH Technologies, USA). Approximately 1 g of the dry powder was loaded into the VAG. The VAG had a flow rate of 8 L/min at 1.0 V for a total of 20 minutes. The dry powder delivery system was described in more detail in Li et al., "Inhaled INS1009 Demonstrates Localized Pulmonary Vasodilation," European Respiratory Society (ERS) International Congress, 3-7 Sep. 2016, London, United Kingdom, Abstract No: 853952 (poster PA2845), the content of which is incorporated herein by reference in its entirety.

4. PK Sample Collection and Analysis

Rat lung tissues were harvested immediately post delivery (~0.5 hr), 6, 12, and 24 hrs after drug dosing. Lung tissue samples were analyzed for treprostinil palmitil and treprostinil (TRE) by LC-MS/MS. Results are reported in terms of "Treprostinil Palmitil Equivalents" to account for postmortem hydrolysis of treprostinil palmitil.

Treprostinil Palmitil Equivalents, ng/g=[Treprostinil Palmitil, ng/g]+[TRE, ng/g]*(MM treprostinil palmitil/ MM TRE)

MM: molar mass

Results

1. Dynamic Vapor Sorption (DVS)

Figure 34:
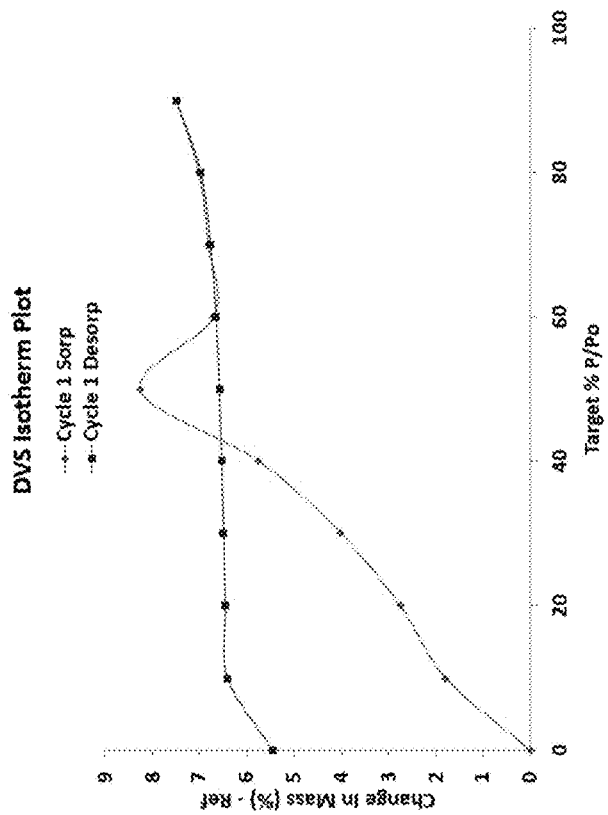
FIG. 34 is a dynamic vapor sorption (DVS) isotherm plot of the trehalose-based C16TR (treprostinil palmitil) dry powder formulation.

Dynamic vapor sorption (DVS) of the treprostinil palmitil dry powder formulation is shown in FIG. 34. When the dry powder was exposed to an increase in RH up to 50%, the absorbed moisture increased from 0% to more than 8% and was not completely reversible with desorption, remaining at or above 5.5%. To keep moisture content at or below approximately 4%, the RH exposure for this powder may be controlled to <30% during manufacture.

2. Aerodynamic Particle Size Distribution (APSD)

Figure 35:
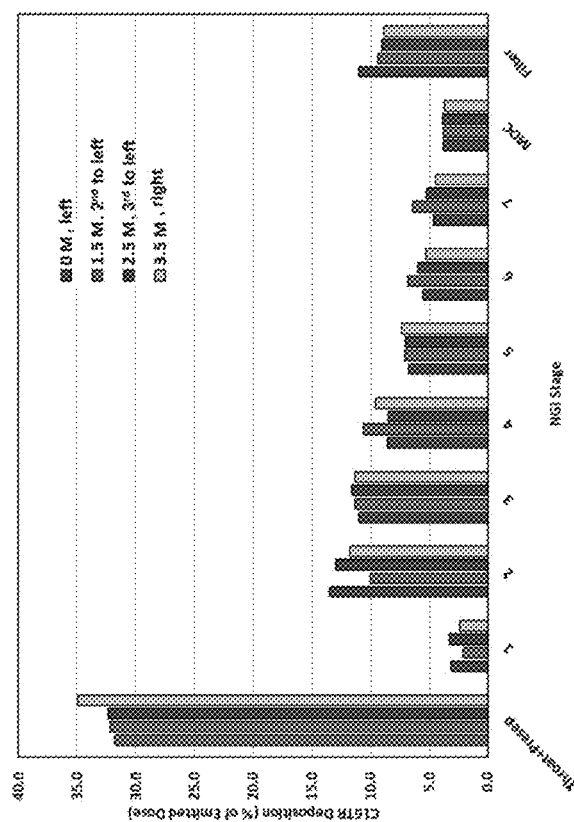
FIG. 35 is a graph showing the aerosol particle size distribution of the trehalose-based C16TR (treprostinil palmitil) dry powder formulation at T=0 month, and after stored at 40° C. and uncontrolled ambient humidity for 1.5 months, 2.5 months, and 3.5 months (n=1 per time point).

The APSD data of the treprostinil palmitil dry powder stored for 1.5 months (T=1.5M), 2.5 months (T=2.5M), and 3.5 months (T=3.5M), as well as the initial APSD (T=0) obtained by RS01 Mod. 7 DPI (high resistance) at 60 L/min are shown in FIG. 35 and Table 31. The distributions from all four time points were comparable.

TABLE 31

Aerodynamic particle size distribution (APSD) data of trehalose-based treprostinil palmitil dry powder at various time points following storage at 40° C.

| Treprostinil Palmitil Deposition, % of Emitted Dose | Time Point | | | |
|---|---|---|---|---|
| NGI Stage | 0 M | 1.5 M | 2.5 M | 3.5 M |
| Throat + Presep | 31.8 | 32.2 | 32.3 | 35 |
| Stage 1 | 3.2 | 2.1 | 3.3 | 2.4 |
| Stage 2 | 13.5 | 10.1 | 13 | 11.8 |
| Stage 3 | 11 | 11.3 | 11.6 | 11.3 |
| Stage 4 | 8.6 | 10.7 | 8.5 | 9.6 |
| Stage 5 | 6.8 | 7.1 | 7 | 7.4 |
| Stage 6 | 5.6 | 6.9 | 6 | 5.3 |
| Stage 7 | 4.7 | 6.4 | 5.2 | 4.5 |
| MOC | 3.8 | 3.9 | 3.9 | 3.7 |
| Filter | 11 | 9.4 | 9 | 8.9 |

The fine particle fraction (FPF), MAD and geometric standard deviation (GSD) values of the aerosolized dry powder after storage at 40° C. and uncontrolled ambient humidity for up to 3.5 months are summarized in Table 32.

The FPF values ranged from 54.6% to 58.7%. The MMAD values ranged from 1.25 μm to 1.44 μm. The GSD values ranged from 3.5 to 4.1.

TABLE 32

The FPF, MMAD and GSD values of aerosolized trehalose-based treprostinil palmitil dry powder after storage at 40° C. and uncontrolled ambient humidity for up to 3.5 months

|  | Initial (T = 0) | 1.5 month | 2.5 months | 3.5 months |
|---|---|---|---|---|
| FPF (%) | 55.9 | 58.7 | 55.5 | 54.6 |
| MMAD (μm) | 1.37 | 1.25 | 1.44 | 1.39 |
| GSD | 4.11 | 3.51 | 3.92 | 3.64 |

3. Rat Lung PK Results

Figure 36:
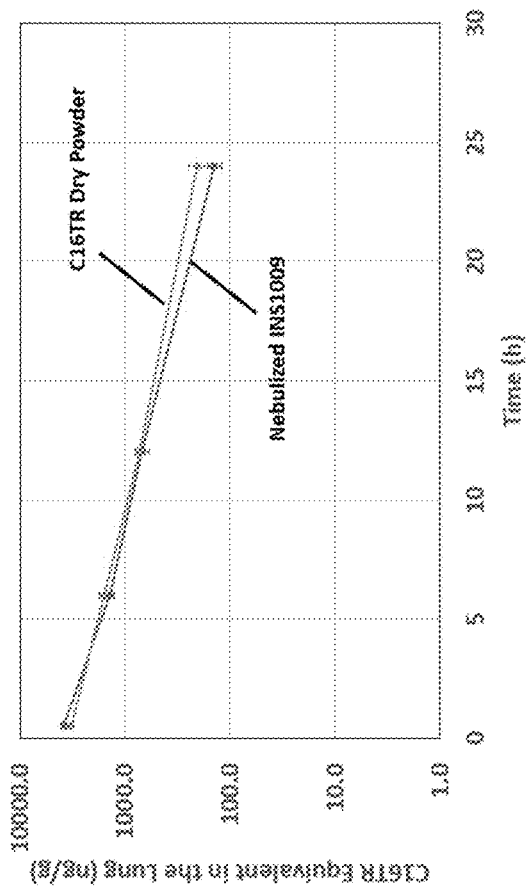
FIG. 36 is a graph showing the concentration of C16TR (treprostinil palmitil) equivalent (C16TR (treprostinil palmitil) plus treprostinil, ng/g) in the lung after inhalation of the trehalose-based C16TR (treprostinil palmitil) dry powder formulation and nebulized INS1009.

The concentration of treprostinil palmitil equivalent (treprostinil palmitil plus treprostinil) in the lung after inhalation of nebulized INS1009 or the aerosolized treprostinil palmitil dry powder is summarized in Table 33 and FIG. 36. The nebulized INS1009 contained treprostinil palmitil and the excipients squalane and DSPE-PEG2000 at a molar ratio of 45:45:10, suspended in PBS (see Corboz et al., "Preclinical Pharmacology and Pharmacokinetics of Inhaled Hexadecyl-Treprostinil (C16TR), a Pulmonary Vasodilator Prodrug," J Pharmacol Exp Ther. 363:348-357 (2017), the content of which is incorporated herein by reference in its entirety). Both nebulized INS1009 and the C16TR (treprostinil palmitil) dry powder had similar lung PK profiles following inhalation in rats. The statistical comparison of these two profiles is summarized in Table 34, demonstrating comparable slopes for both profiles.

TABLE 33

Concentration profile (ng/g) of treprostinil palmitil equivalent (treprostinil palmitil plus treprostinil molar equivalent, ng/g) in the rat lung after inhalation of the trehalose-based treprostinil palmitil dry powder or nebulized INS1009

|  | Nebulized INS1009 | | | Trehalose-based treprostinil palmitil dry powder | | |
|---|---|---|---|---|---|---|
| Time (h) | Mean (ng/g) | SEM | No. of Rats | Mean (ng/g) | SEM | No. of Rats |
| 0.5 | 3888.5 | 220.1 | 3 | 3330.7 | 253.6 | 6 |
| 6 | 1389.6 | 108.8 | 2 | 1582.3 | 186.6 | 4 |
| 12 | 690.3 | 95.5 | 3 | 729.1 | 68.8 | 6 |
| 24 | 141.7 | 22.3 | 3 | 205.0 | 41.0 | 6 |

*SEM: Standard Error of the Mean

TABLE 34

Statistical analysis of the PK profile for the treprostinil palmitil equivalent concentration in the rat lung after inhalation of the trehalose-based treprostinil palmitil dry powder and nebulized INS1009

Equation: y = a + b*x

| Formulation | Nebulized INS1009 | Trehalose-based treprostinil palmitil dry powder |
|---|---|---|
| Slope | −0.064 ± 0.006 | −0.055 ± 0.003 |
| Pearson's r | −0.99 | −1.00 |

Taken together, this study indicates that the aerosol particle size distribution of the trehalose-based treprostinil palmitil dry powder formulation is reproducible for up to 3.5 months of storage at 40° C. in sealed vials and uncontrolled RH, and that the lung PK profile of the treprostinil palmitil dry powder formulation was comparable to that of the nebulized INS1009.

Example 4—Pharmacokinetic Evaluations of Mannitol and Trehalose-Based Treprostinil Palmitil Dry Powder Formulations in Rats In this study, the lung and plasma pharmacokinetics (PK) of two different treprostinil palmitil-dry powder formulations with mannitol (i.e., formulation D as described in Example 2) or trehalose (i.e., formulation C as described in Example 2) as their major excipients were evaluated. The compositions of formulations D and C expressed in weight ratios, targeted weight percentages calculated based on the weight ratios, and actual weight percentages of the components from a typical batch of each formulation are summarized in Tables 35A and 35B3, respectively.

TABLE 35A

Composition of formulation D in weight ratio, targeted weight percentages, and actual weight percentages of components from a typical batch

| Composition Treprostinil Palmitil/DSPE-PEG2000/Man/Leu Wt ratio | Composition Wt % | | | | |
|---|---|---|---|---|---|
|  | Treprostinil Palmitil | DSPE-PEG2000 | Mannitol | Leucine | Total |
| 1.5/0.75/70/30 | Targeted | | | | |
|  | 1.47 | 0.73 | 68.46 | 29.34 | 100 |
|  | Actual* | | | | |
|  | 1.50 | 0.75 | 68.45 | 29.30 | 100 |

*The actual wt % values shown are typical wt % values for the components in treprostinil palmitil dry powder formulation D. Batches of formulation D with wt % for each component independently varying at or within ±5% of the typical wt % value as shown were observed to have equivalent properties and performance.

TABLE 35B

Composition of formulation C in weight ratio, targeted weight percentages, and actual weight percentages of components from a typical batch

| Composition Treprostinil Palmitil/DSPE-PEG2000/Treh/Leu Wt ratio | Composition Wt % | | | | |
|---|---|---|---|---|---|
| | Treprostinil Palmitil | DSPE-PEG2000 | Trehalose | Leucine | Total |
| 1.5/0.75/70/30 | | | Targeted | | |
| | 1.47 | 0.73 | 68.46 | 29.34 | 100 |
| | | | Actual** | | |
| | 1.50 | 0.75 | 67.59 | 30.16 | 100 |

**The actual wt % values shown are typical wt % values for the components in treprostinil palmitil dry powder formulation C. Batches of formulation C with wt % for each component independently varying at or within ±5% of the typical wt % value as shown were observed to have equivalent properties and performance.

Methods

Male Sprague Dawley rats (300-400 g) were exposed to aerosols of dry powder formulation D or formulation C using a 12-port nose-only inhalation chamber and a Vilinius Aerosol Generator (VAG). The rats were placed in restraining tubes that were attached to the nose-only ports in the chamber. In two separate studies with formulation D and formulation C, 9 rats were used in each study, and 1 port was used for collection of aerosol drug on a filter. An abbreviated study was also performed with formulation D in which 6 rats were used, and 1 port was used for the collection of drug amount deposited on a filter.

For the drug exposures, one gram of material was placed in the VAG. Output from the VAG was established at 1 Volt (V) and the drug was dispersed and delivered into the nose-only chamber with a bias airflow of 8 L/min. The air entered the bottom of the nose-only chamber and exited at the top. The duration of exposure was set at 20 min. A vacuum source (0.5 L/min) was attached to the filter and the drug sampling time was established at 5 min. The amount of treprostinil palmitil deposited on the filter was measured by HPLC and a charged aerosol detector (CAD). The delivered drug dose was calculated from the concentration of drug inhaled (from filter data), the duration of exposure, respiratory minute volume and body weight with a deposition fraction of 1.0 used for the drug delivered at the nose, and a deposition fraction of 0.1 used for the drug delivered to the lungs. Doses are expressed per kg body weight.

In the two primary studies with formulation D and formulation C, blood samples were collected at times of 0.5, 2, 4, 6, 12 and 24 hours after drug exposure. The blood samples were centrifuged to extract the plasma. In these studies, respiratory tissues of the larynx, trachea, carina+bronchi and lungs were collected at times of 0.5, 6, 12 and 24 hours after drug exposure.

In the abbreviated study with formulation D, blood samples were obtained at times of 0.5, 2, 4, 12 and 24 hours and respiratory tissues were harvested at times of 0.5 and 24 hours after drug exposure. The concentrations of treprostinil (TRE) in the plasma and treprostinil palmitil and TRE in respiratory tissues were measured by LC-MS/MS. For all respiratory tissues, the treprostinil palmitil (C16TR) equivalent (C16TReq) concentration was derived from the treprostinil palmitil and TRE concentrations (C16TReq=treprostinil palmitil+[TRE×615/390.5 ng/g]), where 615 and 390.5 are the molecular weights of treprostinil palmitil and TRE, respectively. The lung treprostinil palmitil equivalent and plasma TRE data were used to derive the following PK parameters: lambda z (terminal elimination rate constant), $T_{1/2}$, $T_{max}$, $C_{max}$ and $AUC^{0-inf}$ using the PK Solver program in Microsoft Excel.

Results

Exposure of rats to formulation D and formulation C resulted in a slightly higher total delivered dose of 78 µg/kg body weight with formulation D compared to a total delivered dose of 58 µg/kg body weight with formulation C. The concentration of treprostinil palmitil equivalent in the lungs, measured at 0.5 hours after exposure, was also slightly higher with formulation D and averaged 3072 ng/g compared to 1711 ng/g with formulation C.

Figure 37:
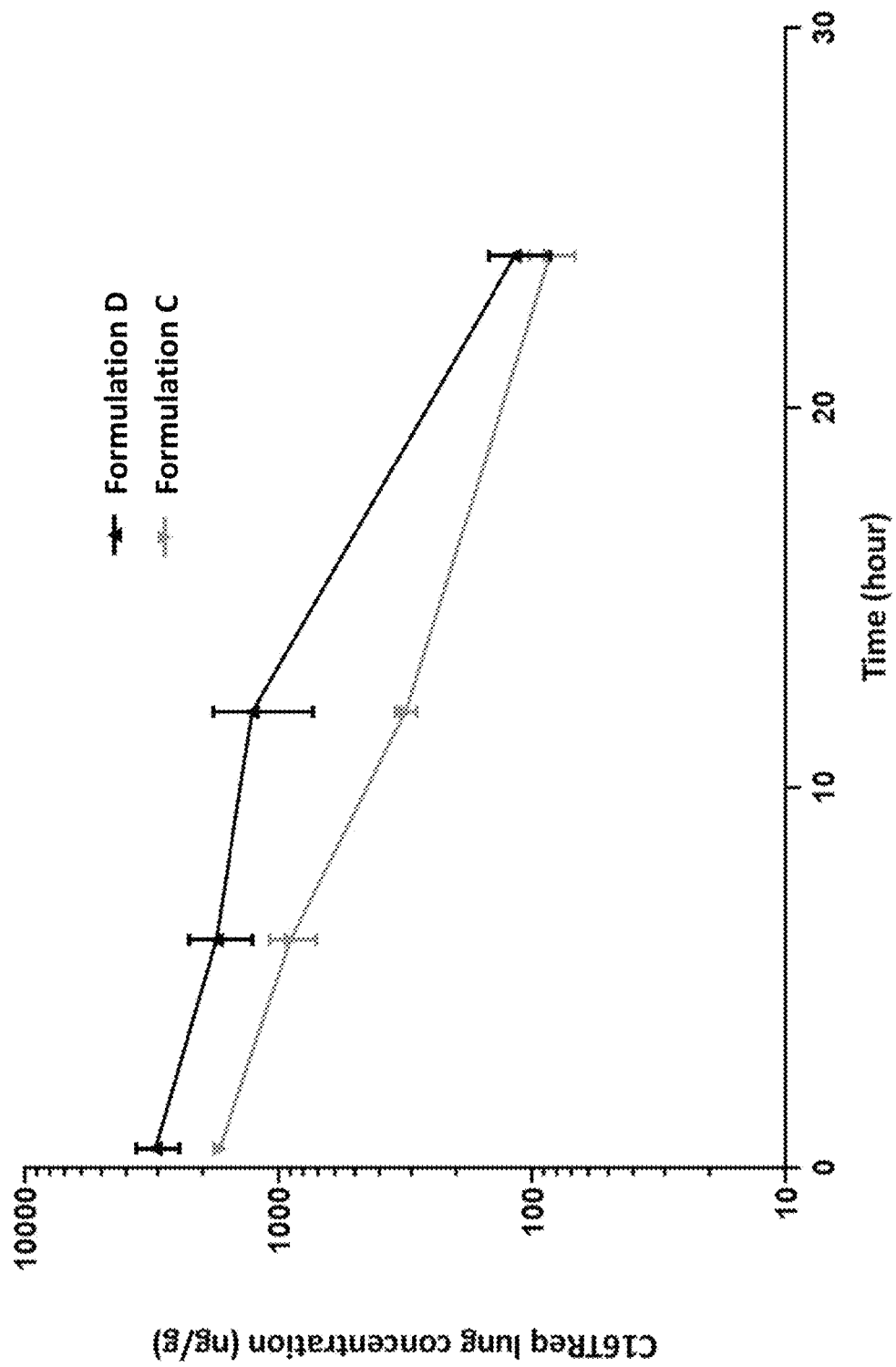
FIG. 37 is a graph showing the concentration of C16TR (treprostinil palmitil) equivalent (C16TReq) in the lungs after inhaled treprostinil palmitil dry powder formulation D or formulation C.
Figure 38:
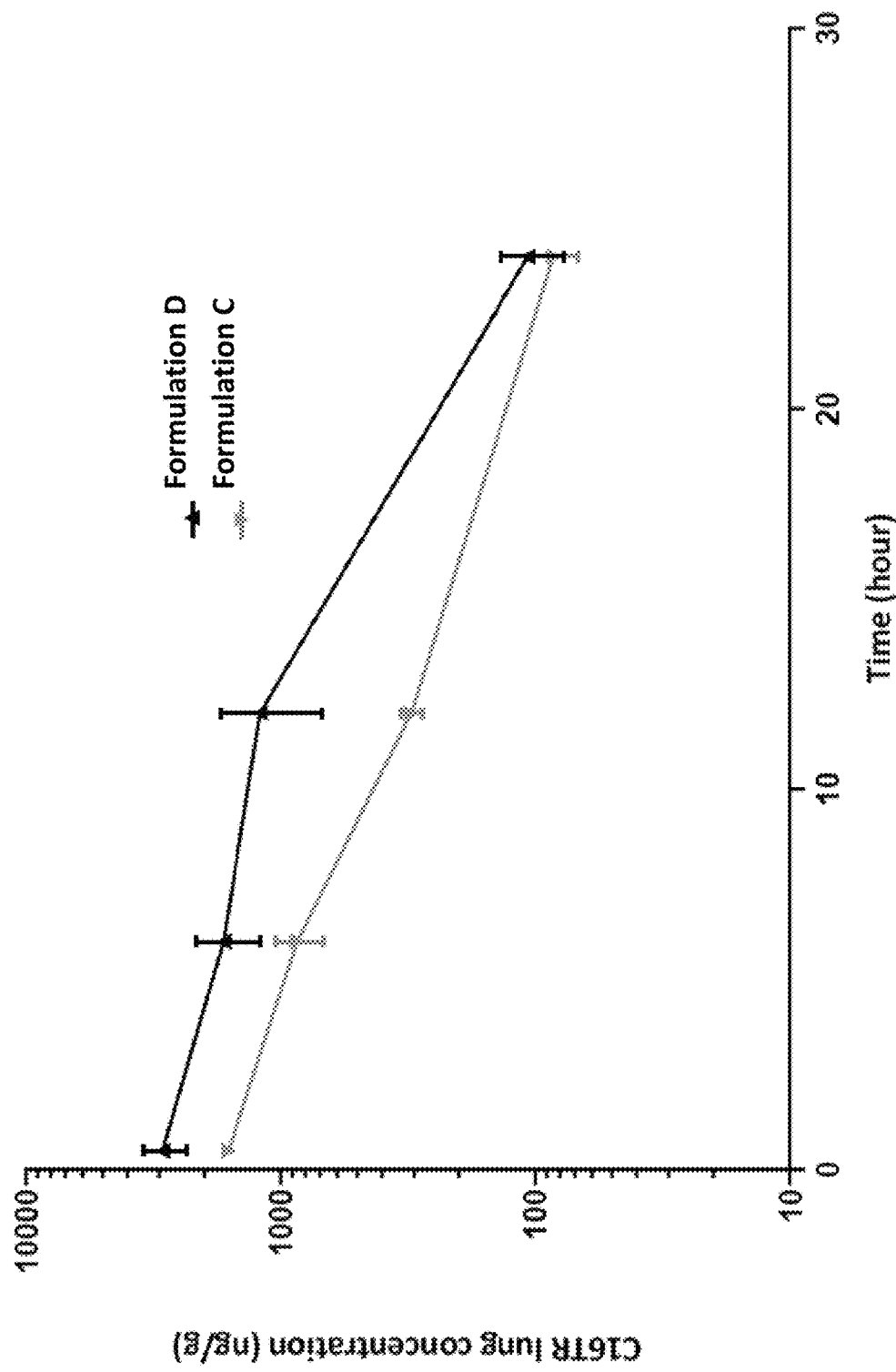
FIG. 38 is a graph showing the concentration of C16TR (treprostinil palmitil) in the lungs after inhaled treprostinil palmitil dry powder formulation D or formulation C.
Figure 39:
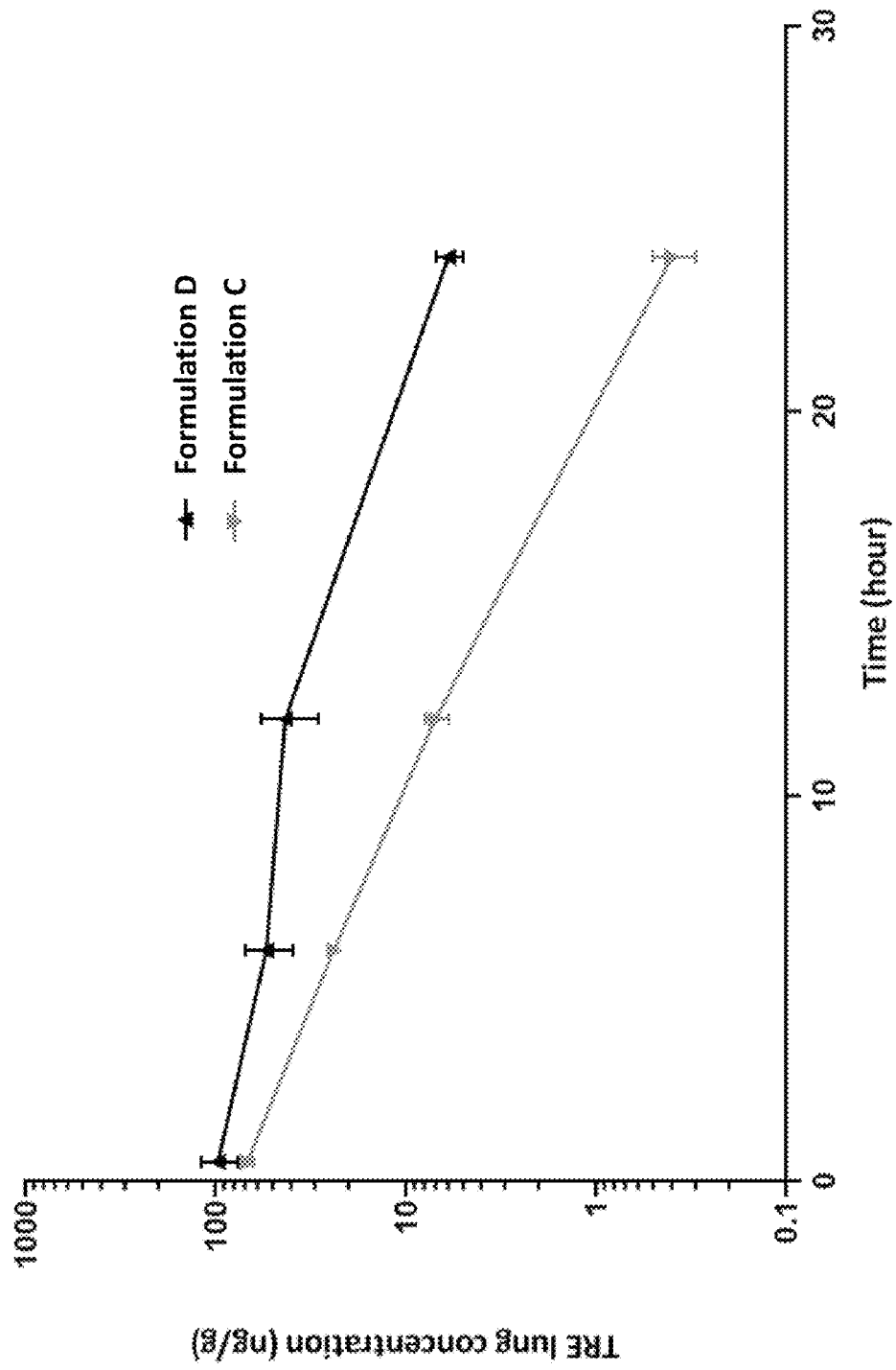
FIG. 39 is a graph showing the concentration of TRE in the lungs after inhaled treprostinil palmitil dry powder formulation D or formulation C.

1. Lung and Upper Airway Treprostinil Palmitil, TRE and Treprostinil Palmitil Equivalent With both formulation D and formulation C, the highest concentrations of treprostinil palmitil, TRE and treprostinil palmitil equivalent in the lungs occurred at 0.5 hours after exposure. There was a slow mono-exponential decline in treprostinil palmitil and TRE over 24-hours with the concentrations of both treprostinil palmitil and TRE consistently higher at all time points with formulation D. These results are illustrated for treprostinil palmitil equivalent (C16TReq) in FIG. 37, which shows the slow decline in lung treprostinil palmitil equivalent concentration over 24 hours with consistently higher concentrations of treprostinil palmitil equivalent with formulation D compared to formulation C. FIG. 38 shows the concentration of treprostinil palmitil (C16TR) in the lungs after inhaled formulation D or formulation C. FIG. 39 shows the concentration of TRE in the lungs after inhaled formulation D or formulation C.

A comparison of the derived PK parameters for lung treprostinil palmitil equivalent found no major difference between formulations D and C for lambda z, $T_{1/2}$ and $T_{max}$, but a 79% higher lung treprostinil palmitil equivalent $C_{max}$ and a 130% higher $AUC_{0-24\,h}$ for formulation D (Table 36).

TABLE 36

Pharmacokinetic parameters of lung treprostinil palmitil
equivalent after inhaled Formulation D and Formulation C

| Compound | lambda_z 1/h | $T_{1/2}$ h | $T_{max}$ h | $C_{max}$ ng/g | $AUC_{0-24\,h}$ µg/g*h | $AUC_{0-inf\_obs}$ µg/g*h |
|---|---|---|---|---|---|---|
| Formulation D | 0.139 | 4.98 | 0.5 | 3072 | 31.493 | 32.330 |
| Formulation C | 0.130 | 5.35 | 0.5 | 1711 | 13.674 | 14.331 |

Abbreviations: Lambda z, terminal elimination rate constant; $T_{1/2}$, half-life; $T_{max}$, time of maximal concentration; $C_{max}$, maximal concentration; $AUC_{0-24\,h}$, area under the concentration curve between time zero and 24-hours; $AUC_{0-inf\_obs}$, area under the concentration curve extrapolated to infinity.

For the deposition of treprostinil palmitil in the larynx, trachea, carina+bronchi and lungs, the majority of the treprostinil palmitil (>97 percent) was deposited in the lungs. This was noted with both formulation D and formulation C. Nasal tissue was not collected in this study.

2. Plasma TRE

Figure 40:
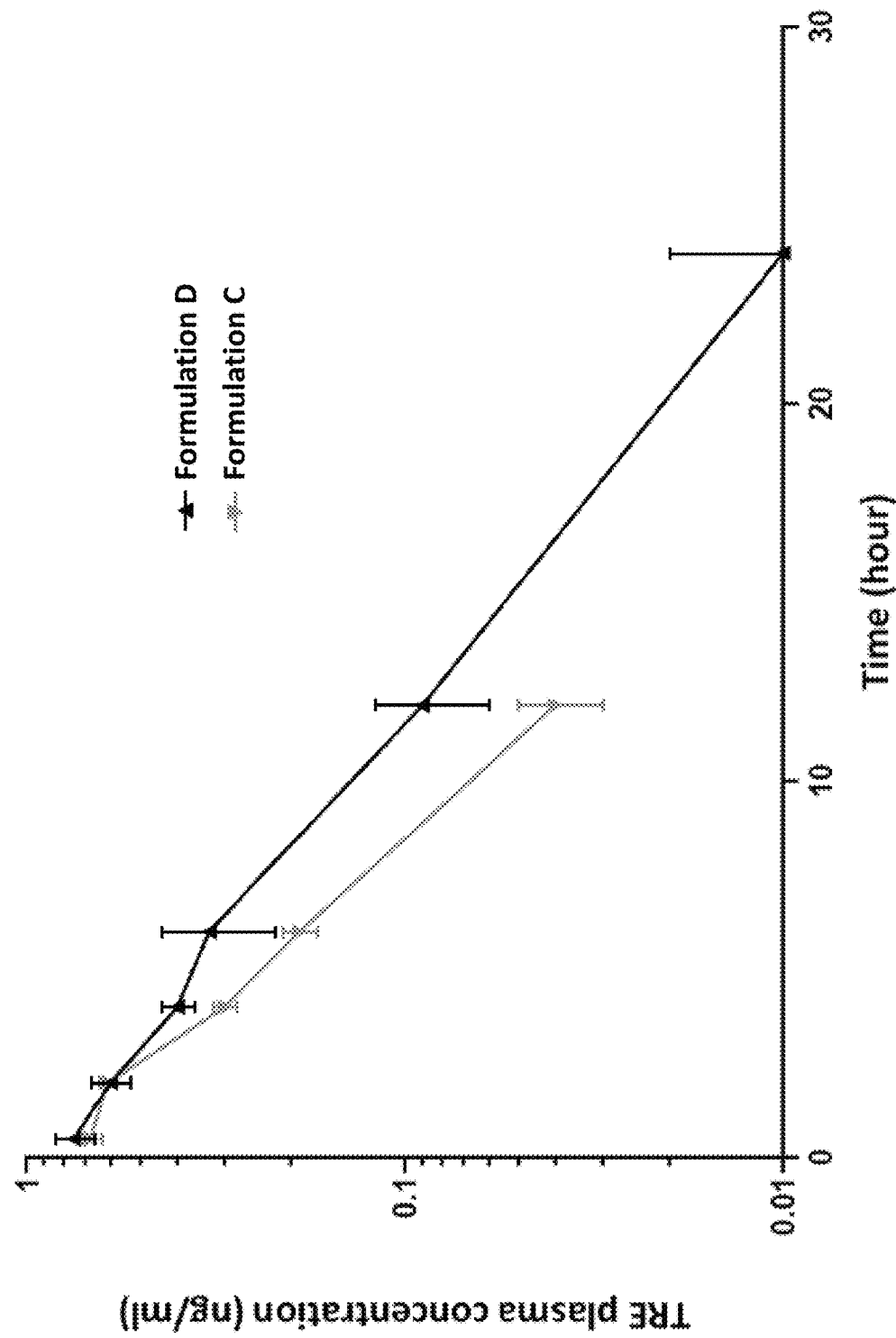
FIG. 40 is a graph showing the concentration of TRE in the plasma after inhaled treprostinil palmitil dry powder formulation D or formulation C.
Figure 41:
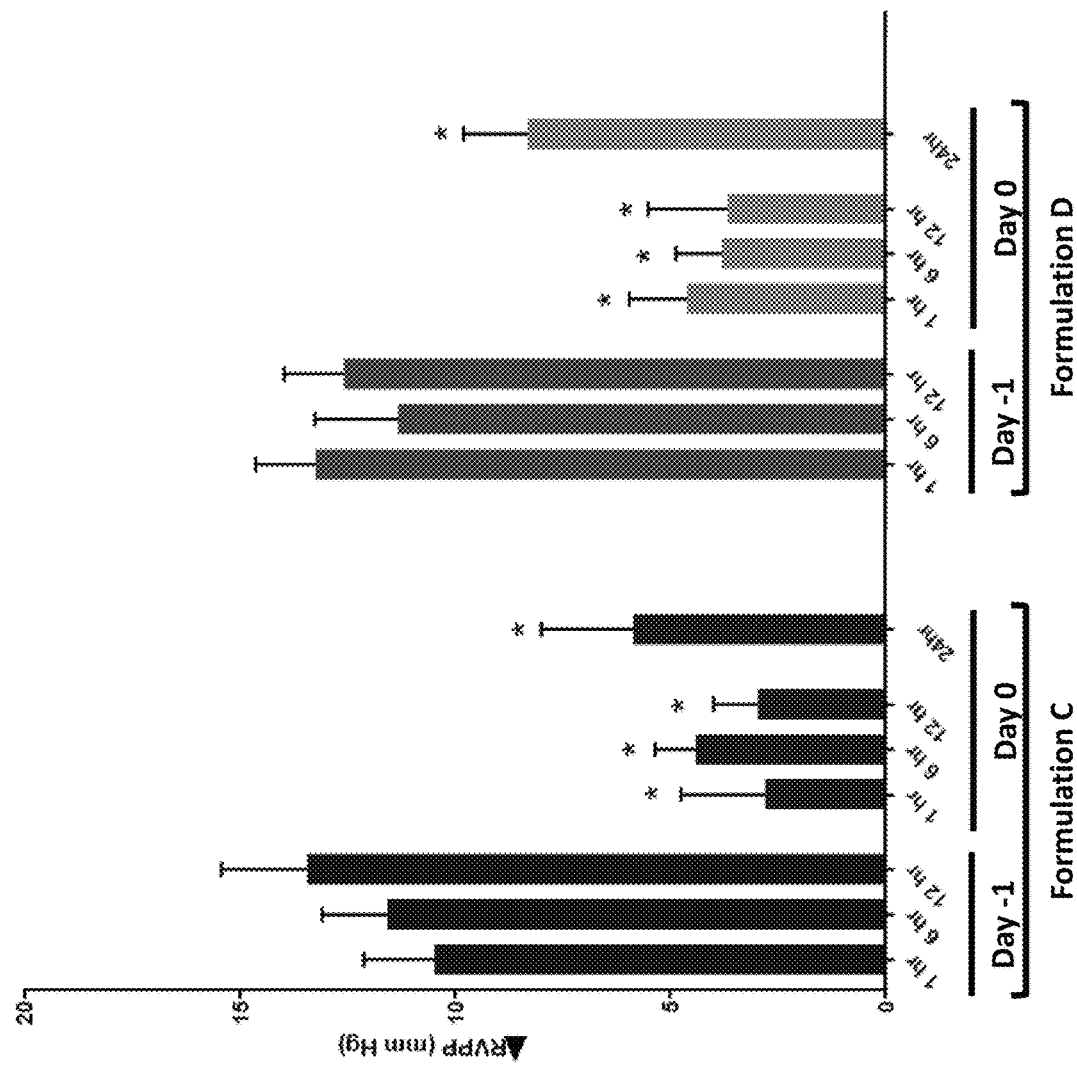
FIG. 41 is a graph showing the ARVPP response to hypoxic challenge in rats exposed to treprostinil palmitil dry powder formulation D or formulation C.

The highest concentration of TRE in the plasma was observed at 0.5 hours with a slow decline over 24 hours with formulation D and a more rapid decline with formulation C. Plasma TRE concentrations were below the level of detection by 24 hours with formulation C (FIG. 40).

A comparison of the derived PK parameters for plasma TRE found a 34% lower lambda z and a 51% higher T1/2 with formulation D compared to formulation C (Table 37). The plasma TRE $C_{max}$ was 10% higher and the $AUC_{0-t}$ 51% higher with formulation D compared to formulation C (Table 37).

TABLE 37

Pharmacokinetic parameters of plasma TRE after
inhaled formulation D and formulation C

| Compound | lambda_z 1/h | $T_{1/2}$ h | $T_{max}$ h | $C_{max}$ ng/mL | $AUC_{0-24\,h}$ ng/mL*h | $AUC_{0-inf\_obs}$ ng/mL*h |
|---|---|---|---|---|---|---|
| Formulation D | 0.174 | 3.980 | 0.5 | 0.748 | 4.846 | 4.922 |
| Formulation C | 0.261 | 2.652 | 0.5 | 0.682 | 3.223 | 3.366 |

Abbreviations: Lambda z, terminal elimination rate constant; $T_{1/2}$, half-life; $T_{max}$, time of maximal concentration; $C_{max}$, maximal concentration; $AUC_{0-24\,h}$ area under the concentration curve between time zero and 24-hours; $AUC_{0-inf\_obs}$, area under the concentration curve extrapolated to infinity.

In summary, inhalation of treprostinil palmitil dry powder formulations D and C results in low treprostinil plasma $C_{max}$ values and sustained levels of treprostinil in the plasma and lungs as compared to inhalation of treprostinil. A comparison of the PK profile in rats between formulation D and formulation C delivered under similar conditions i.e. a VAG output of 1 V for 20 min, resulted in a 34% higher delivered dose with formulation D that was 78 µg/kg compared to 58 µg/kg with formulation C. The concentrations of treprostinil palmitil, TRE and treprostinil palmitil equivalent in the lungs were consistently higher with formulation D, likely due to the higher delivered dose with formulation D, but both formulations demonstrated a slow, mono-exponential decline over 24 hours. A similar trend was observed with the concentrations of TRE in the plasma that were higher with formulation D, and with a slow decline over 24 hours with both formulations. Most of the TRE and treprostinil palmitil exposure occurred in the lungs with less than 3 percent deposited in the upper respiratory regions of the larynx, trachea, carina+bronchi.

These results with formulation D and formulation C demonstrate a PK profile that is similar to that previously observed with nebulized INS1009, which displays the highest concentrations of treprostinil palmitil equivalent in the lungs and TRE in the plasma by 30 min with their slow mono-exponential decline over 24 hours. However, there appears to be a significant difference in the lung treprostinil palmitil equivalent: plasma TRE $C_{max}$ ratio between the treprostinil palmitil dry powder formulations on the one hand and nebulized INS1009 on the other. Typical lung treprostinil palmitil equivalent: plasma TRE $C_{max}$ ratio for nebulized INS1009 is ~800, while the ratio for the treprostinil palmitil dry powder formulations ranges from ~1,600-13,000. See Corboz et al., J Pharmacol Exp Ther 363: 1-10 (2017), the content of which is incorporated herein by reference in its entirety. Since pulmonary vasodilation is associated more with local activity of TRE within the lungs and less with the level of TRE in the plasma (see Chapman R W et al., Pulm. Pharmacol. Ther. 49:104-111 (2018), the content of which is incorporated herein by reference in its entirety), the unexpected difference in the lung treprostinil palmitil equivalent: plasma TRE $C_{max}$ ratio indicates that administration of the treprostinil palmitil dry powder formulations beneficially leads to lower systemic exposure to TRE and thus minimizes potential systemic adverse events, such as reductions in systemic blood pressure.

Example 5—Evaluations of Efficacy of Mannitol and Trehalose-Based Treprostinil Palmitil Dry Powder Formulations in Hypoxia Challenged Telemetered Rats This example describes the in vivo efficacy evaluations of two different treprostinil palmitil dry powder formulations: the mannitol-based formulation D and the trehalose-based formulation C described in Example 2 and Example 4 (Tables 35A and 35B). Efficacy was determined in rats that were prepared with a telemetry probe implanted in the right ventricle to measure the inhibition of the increase in right ventricular pulse pressure (RVPP) that was induced by exposure to an inhaled hypoxic gas mixture.

Methods

Experiments were performed in male Sprague Dawley rats that were implanted with telemetry probes in the right ventricle and descending aorta to measure RVPP and mean systemic arterial blood pressure (mSAP). These cardiovascular parameters were measured while breathing normoxic air (21% $O_2$/balance $N_2$), following a 10-min exposure to hypoxic air (10% $O_2$/balance $N_2$) and returned to breathing normoxic air. In each experiment, the increase in RVPP due to the hypoxia challenge (A RVPP due to hypoxia) was measured before drug exposure and at 1, 6, 12 and 24 hours after exposure to inhaled treprostinil palmitil dry powder formulation D or formulation C. The drug formulations were given with a Vilinius Aerosol Generator (VAG) at an output of 1 Volt (V) and delivered into a 12-port nose-only inhalation chamber for 20 min. The aerosols were dispersed from the VAG with a bias flow of 8 L/min and delivered to the bottom of the nose-only inhalation chamber. A filter was connected to one of the nose-only ports and attached to a vacuum flow of 0.5 L/min for 5 min. The amount of treprostinil palmitil deposited on the filter was measured by LC-MS/MS. Plasma and respiratory tissue samples of the rats were analyzed for their concentration(s) of treprostinil palmitil and/or TRE.

Results

Exposure of rats to inhaled hypoxia increased RVPP by 10-13 mmHg over the normoxia values. At the end of the hypoxia challenge, the RVPP immediately decreased within a few minutes and returned to the pre-hypoxia values within 10 minutes. The drug effects were determined by comparing the ARVPP due to hypoxia at various times up to 24 hours after drug exposure to the combined value from 2-3 determinations obtained before drug exposure.

The experimental results are shown in FIG. 41. In FIG. 41, the values are the mean±SEM (n=6-8 rats for formulation D and 4 rats for formulation C). Day −1 represents baseline values before drug exposure, and Day 0 represents values post drug exposure. ARVPP represents the increase in right ventricular pulse pressure. "*" denotes $P<0.05$ compared to combined values (1, 6 and 12 hours) before drug exposure on Day −1. The results indicate that exposure to formulation D reduced the ARVPP due to hypoxia with statistically significant ($P<0.05$) inhibition observed at 1, 6, 12 and 24 hours. Similar results were obtained with formulation C with statistically significant ($P<0.05$) inhibition observed at 1, 6, 12 and 24 hours. By 24 hours after treatment with formulation D and formulation C, the RVPP was trending back to the baseline values observed before drug exposures. As a control, exposure to the inhaled mannitol vehicle (containing mannitol at the targeted weight percent of 69.48 wt %, leucine at the targeted weight percent of 29.78 wt %, and DSPE-PEG2000 at the targeted weight percent of 0.74 wt %) did not inhibit the ARVPP response to hypoxia at 1, 6, 12 and 24 hours after administration (data not shown). The delivered dose of formulation D was 78 μg/kg body weight (lung treprostinil palmitil equivalent concentration of 3072 ng/g) and the delivered dose of formulation C was 58 μg/kg body weight (lung treprostinil palmitil equivalent concentration of 1711 ng/g), based upon the concentration of drug inhaled, the duration of exposure, body weight, respiratory minute volume and a deposition fraction of 1.0. See Alexander D. J. et al., Inhal. Toxicol. 20:1179-1189 (2008), the content of which is incorporated herein by reference in its entirety.

In summary, efficacy evaluations in hypoxia-challenged telemetered rats show that the inhaled treprostinil palmitil dry powder formulations C and D inhibited the increase in RVPP up to 24 hours after drug exposure. By 24 hours, the RVPP responses to hypoxia were trending back to the baseline values observed before exposure to the drugs. By comparison, nebulized INS1009 at an achieved delivered dose of 76 μg/kg inhibited the hypoxia-induced increase in RVPP up to 12 hours with a return to the baseline values by 24 hours. Inhaled treprostinil at the highest dose employed (215 μg/kg) inhibited the hypoxia-induced increase in RVPP for 2 hours and at lower inhaled doses (15, 53, or 110 μg/kg) for 1 hour, respectively. These results demonstrate prolonged inhibition of hypoxia-induced increases in RVPP by the treprostinil palmitil dry powder formulations in telemetered rats.

Example 6—Assessment of Mannitol and Trehalose-Based Treprostinil Palmitil Dry Powder Formulations on Cough and Ventilation in Guinea Pigs This example describes studies on the effects of the mannitol-based treprostinil palmitil dry powder formulation D and the trehalose-based treprostinil palmitil dry powder formulation C (described in Example 2 and Example 4; see the formulation compositions in Tables 35A and 35B) to produce cough, change ventilation and change in Penh, a dimensionless index of altered breathing pattern typically seen during bronchoconstriction in conscious male guinea pigs.

Methods

Experiments were performed in male Hartley guinea pigs. After a 3-day period of acclimation, the guinea pigs were placed in a whole body plethysmograph for the measurement of ventilation (tidal volume, respiratory rate and minute volume), Penh and cough using established techniques. See Corboz et al., J Pharmacol Exp Ther 363: 1-10 (2017); Chong BTY et al., J. Pharmacol. Toxicol. Methods 39, 163-168 (1998); Lomask, Exp. and Toxicol. Pathol. 57,13-20 (2006), the content of each of which is incorporated herein by reference in their entireties. Cough was measured from plethysmograph recordings showing a large inspiration followed by a large expiration and confirmed by manual observations, video recordings and cough sounds. The ventilation, Penh and cough data were measured during a 15-min baseline period before the exposure to the dry powder aerosol. The test articles, which included formulation D, formulation C and their respective vehicles, i.e., the mannitol vehicle (containing mannitol at the targeted weight percent of 69.48 wt %, leucine at the targeted weight percent of 29.78 wt %, and DSPE-PEG2000 at the targeted weight percent of 0.74 wt %), and the trehalose vehicle (containing trehalose at the targeted weight percent of 69.48 wt %, leucine at the targeted weight percent of 29.78 wt %, and DSPE-PEG2000 at the targeted weight percent of 0.74 wt %), were then delivered as dry powders for 15 min followed by a 120 min observation period after the aerosol compounds were administered. The air for the aerosol delivery for all steps of the experiment was supplied by an air compressor. Typical humidity of the supplied air was around 30%, as measured. Ventilation, Penh and cough were measured before, during and after exposure to the test articles. Aerosolized test articles were produced with a Vilnius Aerosol generator (VAG). The air flow rate through the VAG was set at 4.5 L/min to disperse the aerosol and combined with 1 L/min of humidified air (30% humidification) to facilitate aerosol delivery to the plethysmograph and minimize problems with static adhesion. The total inflow of air was therefore 5.5 L/min. The generator output from the VAG was 1, 0.75 and 0.5 Volts with each VAG output given for 15 min to deliver 3 different doses of the drugs, with a higher dose being delivered at the higher voltage. A vacuum flow of 8 L/min was established at the bottom of the plethysmograph such that the air and aerosols entered the top and exited the bottom of the system. A separate vacuum source of 0.5 L/min was connected to the filter that was attached to a port in the plethysmograph to sample the drug (treprostinil palmitil) concentration. The filter sampling was maintained for the full duration of the study; i.e. 135 min, but a 15 min exposure time was used to calculate the aerosol concentration of the drug in the nose-only chamber and the inhaled total delivered drug dose. The filter samples were analyzed for the treprostinil palmitil concentration. At the end of the study the guinea pigs were euthanized and blood (plasma), lungs, trachea, larynx and carina+bronchi were collected to measure the treprostinil palmitil and TRE concentrations in these samples.

Results

Exposure of formulation D, formulation C, or the mannitol and trehalose vehicles, were well tolerated and did not result in any mortality.

Aerosolized formulation D generated at 1 V and administered for 15 min (inhaled total delivered dose=35.8 µg/kg body weight) produced cough in 4 of 6 guinea pigs. The average number of coughs for this exposure was 24±12 coughs. At a setting of 0.75 volts and administered for 15 min (inhaled total delivered dose=12.8 µg/kg body weight), cough was observed in 3 of 4 guinea pigs with an average cough count of 19+7 coughs. At a setting of 0.5 V and administered for 15 min (inhaled total delivered dose=2.3 µg/kg body weight), no cough was observed in 4 of 4 guinea pigs. The mannitol vehicle aerosol generated at a setting of 1 V administered for 15 min did not produce cough in 4 of 4 guinea pigs (Table 38). There were no consistent changes in ventilation with formulation D or the mannitol vehicle and the small increase in Penh observed with this drug did not reach statistical significance compared to the mannitol vehicle.

Aerosolized formulation C generated at a setting of 1 V and administered for 15 min (inhaled total delivered dose=10.2 µg/kg body weight) produced cough in 3 of 6 guinea pigs with an average cough count of 10+5 coughs. At a setting of 0.75 V (inhaled total delivered dose=4.7 µg/kg body weight) and 0.5 V (inhaled total delivered dose=1.5 µg/kg body weight) and administered for 15 min of exposure, formulation C did not cause cough in 4 of 4 guinea pigs in either group. The trehalose vehicle at a voltage of 1 V administered for 15 min did not produce cough in 4 of 4 guinea pigs (Table 38). There were no consistent changes in ventilation or Penh with formulation C or the trehalose vehicle.

The lung treprostinil palmitil equivalent concentration increased as a function of the inhaled drug dose with both formulation D and formulation C, and formulation D had approximately 3-fold higher levels of treprostinil palmitil equivalent in the lungs compared to formulation C (Table 38). There was no difference between these two formulations in the percentage of drug deposition in the upper airway tissues of the larynx, trachea and carina+bronchi as most of the inhaled drug was deposited in the lungs (data not shown). No nasal tissues were collected in this study.

TABLE 38

Summarized data for cough, inhaled dose, treprostinil palmitil equivalent concentration in the lungs and TRE in the plasma of guinea pigs exposed to formulation D or formulation C or their vehicles

| | VAG setting | n | Cough # | Delivered dose (µg/kg)* | Lung treprostinil palmitil equivalent (ng/g)† | Plasma TRE (ng/mL)† |
|---|---|---|---|---|---|---|
| Formulation D | Vehicle | 4 | 0 | — | — | — |
| | 1.0 volt | 6 | 24 | 35.8 | 633 | 0.0782 |
| | 0.75 volt | 4 | 19 | 12.8 | 564 | 0.0330 |
| | 0.5 volt | 4 | 0 | 2.3 | 86.9 | 0.0308 |
| Formulation C | Vehicle | 4 | 0 | — | — | — |
| | 1.0 volt | 6 | 10 | 10.2 | 211 | 0.0398 |
| | 0.75 volt | 4 | 0 | 4.7 | 115 | 0.0150 |
| | 0.5 volt | 4 | 0 | 1.5 | 59.2 | 0.00150 |

*Delivered dose $(\mu g/kg) = \dfrac{C\,(\mu g/L) \times RMV\,(L/min) \times D\,(min) \times DF}{BW\,(kg)}$ †Samples obtained approximately 150 min after exposure to the drug.

The results from this study demonstrate that cough occurred with both formulations and was seen at a threshold inhaled dose of 12.8 µg/kg for formulation D and 10.2 µg/kg for formulation C. These respective doses are 10- and 8-fold higher than the threshold dose of inhaled TRE that causes cough in guinea pigs which is 1.23 µg/kg. After exposure to formulation D or formulation C, the first bout of coughing occurred between 17- and 35-minutes which is later than the timing of cough with nebulized TRE that occurs within the first 10 min of exposure.

The concentration of treprostinil palmitil equivalent in the lungs was approximately three times higher with formulation D (Table 38), and there was no difference between these two formulations in the percentage of drug deposited in the upper airways of the larynx, trachea, and carina plus bronchi as most of the drugs were deposited in the lungs (data not shown). The concentration of TRE in the plasma was between two to three times higher with formulation D compared to formulation C (Table 38).

Example 7—Evaluation of the Effects of Treprostinil Palmitil Dry Powder Formulation in the Treatment of an 8-Week Sugen-Hypoxia (SuHx)—Induced Pulmonary Arterial Hypertension Rat Model The Sugen-Hypoxia (SuHx)—induced PAH model in rats is a well-documented model. The model replicates much of the pathology seen in the clinical disease. In this example, the effects of treprostinil palmitil dry powder formulation D (described in Example 2 and Example 4; see the formulation composition in Table 35A) as well as inhaled treprostinil (TRE), intravenous treprostinil (TRE), and oral Selexipag, on an 8-week SuHx-induced pulmonary arterial hypertension (PAH) model in rats, including pulmonary arterial pressure (PAP) and other cardiovascular parameters, right ventricular hypertrophy, lung and cardiac histopathology and biomarkers associated with PAH, are assessed.

Study Groups, Test Articles and Vehicles and their Administration

Male Sprague Dawley rats weighing between 200 and 250 g are randomized into study groups according to weight to ensure weight ranges are evenly distributed across groups. Table 39 summarizes the study groups and the treatment each study group receives.

TABLE 39

Treatment Group Assignment and Treatment Information

| Group # | Group Description | Treatment Dose | Dosing description | Route of Administration | Treatment Starting Day | Surgery Day | Group Size n |
|---|---|---|---|---|---|---|---|
| 1 | Normoxic control | N/A | N/A | N/A | 22 | 56 | 8 |
| 2 | SuHx + inhaled dry powder vehicle | N/A | 170 mg at 1.0 volt | Inhalation (QD) | 22 | 56 | 11 |
| 3 | SuHx + treprostinil palmitil dry powder formulation D low dose | 57 µg/kg | 90 mg at 0.5 volt | Inhalation (QD) | 22 | 56 | 11 |
| 4 | SuHx + treprostinil palmitil dry powder formulation D high dose | 138 µg/kg | 170 mg at 1.0 volt | Inhalation (QD) | 22 | 56 | 11 |
| 5 | SuHx + nebulized vehicle | N/A | 6 mL | Inhalation (QID) | 22 | 56 | 11 |
| 6 | SuHx + nebulized TRE | 110 µg/kg | 6 mL of 0.5 mM | Inhalation (QID) | 22 | 56 | 11 |
| 7 | SuHx + IV vehicle | N/A | N/A | Continuous intravenous infusion | 22 | 56 | 11 |
| 8 | SuHx + IV TRE | 810 ng/kg/min | 8.75 mg/mL (Day 22 to 39) and 10.7 mg/mL (Day 40 to 56) | Continuous intravenous infusion | 22 | 56 | 11 |
| 9 | SuHx + oral vehicle | N/A | 10 mL/kg | Oral (BID) | 22 | 56 | 11 |
| 10 | SuHx + Selexipag | 30 mg/kg | 10 mL/kg of 3 mg/mL | Oral (BID) | 22 | 56 | 11 |

1. Group 1—Normoxic Control Group

Normoxic control group (Group 1) receives one subcutaneous injection of 100% DMSO at 2 mL/kg (vehicle for sugen) and no treatment.

2. Group 2—Treatment Group with Vehicle for Treprostinil Palmitil Dry Powder Formulation D The vehicle for treprostinil palmitil dry powder formulation D has a targeted composition of 70 wt % mannitol and 30 wt % leucine. Rats in this vehicle treatment group (Group 2) are weighed and put in the cup of a Vilnius Aerosol Generator (VAG) (170 mg of the vehicle is loaded) and administered in a nose-cone chamber at 1 volt, once per day until all the material has been aerosolized. The duration of aerosolization is measured. In parallel with Groups 3 and 4, the vehicle treatment for this group is conducted for 35 days.

3. Groups 3 and 4—Treatment Groups with Treprostinil Palmitil Dry Powder Formulation D For Groups 3 and 4, treprostinil palmitil dry powder formulation D is weighed and put in the cup of a VAG (90 mg is used and generated at 0.5 Volts (V) for the targeted dose of 57 µg/kg, and 170 mg is used and generated at 1 V for the targeted dose of 138 µg/kg). The dry powder formulation is given once per day for 35 days and, for each administration, the VAG is left on until all the material is aerosolized. The duration of aerosolization is measured. The Dry powder formulation is stored at 4±2° C.

4. Group 5—Treatment Group with Nebulized Vehicle for Inhaled Treprostinil (TRE)

The nebulized vehicle for inhaled treprostinil (TRE) is phosphate buffered saline (PBS). In parallel with Group 6, rats in this nebulized vehicle treatment group (Group 5) receive nebulized PBS in a nose cone chamber 4 times over a 12-hour period each day for 35 days.

5. Group 6—Treatment Group with Nebulized Treprostinil (TRE)

The nebulized treprostinil (TRE) solution contains 0.5 mM TRE in PBS at a pH of 7.4. The solution is stored at 4±2° C. and expiration date is set 7 days after preparation. The solution is used to deliver a targeted dose of 110 µg/kg TRE, and administered to rats in Group 6 by inhalation 4 times over a 12-hour period each day for 35 days.

6. Group 7—Treatment Group with Vehicle for Intravenous Treprostinil Via Continuous Infusion The vehicle for intravenous treprostinil is an aqueous solution containing 3.0 mg/mL m-Cresol, 5.3 mg/mL NaCl, and 6.3 mg/mL sodium citrate, with a pH of 6.0-7.2. Rats in this group (Group 7) are each implanted with an osmotic pump filled with the vehicle and subject to continuous infusion at an infusion rate as specified for Group 8 below. In parallel with Group 8, the continuous vehicle infusion for Group 7 is to last 35 days.

7. Group 8—Treatment Group with Intravenous Treprostinil (TRE) Via Continuous Infusion Two solutions are prepared for the intravenous administration of TRE to Group 8. They differ only in the concentration of TRE. Specifically, the first solution is an aqueous solution containing 8.75 mg/mL TRE, 3.0 mg/mL m-Cresol, 5.3 mg/mL NaCl, and 6.3 mg/mL sodium citrate, with a pH of 6.0-7.2. The second solution is an aqueous solution containing 10.7 mg/mL TRE, 3.0 mg/mL m-Cresol, 5.3 mg/mL NaCl, and 6.3 mg/mL sodium citrate, with a pH of 6.0-7.2. Each rat of this group (Group 8) receives an intravenous infusion of TRE using an implanted osmotic pump (ALZET pump). Each ALZET pump is first filled with 2 mL of the first solution with 8.75 mg/mL TRE, which is sufficient to achieve continuous infusion over a 28-day period (based on an infusion rate of 2.5 μL/h) for a 450 g rat and achieve a targeted dose of TRE of 810 ng/kg/min. The ALZET pump is replaced on Day 19 of the infusion (Day 40 of the whole study) and filled with 2 mL of the second solution with 10.7 mg/mL TRE, based on an increase in rat weight to approximately 550 g. Derivations of the TRE concentrations in the first and second solutions are shown below. The continuous IV TRE infusion is to last 35 days.

Derivation of TRE concentration (8.75 mg/mL) in the first solution:
Rat weight assumed to be 450 g
TRE infused=810 ng/kg/min; =364.5 ng/min; =21.87 μg/h; =524.88 μg/day; =18.37 mg/35 days
AlZET infusion rate=2.5 μL/hr; =60 μL/day; =2100 μL/35 days; =2.1 mL/35 days
TRE Concentration=18.37 mg/2.1 mL=8.75 mg/mL Derivation of TRE concentration (10.7 mg/mL) in the second solution
Rat weight assumed to be 550 g
TRE infused=810 ng/kg/min; =445.5 ng/min; =26.73 μg/h; =641.52 μg/day; =22.45 mg/35 days
ALZET infusion rate=2.5 μL/hr; =60 μL/day; =2100 μL/35 days; =2.1 mL/35 days
TRE Concentration=22.45 mg/2.1 mL=10.7 mg/mL 8. Group 9—Treatment Group with Vehicle for Selexipag Via Oral Administration The vehicle for Selexipag is an aqueous solution containing 0.5% (w/v) methylcellulose with a pH of 7.5-8.0. In parallel with Group 10, rats of this group are dosed with the vehicle by oral gavage twice a day for 35 days.

9. Group 10—Treatment Group with Selexipag Via Oral Administration

A Selexipag solution containing 3.0 mg/mL Selexipag in 0.5% (w/v) methyl cellulose with a pH of 7.5 is prepared. The solution is stored at room temperature and expiration date is set 7 days after preparation. The solution is administrated to this group of rats (Group 10) by oral gavage twice a day for a targeted dose of 30 mg/kg at a volume of 10 mL/kg at each administration. The Selexipag treatment is to last 35 days.

Study Design

Table 39 outlines the study design, the details of which are as follows. 1. Induction of PAH The rats are randomized into the treatment groups based on their body weight as described above on Day 21.

On Day 0, a solution of sugen at 10 mg/mL in DMSO is prepared, and rats from Groups 2 to 10 (see Table 39) receive a single subcutaneous injection of sugen (20 mg/kg in 2 mL/kg volume) solution and returned to their cages. Also on Day 0, rats from Group 1 receive one subcutaneous injection of 100% DMSO at 2 mL/kg (vehicle for sugen) and returned to their respective cages.

Rats in Groups 2-10 are placed in cages for which the controlled air is adjusted to receive a $FiO_2$ equivalent to 0.10 (10%) using a mixture of nitrogen and ambient air controlled by the ventilated cage system. They are kept under these hypoxic conditions for 21 days. While in hypoxia, cages are cleaned and changed once a week, exposing the rats to ambient oxygen levels for less than 10 minutes. They are exposed to ambient oxygen levels from Day 22 to Day 56. Group 1 rats remain in cages exposed to ambient oxygen (normoxic) levels for 56 days. The rats are observed on a daily basis for any changes in their behavior and general health status.

Treatment with the test articles or vehicles is administrated from Day 22 to Day 56. Food and water are given ad libitum. Daily observation of the behavior and general health status of the rats is done. Weekly body weight is taken.

2. Echocardiogram

An echocardiogram monitoring of the progression of the disease is carried out on Day 0, Day 21 (before treatment) and on surgery day (Day 56) for all the rats.

3. Blood and Lung PK Sampling

Venous blood (0.5 ml, anticoagulated with EDTA) is sampled from all rats (including the normoxic and vehicle groups), at Day 23 (just before the second dosing), at Day 38 (just before the next dosing) and at Day 57 (24 hours after the last dose). Blood is sampled from the saphenous vein for rats with ALZET pumps, and by the jugular vein for all other rats. Whole blood is centrifuged to yield plasma, which is stored frozen at −80° C. for analysis.

4. Dry Powder Inhalation (Groups 2-4)

During the treatment period, each rat is placed into a nose-cone restraint chamber, which is connected to a 12-port nose-only inhalation chamber (CH Technologies). Treprostinil palmitil dry powder formulation D or its vehicle is delivered using a VAG. Airflow is introduced into the VAG at a flow rate of 7 L/min and connected to the nose-only inhalation chamber. For Group 3 treated with a lower dose of treprostinil palmitil dry powder formulation D, 90 mg of treprostinil palmitil dry powder formulation D is weighed and loaded to the VAG de-agglomerator. The VAG is set to a voltage of 0.5 V, which corresponds to 0.5 mg/L powder concentration (~7 μg/L treprostinil palmitil). For Group 4 treated with a higher dose of treprostinil palmitil dry powder formulation D, 170 mg of treprostinil palmitil dry powder formulation D is weighed and loaded to the VAG de-agglomerator, and is delivered at a voltage of 1 V, which corresponds to 1.0 mg/L powder concentration (~14.7 μg/L treprostinil palmitil). The powder aerosol output concentration is continuously monitored by a portable aerosol monitor (Casella MicroDust Pro). The exact delivery time is recorded. Dry powder left inside the VAG de-agglomerator is weighed to calculate the actual amount of the test dry powder aerosolized. A glass fiber filter, which is connected to a vacuum source at 0.5 L/min vacuum flow, is placed on one of the exposure ports at 5 min after start of aerosolization to collect aerosol from chamber on filter for a period of 5 minutes. All the filter samples are kept at 4° C. until analysis.

Rats from Group 2 receive 170 mg of the vehicle for treprostinil palmitil dry powder formulation D, administrated at 1.0 V set up.

In this study, two different inhalation towers and sets of VAGs and lasers are used, one for the dry powder vehicle and the other for treprostinil palmitil dry powder formulation D.

After removing the remaining powder from the de-agglomerator of the VAG, all parts of the VAG are blown with dry air. The tower is blown with dry air between Group 3 (low dose) and Group 4 (high dose) dosing, and cleaned with an aqueous solution of 0.5% sodium dodecyl sulfate (SDS), tap water and distilled water after Group 4 dosing.

5. Nebulization Inhalation (Groups 5 and 6)

Treprostinil and its vehicle PBS are administered using a nebulizer and a controller (Aeroneb Pro) from Aerogen, which is manufactured to deliver a mass mean aerosol diameter (MMAD) between 2.5 to 4 μm and a range of 0.2-0.4 mL/min of flow rate. During the treatment period, each rat is placed into a nose-cone restraint chamber, which is connected to a 12-port nose-only inhalation chamber (CH Technologies). The volume of the solution to be nebulized is 6 mL with airflow of 6 L/min and the concentration of treprostinil is 0.5 mM. A glass fiber filter is placed on one of the exposure ports and connected to a vacuum source at 0.5 L/min vacuum flow for a period of 5 minutes, i.e. starting at 5 min after the start of the nebulization and ending at 10 min.

Two inhalation towers and two separate sets of nose-cones are used; one for Group 5 receiving PBS, and one for Group 6 receiving TRE.

Cleaning of the nebulizer is performed by sequentially running an aqueous solution of 0.5% SDS, tap water and distilled water through the nebulizer and by nebulizing PBS between each use to wash out any residual drug from the medication cup and through the aperture plate.

The nebulization tower tubing and other materials used in the nebulization process are also cleaned with the agents described above once a day. Additionally, the aerosolization tower tubing and other materials used in the aerosolization process are cleaned with the agents described above after each chamber dosing.

6. IV Continuous Infusion (Groups 7 and 8)

Rats from Group 8 are anesthetized with isoflurane 2% and medical grade air. An incision is made on the back of each rat to place an ALZET pump filled with the first solution with 8.75 mg/mL TRE. A catheter is implanted in the jugular vein and connected to the ALZET pump. For continuous infusion over a 35-days period, on day 19 of the infusion, the catheter is temporarily clamped and the ALZET pump is replaced by a new one filled with the second solution with 10.7 mg/mL TRE. Each rat from Group 7 is implanted with a vehicle-filled ALZET pump.

7. Oral Administration (Groups 9 and 10)

Rats from Group 10 receive the reference compound, Selexipag by oral gavage twice a day from Day 22 to Day 56 (35 days). Care is taken to maintain a uniform suspension of Selexipag by stirring continuously, whilst doses are being drawn up into gavage syringes, filling one gavage syringe at a time and administering that dose before filling the next syringe. Doses are given by oral gavage at 10 mL/kg of body weight at each administration. Rats from Group 9 are dosed with the vehicle twice a day by oral gavage from Day 22 to Day 56 (35 days).

Surgical Instrumentation and Measurement of Hemodynamic and Functional Parameters in Efficacy Study Rats 1. On the selected day of surgery, 24 hours after the last dosing, rats are anaesthetized with a mixture of 2 to 2.5% isoflurane USP (Abbot Laboratories) in oxygen, and placed on a heating pad to maintain body temperature.
2. Rats are tracheotomized and immediately ventilated by means of a positive-pressure rodent respirator set at ~ 10 ml/kg body weight at a frequency of 90 strokes/min.
3. A cannula connected to a pressure transducer is inserted into the left femoral artery to measure the systemic arterial blood pressure (SAP).
4. The heart is exposed through a sternotomy and a 20GA 1.16 in Insyte is introduced into the right ventricle and rapidly hooked up to a saline filled PE-50 catheter connected to a transducer.
5. Following a few seconds of right ventricular pressure recording, the Insyte is further advanced into the pulmonary artery to allow PAP recording for an additional 60 seconds.
6. Hemodynamic parameters are recorded continuously for the duration of the procedure or until loss of PAP signal.
7. Following hemodynamic monitoring, the blood is obtained by heart puncture for biomarker analysis (described below).
8. After collection of the blood samples, the chest cavity is further opened to expose the lung. The muscle over the trachea is dissected away to remove the lungs and heart. Harvested tissues are rinsed with PBS to remove any excess of blood before being weighed.
9. The right lung is tied off and collected immediately for drug concentration and biomarker analysis by separating the four lobes, which are weighed, frozen into liquid nitrogen and stored at −80° C.
10. For the histology and casting of the heart, the process is as follows; 1) Five of the 11 rats in each of Groups 2-10 are reserved to assess the histology and biochemical parameters of the heart and are therefore treated as described in point 11 below; 2) The other 6 rats in each of Groups 2-10 serve to determine the Fulton Index and are treated as described in point 12. After collection of the data for the Fulton index, the cardiac tissue is stored at −80° C. for biomarker analysis.
11. For histology, the left lung is flushed with 0.9% NaCl. The left lung is inflated using a 10 mL syringe filled with fixative, 10% neutral buffered formalin (NBF) with an attached blunt tip needle (23 g). The needle tip is inserted into the trachea, held in place with tied suture while another syringe is tied to the pulmonary artery. The lung is inflated gently at physiological pressure until the lung is fully, uniformly, and consistently expanded (not allowing fixative to ooze through lung surface). This provides optimal vascular and airway expansion without causing excessive tissue disruption. The needle is then removed, suture around trachea tied, and the lung immersed in 10% NBF at a 1:20 tissue to fixative ratio. The heart is rinsed in PBS and then immersed in 10% NBF at a 1:20 tissue to fixative ratio. The tissues are kept in formalin for 24-48 hrs. The left lung and heart are then cut and transferred in 70% ethanol.

All fixed tissues are embedded, sliced and stained. The lung sections are stained with Hematoxylin and Eosin (H&E) for morphological determinations or von Willebrand Factor (VWF) for endothelial cell staining. The heart sections are stained with H&E and either with Sirius red or Trichrome staining for collagen fibers visualization and quantification.

12. As part of the Fulton index, the heart is dissected to separate the right ventricle from the left ventricle with septum, and then weighed separately. After collection of the data for the Fulton index, the cardiac tissue is stored at −80° C. for biomarker analysis.

Acquisition and Analysis of Experimental Data

The experimental trace is analyzed by the Clampfit software from Axon Instruments.

PAP recorded continuously for at least 1 minute or until loss of signal is used to extract the mean, diastolic, and systolic pulmonary pressure.

The systemic arterial pressure (SAP) recorded continuously is used to extract the mean, diastolic and systolic arterial pressure.

At the end of the hemodynamic parameters recording, the right and left ventricle including the septum and the lung lobes are excised to determine wet weights.

The following hemodynamic and cardiac function parameters are quantified with appropriate statistical analysis.

Mean Arterial Systemic Pressure

Mean Arterial Pulmonary Pressure

Diastolic PulmonaryPressure

Systolic Pulmonary Pressure

Systolic Right Ventricular Pressure

Saturation ($SO_2$)

Weight Gain

Lung Weight

Fulton's Index

Heart Rate

Pulse Pressure

Further, molecules indicative of heart biochemistry, including biomarkers of oxidative stress, collagen (Sircol assay) and hydroxyproline content, uric acid, natriretic peptides: BNP, NT-proBNP (biomarkers of heart muscle stress), endothelin-1 (heart failure), angiopoetin (neovascularization), von Willebrand factor (endothelial cells), interleukin-6 (biomarker of heart attack, stroke), Toll receptor C (biomarker of cardiac diseases), plasma cytokines, atrial natriuretic peptide ANP (biomarkers for stroke, coronary artery disease, myocardial infarction and heart failure), Toponin T/I (biomarker of heart ischemia), and CPK-MB (cardiac biomarker for myocardial infarction), are examined.

Also investigated in this example are genes linked to PAH, such as bone morphogenetic type 2 (BMPR1), BMP-9, ABCC8, TBX4, ACVRL, SMAD 4/9, KCNA5 and TET2. Additionally, in heart and lung, genes such as collagen type 1 alpha 1 (COL1A1), collagen type 1 alpha 2 (COL1A2), and collagen type 3 alpha 1 (COL3A1) are associated with the formation and secretion of collagen. P4HA1 a key enzyme in collagen biosynthesis. ACTG2 is a gene associated with myofibroblast differentiation. Changes in the expression of those genes are investigated as well.

It is expected that treprostinil palmitil dry powder formulation D will ameliorate the pathophysiology and histopathology in the pulmonary blood vessels and heart of Su/Hx challenged rats.

While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

Patents, patent applications, patent application publications, journal articles and protocols referenced herein are incorporated by reference in their entireties, for all purposes.

The invention claimed is:

1. A dry powder composition consisting of:
(a) from about 0.1 wt % to about 3 wt % of a compound of Formula (I):

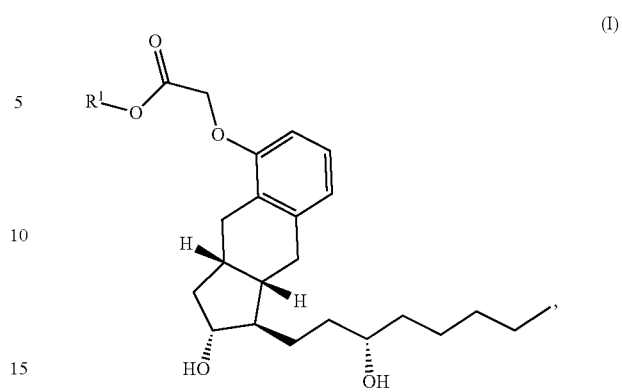

or an enantiomer, diastereomer, or a pharmaceutically acceptable salt thereof, wherein $R^1$ is tetradecyl, pentadecyl, hexadecyl, heptadecyl, or octadecyl, (b) DSPE-PEG2000 in a weight ratio of the DSPE-PEG2000 to the compound of Formula (I), or an enantiomer, diastereomer, or a pharmaceutically acceptable salt thereof in a range of from about 0.1:1 DSPE-PEG2000: the compound of Formula (I), or an enantiomer, diastereomer, or a pharmaceutically acceptable salt thereof to about 1:1 DSPE-PEG2000: the compound of Formula (I), or an enantiomer, diastereomer, or a pharmaceutically acceptable salt thereof, wherein the DSPE-PEG2000 is selected from the group consisting of distearoylphosphatidylethanolamine-polyethylene glycol 2000 and 1,2-distearoyl-sn-glycero-3-phosphoethanolamine-polyethylene glycol 2000, (c) from about 10 wt % to about 50 wt % of leucine, and the balance being (d) a sugar selected from the group consisting of trehalose and mannitol, wherein the entirety of (a), (b), (c), and (d) is 100 wt %.

2. The dry powder composition of claim 1, wherein (a) is a compound of Formula (I) or a pharmaceutically acceptable salt thereof.

3. The dry powder composition of claim 2, wherein (a) is a compound of Formula (I).

4. The dry powder composition of claim 1, wherein $R^1$ is hexadecyl.

5. The dry powder composition of claim 4, wherein $R^1$ is linear hexadecyl.

6. The dry powder composition of claim 1, wherein the compound of Formula (I), or an enantiomer, diastereomer, or a pharmaceutically acceptable salt thereof is present at from about 0.5 wt % to about 2 wt % of the total weight of the dry powder composition.

7. The dry powder composition of claim 1, wherein the compound of Formula (I), or an enantiomer, diastereomer, or a pharmaceutically acceptable salt thereof is present at from about 1 wt % to about 2 wt % of the total weight of the dry powder composition.

8. The dry powder composition of claim 1, wherein the compound of Formula (I), or an enantiomer, diastereomer, or a pharmaceutically acceptable salt thereof is present at from about 1.2 wt % to about 1.8 wt % of the total weight of the dry powder composition.

9. The dry powder composition of claim 1, wherein the compound of Formula (I), or an enantiomer, diastereomer, or a pharmaceutically acceptable salt thereof is present at from about 1.4 wt % to about 1.6 wt % of the total weight of the dry powder composition.

10. The dry powder composition of claim 1, wherein the weight ratio of the DSPE-PEG2000 to the compound of Formula (I), or an enantiomer, diastereomer, or a pharmaceutically acceptable salt thereof is in a range of from about 0.3:1 DSPE-PEG2000: the compound of Formula (I), or an enantiomer, diastereomer, or a pharmaceutically acceptable salt thereof to about 0.7:1 DSPE-PEG2000: the compound of Formula (I), or an enantiomer, diastereomer, or a pharmaceutically acceptable salt thereof.

11. The dry powder composition of claim 1, wherein the weight ratio of the DSPE-PEG2000 to the compound of Formula (I), or an enantiomer, diastereomer, or a pharmaceutically acceptable salt thereof is about 0.5:1 DSPE-PEG2000: the compound of Formula (I), or an enantiomer, diastereomer, or a pharmaceutically acceptable salt thereof.

12. The dry powder composition of claim 1, wherein the leucine is present at from about 15 wt % to about 40 wt % of the total weight of the dry powder composition.

13. The dry powder composition of claim 12, wherein the leucine is present at from about 18 wt % to about 33 wt % of the total weight of the dry powder composition.

14. The dry powder composition of claim 13, wherein the leucine is present at from about 20 wt % to about 30 wt % of the total weight of the dry powder composition.

15. The dry powder composition of claim 14, wherein the leucine is present at from about 25 wt % to about 30 wt % of the total weight of the dry powder composition.

16. The dry powder composition of claim 1, wherein the sugar is mannitol.

17. The dry powder composition of claim 1, wherein the DSPE-PEG2000 is distearoylphosphatidylethanolamine-polyethylene glycol 2000.

18. The dry powder composition of claim 1, wherein the DSPE-PEG2000 is 1,2-distearoyl-sn-glycero-3-phosphoethanolamine-polyethylene glycol 2000.

19. The dry powder composition of claim 3, wherein $R^1$ is linear hexadecyl.

20. The dry powder composition of claim 19, wherein the sugar is mannitol.

* * * * *